United States Patent

Cooper et al.

[11] Patent Number: 5,965,570
[45] Date of Patent: Oct. 12, 1999

[54] TRICYCLIC PIPERIDINYL COMPOUNDS USEFUL AS INHIBITORS OF FARNESYL-PROTEIN TRANSFERASE

[75] Inventors: Alan B. Cooper, West Caldwell; Alan K. Mallams, Hackettstown; Viyyoor M. Girijavallabhan, Parsippany; Ronald J. Doll, Maplewood; Arthur G. Taveras, Rockaway; F. George Njoroge, Union, all of N.J.; John J. Baldwin, Gwynedd Valley, Pa.; John C. Reader, Princeton, N.J.

[73] Assignees: Schering Corporation, Kenilworth; Pharmacopeia Inc., Princeton, both of N.J.

[21] Appl. No.: 08/927,729

[22] Filed: Sep. 11, 1997

Related U.S. Application Data

[60] Provisional application No. 60/026,450, Sep. 13, 1996.

[51] Int. Cl.$^6$ .......................... A61K 31/44; C07D 221/06
[52] U.S. Cl. .......................... 514/290; 514/225; 544/361; 546/93
[58] Field of Search .................. 546/93; 514/290, 514/255; 544/361

[56] References Cited

FOREIGN PATENT DOCUMENTS

| 0 396 083 | 11/1990 | European Pat. Off. . |
|---|---|---|
| 1 593 417 | 7/1981 | United Kingdom . |
| WO 92 00293 | 1/1992 | WIPO . |
| WO 95 10515 | 4/1995 | WIPO . |
| WO 95 10516 | 4/1995 | WIPO . |
| WO 97 18813 | 5/1997 | WIPO . |

*Primary Examiner*—Joseph K. McKane
*Attorney, Agent, or Firm*—Joseph T. Majka

[57] ABSTRACT

Novel tricyclic compounds and pharmaceutical compositions are disclosed which are inhibitors of the enzyme, farnesyl protein transferase. Also disclosed is a method of inhibiting Ras function and therefore inhibiting the abnormal growth of cells. The method comprises administering the novel tricyclic compound to a biological system. In particular, the method inhibits the abnormal growth of cells in a mammal such as a human.

20 Claims, No Drawings

TRICYCLIC PIPERIDINYL COMPOUNDS USEFUL AS INHIBITORS OF FARNESYL-PROTEIN TRANSFERASE

This application is based on provisional application No. 60/026,450 filed Sep. 13, 1996.

BACKGROUND

Patent application WO 95/00497 published Jan. 5, 1995 under the Patent Cooperation Treaty (PCT) describes compounds which inhibit the enzyme, farnesyl-protein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras. Several compounds of this invention have been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in the claimed methods are represented by Formula 1.0:

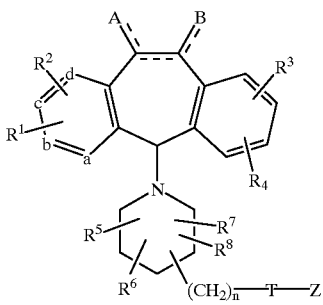

(1.0)

or a pharmaceutically acceptable salt or solvate thereof, wherein:

one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each of a, b, c, and d are independently selected from $CR^1$ or $CR^2$; each $R^1$ and each $R^2$ is independently selected from H, halo, $-CF_3$, $-OR^{10}$, $-COR^{10}$, $-SR^{10}$, $-S(O)_tR^{11}$ (wherein t is 0, 1 or 2), $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$, $-SR^{11}C(O)OR^{11}$, $-SR^{11}N(R^{75})_2$ wherein each $R^{75}$ is independently selected from H and $-C(O)OR^{11}$, benzotriazol-1-yloxy, tetrazol-5-ylthio, or substituted tetrazol-5-ylthio, alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, $R^7$ and $R^8$ each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R_2R^{11}$, $-CO_2R^{10}$, $OPO_3R^{10}$, or $R^5$ is combined with $R^6$ to represent $=O$ or $=S$ and/or $R^7$ is combined with $R^8$ to represent $=O$ or $=S$;

$R^{10}$ represents H, alkyl, cycloalkyl, cycloalkylalkyl, heteroaryl, aryl, aralkyl or $-NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alkynyl;

$R^{11}$ represents alkyl or aryl;

the dotted line between carbon atoms 5 and 6 represents an optional double bond, such that when a double bond is present, A and B independently represent $-NO_2$, $-R^{10}$, halo, $-OR^{11}$, $-OCO_2R^{11}$ or $-OC(O)R^{10}$, and when no double bond is present between carbon atoms 5 and 6, A and B each independently represent $H_2$, $-(OR^{11})_2$, H and halo, dihalo, alkyl and H, (alkyl)$_2$, $-H$ and $-OC(O)R^{10}$, H and $-OR^{10}$, oxy, aryl and H, $=NOR^{10}$ or $-O-(CH_2)_p-O-$ wherein p is 2, 3 or 4;

n is 0 (zero), 1, 2, 3, 4, 5 or 6;

T is $-CO-$; $-SO-$; $-SO_2-$; or $-CR^{30}R^{31}-$ wherein $R^{30}$ and $R^{31}$ independently represent H, alkyl, aryl, aralkyl, heteroalkyl, heteroaryl, heteroarylalkyl, heterocycloalkyl or heterocycloalkylalkyl; and Z represents alkyl, aryl, aralkyl, heteroalkyl, heteroaryl, heteroarylalkyl, heterocycloalkyl, heterocycloalkylalkyl, $-OR^{40}$, $-SR^{40}$, $-CR^{40}R^{42}$, $-NR^{40}R^{42}$,

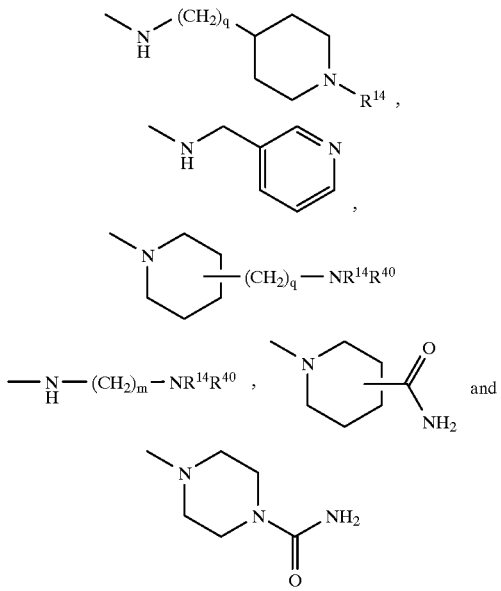

wherein n, $R^{40}$ and $R^{42}$ are defined hereinbefore, m is 2, 3, 4, 5, 6, 7 or 8;

q is 0 (zero), 1 or 2;

and $R^{14}$ represents H, $C_{1-6}$ alkyl, aralkyl, heteroaryl, acyl, carboxamido, carboxamidoalkyl, cyano, alkoxycarbonyl, aralkyloxycarbonyl, D- and L-amino acids covalently bonded through the carboxyl group, imido, imidamido, sulfamoyl, sulfonyl, dialkylphosphinyl, N-glycosyl,

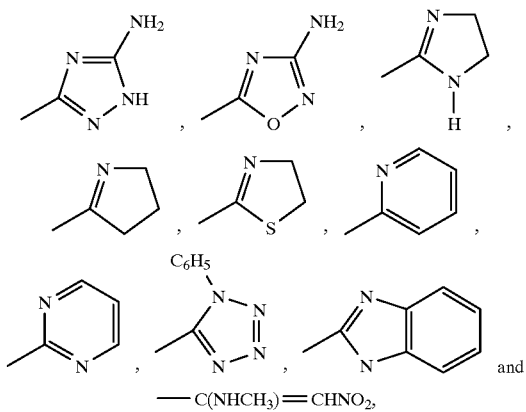

$-C(NHCH_3)=CHNO_2$, with the proviso that when T is $-SO-$, Z is not $-NR^{40}R^{42}$.

In the compounds of formula (1.0), preferably a is N; b, c and d are carbon; A and B each represent $H_2$ and the optional double bond is absent. Also preferred is that $R^1$ and $R^4$ are H and $R^2$ and $R^3$ are halo selected from chloro and bromo; or $R^1$ is H and $R^2$, $R^3$ and $R^4$ are halo selected from chloro and bromo. Also preferred is that $R^2$ and $R^3$ are halo in the 3- and the 8-position on the ring structure; or $R^2$, $R^3$ and $R^4$ are in the 3-, 8- and 10-position on the ring structure. Also preferred is that $R^2$ is Br and $R^3$ is Cl in the 3- and the 8-position on the ring structure; or $R^2$ is Br, $R^3$ is Cl and $R^4$ is Br in the 3-, 8- and 10-position on the ring structure. Also preferred is that each of $R^5$, $R^6$, $R^7$ and $R^8$ is H. Also preferred is that the moiety $-(CH_2)_n-T-Z$ is bonded at the 2-, 3- or 4-position on the piperdinyl ring, more preferably at the 2- or 3-position on the piperdinyl ring.

Also preferred in the compounds of formula (1.0) is that n is zero, 1 or 2; T is $-CO-$ and Z is $-NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl or cycloalkylalkyl; or

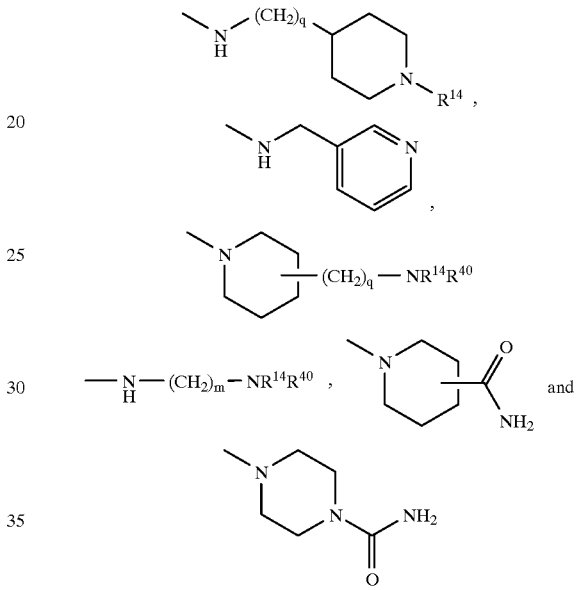

wherein $R^{40}$ is defined hereinbefore, m is 2, 3 or 4;

q is 0 (zero), 1 or 2;

and $R^{14}$ represents H, $C_{1-6}$ alkyl, aralkyl, heteroaryl, acyl, carboxamido, carboxamidoalkyl, cyano, alkoxycarbonyl, aralkyloxycarbonyl imido, imidamido, sulfamoyl, sulfonyl, dialkylphosphinyl, N-glycosyl or $-C(NHCH_3)=CHNO_2$. More preferably, n is zero; Z is $-NR^{40}R^{42}$ wherein $R^{40}$ represents H and $R^{42}$ represents heteroarylalkyl. More preferably $R^{40}$ is H and $R^{42}$ is the heteroaryl moiety 3-pyridylmethyl.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the carbonyl piperazinyl and piperidinyl compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the carbonyl piperazinyl and piperidinyl compounds (1.0) described herein.

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

The following solvents and reagents are referred to herein by the abbreviations indicated:

tetrahydrofuran (THF);
ethanol (EtOH);
methanol (MeOH);
ethyl acetate (EtOAc);
N,N-dimethylformamide (DMF);
trifluoroacetic acid (TFA);
1-hydroxybenzotriazole (HOBT);
1-(3-dimethylaminopropyl)-3-ethyl carbodiimide hydrochloride (DEC);
dimethylsulfoxide (DMSO);
4-methylmopholine (NMM);
dimethylaminopyridine (DMAP); and
dimethoxyethane (DME).
t-butoxycarbonyl (BOC)
acetyl(OAc)

As used herein, the following terms are used as defined below unless otherwise indicated:

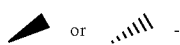

indicates a pure isomer;
when attached to a carbon atom labeled with an asterisk (*), indicates a separated isomer whose stereochemistry is not established;

indicates a racemic mixture;
M$^+$—represents the molecular ion of the molecule in the mass spectrum;
MH$^+$—represents the molecular ion plus hydrogen of the molecule in the mass spectrum;
Bu—represents butyl;
Et—represents ethyl;
Me—represents methyl;
Ph—represents phenyl;
benzotriazol-1-yloxy represents

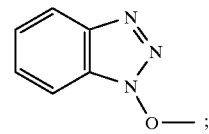

1-methyl-tetrazol-5-ylthio represents

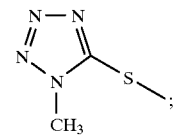

acyl—a moiety of the formula —COR$^{15}$ wherein R$^{15}$ represents H, C$_{1-6}$alkyl, aryl, aralkyl, heteroalkyl, heteroarylalkyl, heterocycloalkyl, heterocycloalkylalkyl or —(CH$_2$)$_k$NR$^{80}$R$^{81}$ wherein k is 1 or 2, and R$^{80}$ and R$^{81}$ may independently represent H, alkyl, cycloalkyl, cycloalkylalkyl, heteroaryl, heteroarylalkyl, aryl or aralkyl;
alkyl—(including the alkyl portions of alkoxy, alkylamino and dialkylamino)—represents straight and branched carbon chains and contains from one to twenty carbon atoms, preferably one to six carbon atoms (i.e. $C_{1-6}$ alkyl); for example methyl, ethyl, propyl, iso-propyl, n-butyl, t-butyl, n-pentyl, isopentyl, hexyl and the like; wherein said alkyl and said $C_{1-6}$ alkyl group may be optionally and independently substituted with one, two, three or more of the following: halo, alkyl, aryl, alkoxy, amino (—$NH_2$), alkylamino, cyano (—CN), —$CF_3$, dialkylamino, hydroxy, oxy (=O), phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$NCOR^{10}$ or —$COOR^{10}$.

alkoxy—an alkyl moiety of one to 20 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

alkoxycarbonyl—represents a alkoxy moiety, as defined above, covalantly bonded to a carbonyl moiety (—CO—) through an oxygen atom, for example, —$COOCH_3$, —$COOCH_2CH_3$ and —$COOC(CH_3)_3$;

alkenyl—represents straight and branched carbon chains having at least one carbon to carbon double bond and containing from 2 to 12 carbon atoms, preferably from 2 to 6 carbon atoms and most preferably from 3 to 6 carbon atoms; wherein said alkenyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

alkynyl—represents straight and branched carbon chains having at least one carbon to carbon triple bond and containing from 2 to 12 carbon atoms, preferably from 2 to 6 carbon atoms; wherein said alkynyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

amino acid—refers to organic compounds having both an amino group (—$NH_2$) and a carboxyl group (—COOH). Representative amino acids include glycine, serine, alanine, phenylalanine, tyrosine, S-methyl methionine and histidine;

aryl (including the aryl portion of aralkyl)—represents a carbocyclic group containing from 6 to 15 carbon atoms and having at least one aromatic ring (e.g., aryl is phenyl), wherein said aryl group optionally can be fused with aryl, cycloalkyl, heteroaryl or heterocycloalkyl rings; and wherein any of the available substitutable carbon and nitrogen atoms in said aryl group and/or said fused ring(s) may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

aralkyl—represents an alkyl group, as defined above, wherein one or more hydrogen atoms of the alkyl moiety have been substituted with one or more aryl groups; wherein said aralkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$; Representative aralkyl groups include benzyl and diphenylmethyl;

aralkyloxy—represents an aralkyl group, as defined above, covalently bonded to an adjacent structural element through an oxygen atom, for example, phenylmethyloxy and phenylethyloxy;

aralkyloxycarbonyl—represents an aralkyloxy group, as defined above, covalantly bonded to a carbonyl moiety (—CO—) through an oxygen atom, for example, —$COOCH_2C_6H_5$ and —$COOCH_2CH_2C_6H_5$;

carboxamido—represents a moiety of the formula —$CONR^{40}R^{42}$, including —$CONH_2$;

carboxamidoalkyl—represents an alkyl group, as defined above, wherein a hydrogen atom of the alkyl moiety has been substituted with a carboxamido moiety, as defined above, through the carbonyl (—CO) portion of the carboxamido moiety, for example, —$CH_2CONH_2$ and —$CH_2CH_2CONH_2$;

cycloalkyl—represents saturated carbocyclic rings branched or unbranched of from 3 to 20 carbon atoms, preferably 3 to 7 carbon atoms; wherein said cycloalkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

cycloalkylalkyl—represents an alkyl group, as defined above, wherein one or more hydrogen atoms of the alkyl moiety have been substituted with one or more cycloalkyl groups; wherein said cycloalkylalkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

halo—represents fluoro, chloro, bromo and iodo;

heteroalkyl—represents straight and branched carbon chains containing from one to twenty carbon atoms, preferably one to six carbon atoms interrupted by 1 to 3 heteroatoms selected from —O—, —S— and —N—; wherein any of the available substitutable carbon and nitrogen atoms in said heteroalkyl chain may be optionally and independently substituted with one, two, three or more of the following: halo, $C_1$–$C_6$ alkyl, aryl, cyano, hydroxy, alkoxy, oxy, phenoxy, —$CF_3$, —$OCF_3$, amino, alkylamino, dialkylamino, heterocycloalkyl, —$SO_2NH_2$, —$NHSO_2R^{10}$, —$SO_2NHR^{10}$, —$SO_2R^{10}$, —$SOR^{10}$, —$SR^{10}$, or —$NHSO_2$, —$NO_2$, —$CONR^{10}$, —$NCOR^{10}$ or —$COOR^{10}$;

heteroaryl—represents cyclic groups having at least one heteroatom selected from O, S and N, said heteroatom(s) interrupting a carbocyclic ring structure and having a sufficient number of delocalized pi electrons to provide aromatic character, with the aromatic heterocyclic groups containing from 2 to 14 carbon atoms, wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independently substituted with one, two, three or more of the following: halo, $C_1$–$C_6$ alkyl, aryl, cyano, hydroxy, alkoxy, oxy, phenoxy, —$CF_3$, —$OCF_3$, amino, alkylamino, dialkylamino, heterocycloalkyl, —$SO_2NH_2$, —$NHSO_2R^{10}$, —$SO_2NHR^{10}$, —$SO_2R^{10}$, —$SOR^{10}$, —$SR^{10}$, or —$NHSO_2$, —$NO_2$, —$CONR^{10}$, —$NCOR^{10}$ or —$COOR^{10}$. Representative heteroaryl groups can include, for example, furanyl, imidazoyl, pyrimidinyl, triazolyl, 2-, 3- or 4-pyridyl or 2-, 3- or 4-pyridyl N-oxide wherein pyridyl N-oxide can be represented as:

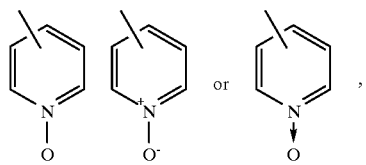

heteroarylalkyl—represents an alkyl group, as defined above, wherein one or more hydrogen atoms have been replaced by one or more heteroaryl groups; wherein said heteroarylalkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$; as exemplified by 2-, 3- or 4-pyridylmethyl or 2-, 3- or 4-pyridylmethyl N-oxide;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S— and —N—, wherein optionally, said ring may contain one or two unsaturated bonds which do not impart aromatic character to the ring; and wherein any of the available substitutable carbon and nitrogen atoms in the ring may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$ Representative heterocycloalkyl groups can include morpholinyl, 2- or 3-tetrahydrofuranyl, 2- or 3-tetrahydrothienyl, 1-, 2-, 3- or 4-piperidinyl, 2- or 3-pyrrolidinyl, 1-, 2-3-piperizinyl, 2- or 4-dioxanyl, or

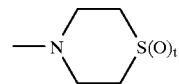

wherein t is 0, 1 or 2;

heterocycloalkylalkyl—represents an alkyl group, as defined above, wherein one or more hydrogen atoms have been replaced by one or more heterocycloalkyl groups; wherein optionally, said ring may contain one or two unsaturated bonds which do not impart aromatic character to the ring; and wherein said heterocycloalkylalkyl group may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$;

imido—represents a moiety of the formula

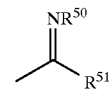

wherein and $R^{50}$ represents H, cyano, aryl, —$SO_2NH_2$, —$SO_2NR^{40}R^{42}$ and carboxamido and $R^{51}$ represents aryl and aryloxy. Representative imido groups can include, for example,

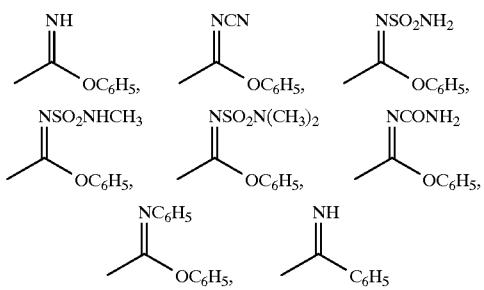

imidamido—represents a moiety of the formula

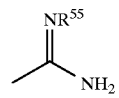

wherein and $R^{55}$ represents H, cyano, —$SO_2NH_2$, —$SO_2NR^{40}R^{42}$, carboxamido, hydroxy and alkoxy. Representative imidamido groups can include, for example,

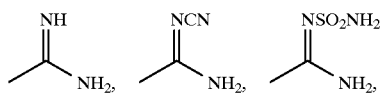

-continued

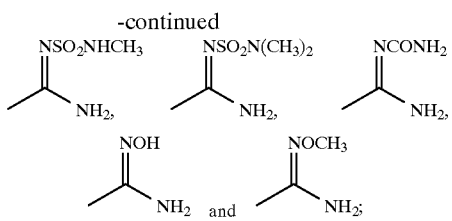

N-glycosyl—represents a pyranosyl or furanosyl monosaccharide. Representative N-glycosyl groups include (N→1)-tetra-O-acetyl-D-glucosyl, (N→1)-tetra-O-acetyl-D-galactosyl and (N→1)-tri-O-acetyl-D-ribosyl, e.g.

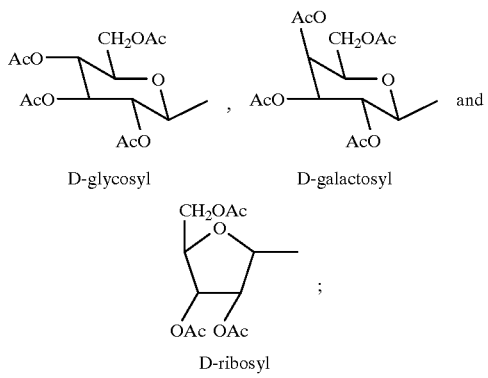

1-amino-2-nitroethenyl represents the formula: —C(NHCH$_3$)=CHNO$_2$;

dialkylphosphinyl—represents a phosphine (—PO) moiety covalently bonded to two alkyl groups. A representative dialkylphosphinyl group is —PO(CH$_3$)$_2$.

sulfamoyl—represents a moiety of the formula —SO$_2$R$^{60}$ wherein R$^{60}$ represents amino, alkylamino and dialkylamino. Representative sulfamoyl groups can include, for example, —SO$_2$NH$_2$, —SO$_2$NHCH$_3$, —SO$_2$N(CH$_3$)$_2$.

sulfonyl—represents a moiety of the formula —SO$_2$R$^{60}$ wherein R$^{60}$ represents alkyl, aryl and arylalkyl. Representative sulfonyl groups can include, for example, —SO$_2$CH$_3$, —SO$_2$C$_6$H$_5$, —SO$_2$C$_6$H$_4$CH$_3$, and —SO$_2$CH$_2$C$_6$H$_5$.

Reference to the position of the substituents R$^1$, R$^2$, R$^3$, and R$^4$ is based on the numbered ring structure:

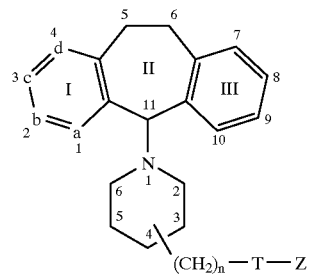

Certain compounds of the invention may exist in different stereoisomeric forms (e.g., isomers such as enantiomers and diastereoisomers). The invention contemplates all such stereoisomers both in pure form and in mixture, including racemic mixtures. For example, the carbon atom at the C-11 position can be in the S or R stereoconfiguration. Also, the carbon atom at the C-2, C-3, C-5 and C-6 positions of the piperidinyl moiety bonded at C-11 can also be in the S or R stereoconfiguration.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also forms salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Compounds of the present invention can be prepared according to the following Scheme 1:

Scheme 1

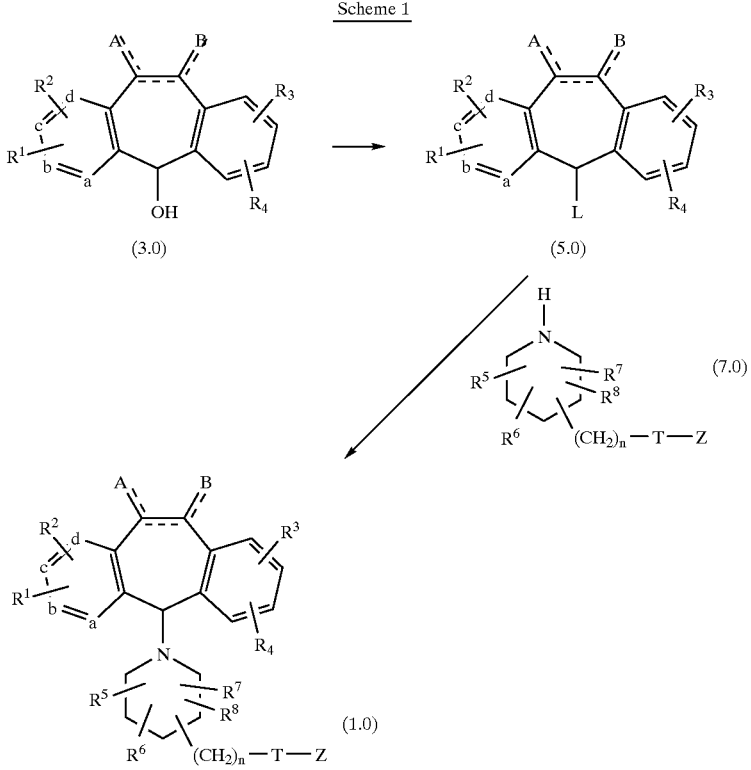

wherein L represents a leaving group such as halo, preferably chloro or a leaving group such as o-tosyl and o-mesyl; the dotted line represents a single or double bond; and a, b, c, d, A, B, $R^1$, $R^2$, $R^3$, $R^4$, $R^5$, $R^6$, $R^7$, $R^8$, n, T and Z are as defined hereinbefore.

Referring to the Scheme 1, compounds of formula (5.0) can be prepared by reacting the compounds of formula (3.0) with a halogenating agent or a sulfonylating agent in the presence of a suitable base, and optional aprotic solvent, in amounts and under conditions effective to give compounds (5.0). Suitable bases include organic bases such as pyridine and triethylamine; or inorganic bases of alkali and alkaline earth metals including carbonates such as sodium, lithium, potassium and cesium carbonates, hydroxides such as sodium, lithium and potassium hydroxides; hydrides such as sodium or potassium hydride; and sodium t-butoxide, preferably sodium hydride. Suitable aprotic solvents include ethers, DMF, DMSO, THF, DME and mixtures thereof, preferably DMF. Preferably the halogenating agent is a chlorinating agent, such as thionyl chloride. The sulfonylating can be methane sulfonyl chloride or toluene sulfonyl chloride. The amounts of the halogenating agent or the sulfonylating agent can range from about one to about 10 moles per mole of compound (3.0). Temperatures can range from 0° to 50° C., or reflux of the reaction mixture.

The desired tricylic piperidinyl compounds of formula (1.0) can be prepared by reacting the compounds of formula (5.0) with a suitably substituted piperidinyl compound of formula (7.0) in the presence of a suitable base and optional aprotic solvent, such as those described above, to give compounds (1.0). The amounts of the substituted piperidinyl compound of formula (7.0) to compound (5.0) can range from about one to about 10 moles per mole of compound (5.0) Temperatures can range from about room temperature to about 80° C.

The tricylic piperidinyl compounds of fomula (1.0) can be isolated from the reaction mixture using conventional procedures, such as, for example, extraction of the reaction mixture from water with organic solvents, evaporation of the organic solvents, followed by chromatography on silica gel or other suitable chromatographic media.

Selected compounds of formula (1.0) can be prepared in accordance with Scheme 2.

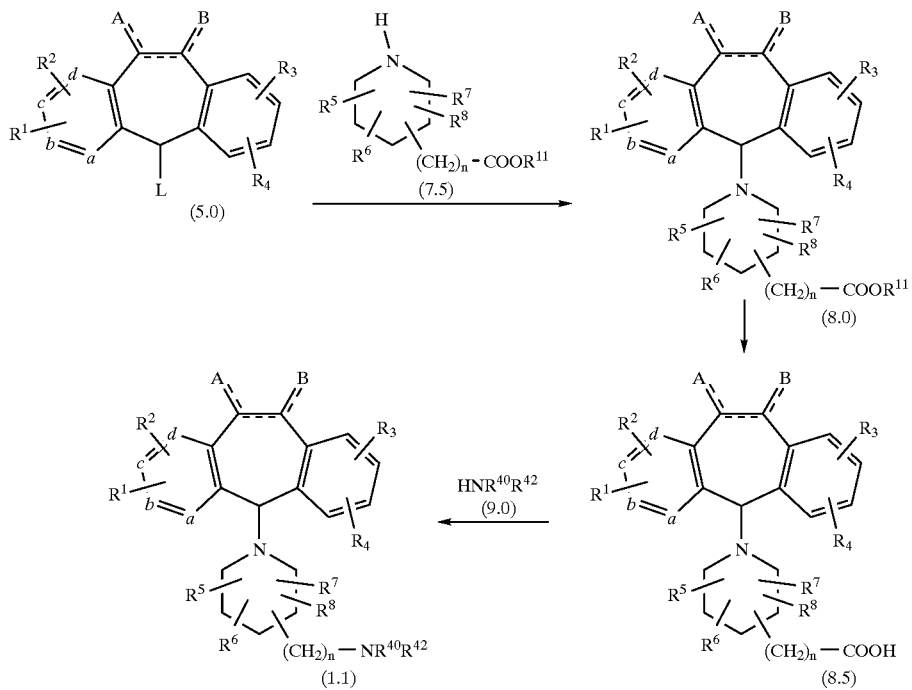

wherein L represents a leaving group, preferably chloro; the dotted line represents a single or double bond; and a, b, c, d, A, B, $R^1$, $R^2$, $R^3$, $R^4$, $R^5$, $R^6$, $R^7$, $R^8$, $R^8$, $R^{11}$, $R^{40}$, $R^{42}$ and n are as defined hereinbefore.

Referring to the Scheme 2, compounds of formula (8.0) can be prepared by reacting the compounds of formula (5.0) with a piperdinyl carboxylic acid ester of formula (7.5 ) in the presence of a base and optional aprotic solvent, in amounts and under conditions effective to give compounds (8.0). Suitable bases and aprotic solvents are described hereinbefore. The amounts of piperidinyl compound (7.5) can range from about 1 to about 10 moles per mole of compound (5.0). Temperatures can range from room temperature to about 80° C. Compound (8.0) can be isolated as described hereinbefore.

Carboxylic acid compounds of formula (8.5) can be prepared by hydrolyzing carboxylic acid ester (8.0) with an excess amount of acid or base. Suitable acids include inorganic acids, organic acids or a mixture thereof. Inorganic acids include hydrogen chloride, hydrogen bromide, sulfuric acid, nitric acid, phosphoric acid, perchloric acid and the like. Organic acids include acetic, citric, formic, maleic, tartaric, methanesulfonic acid and arylsulfonic acids. Suitable bases, such as sodium hydroxide or lithium hydroxide, preferably in an aqueous alcohol, have been described hereinbefore. The temperature can range from about 0° C. to about 100° C.

The desired amide compounds of formula (1.1) can be prepared by reacting the compounds of formula (8.5) with a suitable amine of formula (9.0) in the presence of a coupling agent such as DEC/HOBT, a base such as NMM and a suitable aprotic solvent effective to give amide compound (1.1). Suitable bases and aprotic solvents are described hereinbefore. The amounts of amine (9.0) can range from about 1 to about 10 moles per mole of carboxylic acid (8.5). Temperatures can range from 0° to 100° C. Compound (1.1) can be isolated as described hereinbefore.

Compounds of the present invention and preparative starting materials therof, are exemplified by the following examples, which should not be construed as limiting the scope of the disclosure.

EXAMPLE 1

1-[8-Chloro-6,11-dihydro-5H-benzo[5,6]cyclohepta[1,2-b]pyridin-11-yl]-N-(4-pyridinyl)-4-piperidinecarboxamide

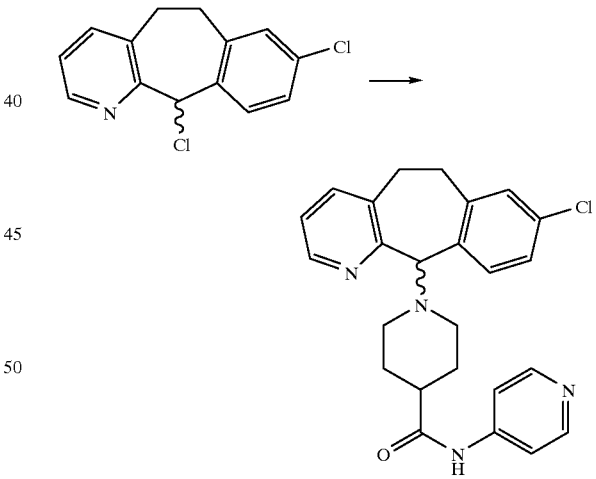

8,11-Dichloro-6,11-dihydro-5H-benzo[5,6]cyclohepta[1,2-b]pyridine (prepared as described in Preparative Example 7, Step B in INO291K) (0.088 g; 1 equivalent) in anhydrous toluene (0.819 ml) is added to anhydrous DMSO (1.5 ml). 4-Piperidinyl-N-(4-pyridinyl)carboxmide (0.0684 g; 1 equivalent) (prepared as described in Preparative Example 1, Step C below) is added and the mixture is stirred at 25° C. for 22 h. The mixture is diluted with dichloromethane and washed with water. The dichloromethane layer is dried over magnesium sulfate, filtered and evaporated to dryness. The product is chromatographed on a silica gel column (15×2.5 cm) using 1% increasing to 8% (10% concentrated ammonium hydroxide in methanol)-dichloromethane as the eluant to give the title compound (0.0272 g; 19% yield), CIMS: m/z 433 (MH+).

FPT $IC_{50}$=9.24 μM

| | | $\delta_c$ (CDCI$_3$) |
|---|---|---|
| Tricyclic | CH$_2$: | 30.4, 30.2 |
| | CH: | 146.1, 139.5, 130.9, 123.4, 126.1, 132.4, 80.2 |
| | C: | 141.3, 135.2, 136.7, 134.0, 158.1 |
| Piperidine | CH$_2$: | 29.0, 51.4, 51.2, 28.7 |
| | CH: | 44.3 |
| | C: | 175.3 |
| Piperidine | CH: | 150.6, 113.9, 113.9, 150.6 |
| N-substituent | C: | 146.1 |

1-(3-Bromo-8-chloro-6,11-dihydro-5H-benzo[5,6]cyclohepta[1,2-b]pyridin-11-yl)-N-(4-pyridinyl)-4-piperidinecarboxamide

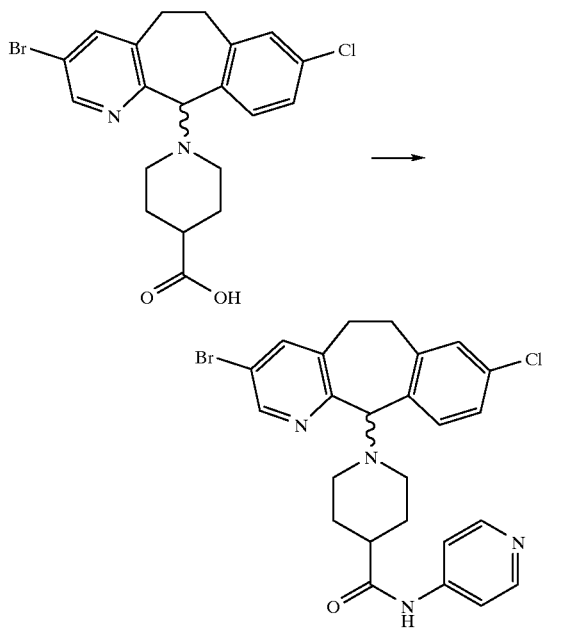

1-[3-Bromo-8-chloro-6,1 1-dihydro-5H-benzo[5,6]cyclohepta[1,2-b]pyridin-11-yl]-4-piperidinecarboxylate (0.25 g) (1 equivalent) (prepared as described in Preparative Example 2 below) dissolved in anhydrous DMF (9 ml) is added to a solution of 4-aminopyridine (0.0761 g) (1.5 equivalents), DEC (0.155 g) (1.5 equivalents), HOBT (0.1093 g) (1.5 equivalents) and N-methylmorpholine (0.0889 ml) (1.5 equivalents) in anhydrous DMF (4 ml) and the mixture is stirred at 25° C. for 42 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 1.5% increasing to 3% (10% concentrated ammonium hydroxide in methanol)-dichloromethane as the eluant to give the title compound (0.0308 g; 12%), CIMS: m/z 511 (MH+).

FPT Inhibition=0% @ 0.39 μM

| | | $\delta_c$ (CDCI$_3$) |
|---|---|---|
| Tricyclic | CH$_2$: | 30.4, 29.9 |
| | CH: | 146.9, 141.3, 132.2, 126.1, 130.5, 79.4 |
| | C: | 119.8, 140.7, 134.0, 136.1, 136.7, 156.5 |
| Piperidine | CH$_2$: | 29.0, 51.2, 51.5, 30.4 |
| | CH: | 44.5 |
| | C: | 174.6 |
| Piperidine | CH: | 150.5, 113.8, 113.8, 150.5 |
| N-substituent | C: | 145.9 |

EXAMPLE 3

1-(3-Bromo-8-chloro-6,11-dihydro-5H-benzo[5,6]cyclohepta[1,2-b]pyridin-11-yl)-N-(4-pyridinylmethyl)-4-piperidinecarboxamide

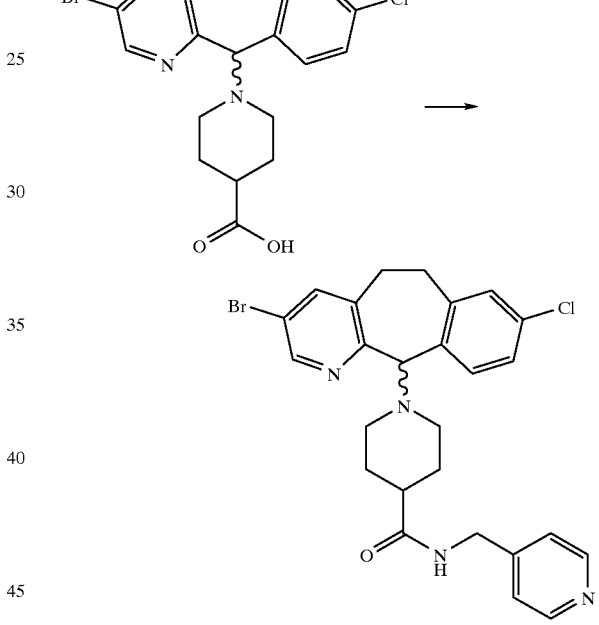

1-(3-Bromo-8-chloro-6,11-dihydro-5H-benzo[5,6]cyclohepta[1,2-b]pyridin-11-yl)-4-piperidinecarboxylate (0.25 g; 1 equivalent) (prepared as described in Preparative Example 2 below) dissolved in anhydrous DMF (9 ml) is added to a solution of 4-aminomethylpyridine (0.0821 ml; 1.5 equivalents), DEC (0.155 g; 1.5 equivalents), HOBT (0.1093 g; 1.5 equivalents) and N-methylmorpholine (0.0889 ml; 1.5 equivalents) in anhydrous DMF (4 ml) and the mixture is stirred at 25° C. for 19 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (30×2.5 cm) using 2% increasing to 3% (10% concentrated ammonium hydroxide in methanol)-dichloromethane as the eluant to give the title compound (0.2128 g; 75% yield), FABMS: m/z 524.9 (MH+).

FPT Inhibition=21% @ 1.1 μM

| | | δ$_c$ (CDCl$_3$) |
|---|---|---|
| Tricyclic | CH$_2$: | 30.4, 30.3 |
| | CH: | 146.9, 141.2, 132.2, 126.1, 130.6, 79.4 |
| | C: | 119.9, 140.7, 134.0, 136.1, 136.7, 156.5 |
| Piperidine | CH$_2$: | 29.2, 51.4, 51.6, 29.2 |
| | CH: | 43.3 |
| | C: | 175.3 |
| Piperidine | CH$_2$: | 42.1 |
| N-substituent | CH: | 122.3, 149.9, 149.9, 122.3 |
| | C: | 147.7 |

FPT IC$_{50}$=1.3 μM

| | | δ$_c$ (CDCl$_3$) |
|---|---|---|
| Tricyclic | CH$_2$: | 30.4, 30.3 |
| | CH: | 146.9, 141.3, 132.3, 126.1, 130.6, 79.4 |
| | C: | 119.9, 140.7, 134.0, 136.2, 136.7, 156.6 |
| Piperidine | CH$_2$: | 29.2, 51.4, 51.7, 29.2 |
| | CH: | 43.4 |
| | C: | 175.2 |
| Piperidine | CH$_2$: | 40.9 |
| N-substituent | CH: | 149.1, 135.7, 123.7, 148.8 |
| | C: | 134.2 |

EXAMPLE 4

1-(3-Bromo-8-chloro-6,11-dihydro-5H-benzo[5,6]cyclohepta[1,2-b]pyridin-11-yl)-N-(3-pyridinylmethyl)-4-piperidinecarboxamide

EXAMPLE 5

1-(3-Bromo-8-chloro-6,11-dihydro-5H-benzo[5,6]cyclohepta[1,2-b]pyridin-11-yl)-N-(2-pyridinylmethyl)-4-piperidinecarboxamide

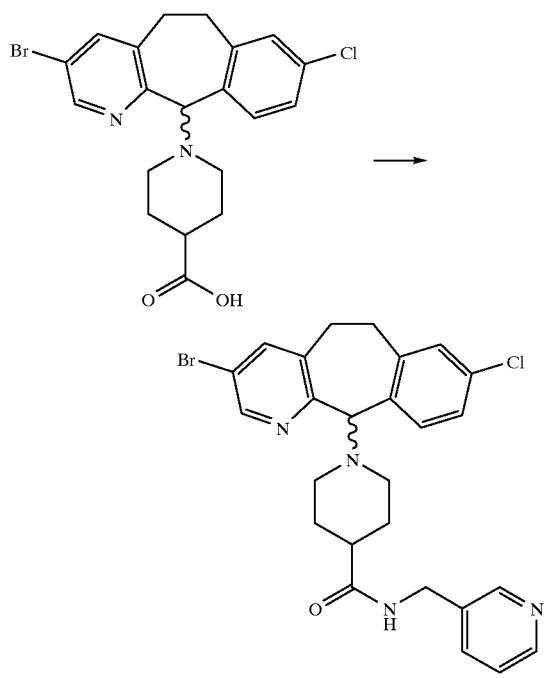

1-(3-Bromo-8-chloro-6,11-dihydro-5H-benzo[5,6]cyclohepta[1,2-b]pyridin-11-yl)-4-piperidinecarboxylate (0.25 g; 1 equivalent) (prepared as described in Preparative Example 2 below) dissolved in anhydrous DMF (9 ml) is added to a solution of 3-aminomethylpyridine (0.0823 ml; 1.5 equivalents), DEC (0.155 g; 1.5 equivalents), HOBT (0.1093 g; 1.5 equivalents) and N-methylmorpholine (0.0889 ml; 1.5 equivalents) in anhydrous DMF (4 ml) and the mixture is stirred at 25° C. for 18 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 2% (10% concentrated ammonium hydroxide in methanol)-dichloromethane as the eluant to give the title compound (0.246 g; 87%), FABMS: m/z 525 (MH$^+$).

1-(3-Bromo-8-chloro-6,11-dihydro-5H-benzo[5,6]cyclohepta[1,2-b]pyridin-11-yl)-4-piperidinecarboxylate (0.25 g; 1 equivalent) (prepared as described in Preparative Example 2 below) dissolved in anhydrous DMF (9 ml) is added to a solution of 2-aminomethylpyridine (0.0834 ml; 1.5 equivalents), DEC (0.155 g; 1.5 equivalents), HOBT (0.1093 g; 1.5 equivalents) and N-methylmorpholine (0.0889 ml; 1.5 equivalents) in anhydrous DMF (4 ml) and the mixture is stirred at 25° C. for 18 h.

The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 0.85% (10% concentrated ammonium hydroxide in methanol)-dichloromethane as the eluant to give the title compound (0.2475 g; 87% yield), FABMS: m/z 525 (MH$^+$).

FPT IC$_{50}$=1.8 μM

| | | δ$_c$ (CDCl$_3$) |
|---|---|---|
| Tricyclic | CH$_2$: | 30.4, 30.3 |
| | CH: | 146.9, 141.2, 132.3, 126.1, 130.6, 79.5 |
| | C: | 119.8, 140.7, 133.9, 136.3, 136.7, 156.7 |
| Piperidine | CH$_2$: | 29.1, 51.5, 51.7, 29.1 |
| | CH: | 43.4 |
| | C: | 175.1 |
| Piperidine | CH$_2$: | 44.2 |
| N-substituent | CH: | 122.4, 137.1, 122.2, 148.9 |
| | C: | 156.2 |

FPT Inhibition=9% @ 1.1 μM

| | | δ$_c$ (CDCl$_3$) |
|---|---|---|
| Tricyclic | CH$_2$: | 30.4, 30.3 |
| | CH: | 146.9, 141.2, 132.3, 126.1, 130.6, 79.5 |
| | C: | 119.8, 140.7, 133.9, 136.4, 136.7, 156.8 |
| Piperidine | CH$_2$: | 29.1, 29.1, 51.5, 51.7 |
| | CH: | 43.5 |
| | C: | 174.9 |
| Piperidine | CH$_2$: | 38.6, 36.7 |
| N-Substituent | CH: | 123.6, 136.9, 121.7, 149.0 |
| | C: | 159.7 |

EXAMPLE 6

1-(3-Bromo-8-chloro-6,11-dihydro-5H-benzo[5,6]cyclohepta[1,2-b]pyridin-11-yl)-N-(2-pyridinylethyl)-4-piperidinecarboxamide

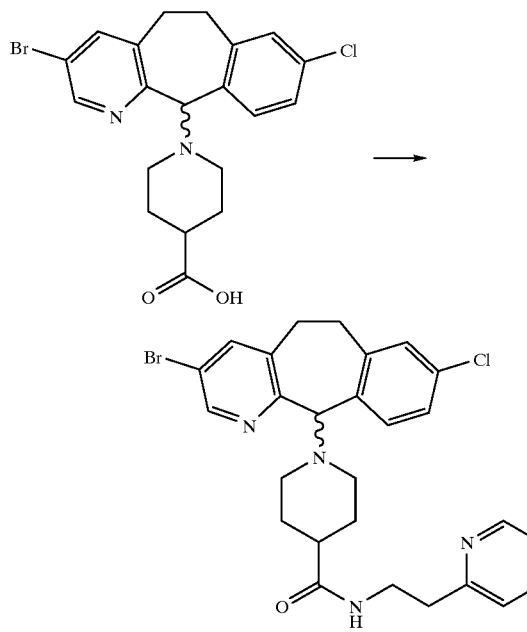

1-(3-Bromo-8-chloro-6,11-dihydro-5H-benzo[5,6]cyclohepta[1,2-b]pyridin-11-yl)-4-piperidinecarboxylate (0.4 g; 1 equivalent) (prepared as described in Preparative Example 2 below) dissolved in anhydrous DMF (14 ml) is added to a solution of 2-aminoethylpyridine (0.134 ml; 1.3 equivalents), DEC (0.215 g; 1.3 equivalents), HOBT (0.1515 g; 1.3 equivalents) and N-methylmorpholine (0.123 ml; 2.6 equivalents) in anhydrous DMF (6 ml) and the mixture is stirred at 25° C. for 67 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 1% increasing to 2% (10% concentrated ammonium hydroxide in methanol)-dichloromethane as the eluant to give the title compound (0.4003 g; 86% yield), FABMS: m/z 539.2 (MH$^+$).

EXAMPLE 7

1-(3-Bromo-8-chloro-6,11-dihydro-5H-benzo[5,6]cyclohepta[1,2-b]pyridin-11-yl)-N-[4-(N-carboxamidopiperidinyl)]-4-piperidinecarboxamide

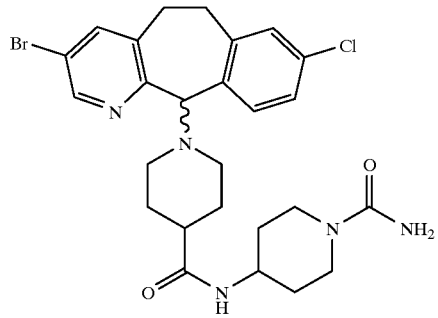

Step A 1-(3-Bromo-8-chloro-6,11-dihydro-5H-benzo[5,6]cyclohepta[1,2-b]pyridin-11-yl)-N-[4-(N-benzylpiperidinyl)]-4-piperidinecarboxamide

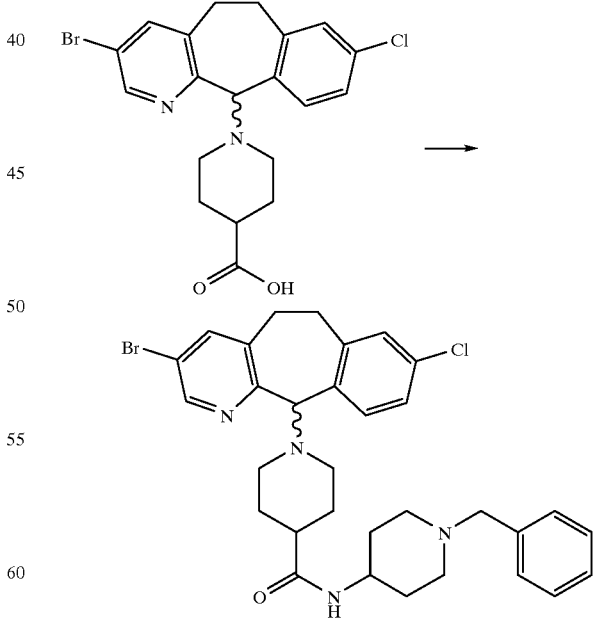

1-(3-Bromo-8-chloro-6,11-dihydro-5H-benzo[5,6]cyclohepta[1,2-b]pyridin-11-yl)-4-piperidinecarboxylate (0.8 g; 1 equivalent) (prepared as described in Preparative Example 2 below) dissolved in anhydrous DMF (29 ml) is added to a solution of 1-N-benzyl-4-aminopiperidine (0.4573 ml) (1.3 equivalents), DEC (0.43 g; 1.3 equivalents), HOBT (0.303 g; 1.3 equivalents) and N-methylmorpholine (0.494 ml; 2.6 equivalents) in anhydrous DMF (12.8 ml) and the mixture is stirred at 25° C. for 18 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 2% (10% concentrated ammonium hydroxide in methanol)-dichloromethane as the eluant to give the title compound (0.8143 g; 78% yield), FABMS: m/z 607.1 (MH$^+$).

|  |  | $\delta_c$ (CDCl$_3$) |
|---|---|---|
| Tricyclic | CH$_2$: | 30.4, 30.3 |
|  | CH: | 146.9, 141.2, 132.2, 126.1, 130.6, 79.5 |
|  | C: | 119.8, 140.7, 133.9, 136.3, 136.7, 156.8 |
| Piperidine | CH$_2$: | 29.2, 51.4, 51.7, 29.2 |
|  | CH: | 43.6 |
|  | C: | 174.3 |
| Piperidine N-substituent | CH$_2$: | 52.3, 52.3, 32.3, 32.3, 63.0 |
|  | CH: | 46.3, 128.3, 128.3, 129.2, 129.2, 127.2 |
|  | C: | 138.1 |

Step B
1-(3-Bromo-8-chloro-6,11-dihydro-5H-benzo[5,6]cyclohepta[1,2-b]pyridin-11-yl)-N-(4-piperidinyl)-4-piperidinecarboxamide

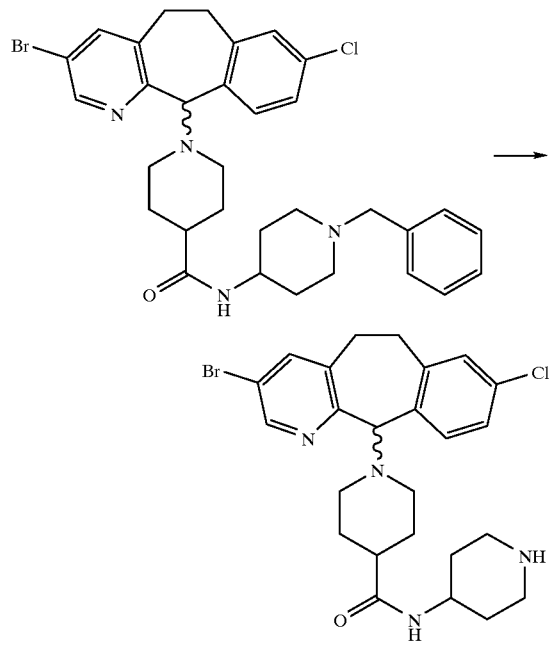

1-(3-Bromo-8-chloro-6,11-dihydro-5H-benzo[5,6]cyclohepta[1,2-b]pyridin-11-yl)-N-[4-(N-benzylpiperidinyl)]-4-piperidinecarboxamide (0.51 g; 1 equivalent) (prepared as described in Step A above) is dissolved in anhydrous dichloromethane (3 ml) and the solution is cooled to 0° C. α-Chloroethoxycarbonyl chloride (0.09027 ml; 1 equivalent) is added over 5 minutes and the solution is allowed to warm to 25° C. over 1 h. The dichloromethane is removed in vacuo and anhydrous methanol (14 ml) is added. The solution is heated under reflux for 1 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 2.5% (10% concentrated ammonium hydroxide in methanol)-dichloromethane as the eluant to give unreacted 1-(3-bromo-8-chloro-6,11-dihydro-5H-benzo[5,6]cyclohepta[1,2-b]pyridin-11-yl)-N-[4-(N-benzylpiperidinyl)]-4-piperidinecarboxamide (0.1921 g; 38% yield) and the title compound (0.199 g; 46%), FABMS: m/z 517.5 (MH$^+$).

FPT Inhibition=8.75% @ 0.39 µM

|  |  | $\delta_c$ (CDCl$_3$ + CD$_3$OD) |
|---|---|---|
| Tricyclic | CH$_2$: | 30.3, 30.2 |
|  | CH: | 146.6, 141.4, 132.2, 126.1, 130.5, 79.2 |
|  | C: | 119.8, 140.6, 133.9, 136.1, 136.9, 156.7 |
| Piperidine | CH$_2$: | 29.0, 51.4, 51.7, 29.0 |
|  | CH: | 43.4 |
|  | C: | 175.0 |
| Piperidine N-substituent | CH$_2$: | 44.9, 44.9, 32.0, 32.0 |
|  | CH: | 46.0 |

Step C
1-(3-Bromo-8-chloro-6,11-dihydro-5H-benzo[5,6]cyclohepta[1,2-b]pyridin-11-yl)-N-[4-(N-carboxamidopiperidinyl)]-4-piperidinecarboxamide

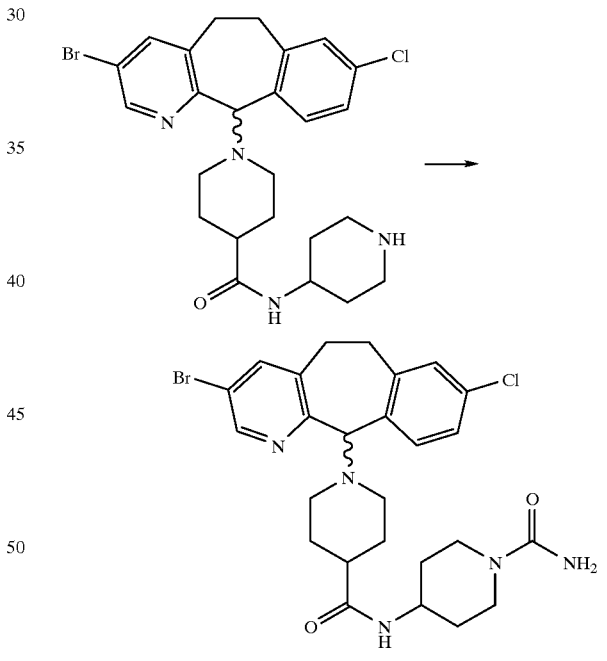

1-(3-Bromo-8-chloro-6,11-dihydro-5H-benzo[5,6]cyclohepta[1,2-b]pyridin-11-yl)-N-(4-piperidinyl)-4-piperidinecarboxamide (0.1191 g; 1 equivalent) (prepared as described in Step B above) is dissolved in anhydrous dichloromethane (3.3 ml). Trimethylsilylisocyanate (0.467 ml; 15 equivalents) is added and the mixture is stirred under argon at 25° C. for 22 h. Additional trimethylsilylisocyanate (0.156 ml; 5 equivalents) is added and the mixture is stirred for a total of 27 h. The solution is diluted with dichloromethane and washed with saturated aqueous sodium bicarbonate. The dichloromethane layer is dried over magnesium sulfate, filtered and evaporated to dryness. The product is chromatographed on a silica gel column (15×2.5 cm) using 4% (10% concentrated ammonium hydroxide in methanol)-dichloromethane as the eluant to give the title compound (0.0678 g; 53% yield), FABMS: m/z 560 (MH$^+$). FPT Inhibition=15% @ 0.36 μM

|  |  | δ$_c$ (CDCl$_3$) |
|---|---|---|
| Tricyclic | CH$_2$: | 30.4, 30.3 |
|  | CH: | 146.8, 141.2, 132.2, 126.1, 130.6, 79.4 |
|  | C: | 119.8, 140.7, 133.9, 136.2, 136.7, 156.7 |
| Piperidine | CH$_2$: | 29.1, 51.4, 51.7, 29.1 |
|  | CH: | 43.5 |
|  | C: | 174.7 |
| Piperidine | CH$_2$: | 43.3, 43.3, 31.9, 31.9 |
| N-substituent | CH: | 46.3 |
|  | C: | 158.1 |

EXAMPLE 8
1-(3-Bromo-8-chloro-6,11-dihydro-5H-benzo[5,6]cyclohepta[1,2-b]pyridin-11-yl)-N-[4-(N-carboxamidopiperidinyl)methyl]-4-piperidinecarboxamide

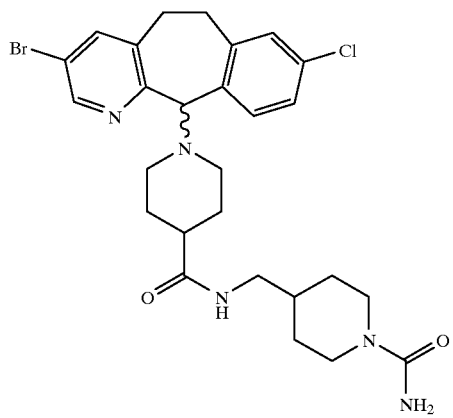

Procedure 1, Step A
1-(3-Bromo-8-chloro-6,11-dihydro-5H-benzo[5,6]cyclohepta[1,2-b]pyridin-11-yl)-N-[4-(N-benzylpiperidinyl)methyl]-4-piperidinecarboxamide

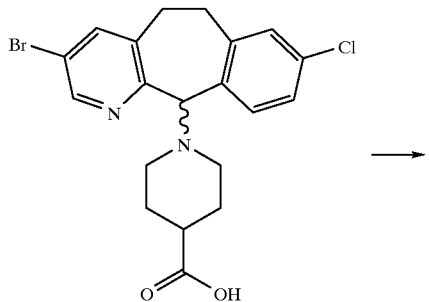

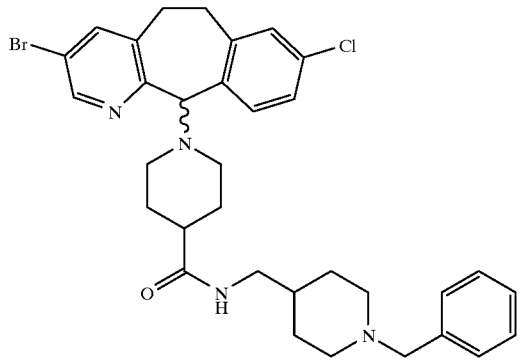

1-(3-Bromo-8-chloro-6,11-dihydro-5H-benzo[5,6]cyclohepta[1,2-b]pyridin-11-yl)-4-piperidinecarboxylate (0.8 g; 1 equivalent) (prepared as described in Preparative Example 2 below) dissolved in anhydrous DMF (29 ml) is added to a solution of 1-N-benzyl-4-aminomethylpiperidine (0.4581 g; 1.3 equivalents) (prepared as described in Preparative Example 4, Step B below), DEC (0.43 g) (1.3 equivalents), HOBT (0.303 g; 1.3 equivalents) and N-methylmorpholine (0.493 ml; 2.6 equivalents) in anhydrous DMF (12.8 ml) and the mixture is stirred at 25° C. for 24 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 2% (10% concentrated ammonium hydroxide in methanol)-dichloromethane as the eluant to give the title compound (0.7475 g; 70% yield), FABMS: m/z 621.6 (MH$^+$).

|  |  | δ$_c$ (CDCl$_3$) |
|---|---|---|
| Tricyclic | CH$_2$: | 30.4, 30.3 |
|  | CH: | 146.9, 141.2, 132.2, 126.1, 130.6, 79.5 |
|  | C: | 119.8, 140.7, 133.9, 136.3, 136.7, 156.8 |
| Piperidine | CH$_2$: | 29.3, 51.5, 51.8, 29.3 |
|  | CH: | 43.7 |
|  | C: | 175.1 |
| Piperidine | CH$_2$: | 53.3, 29.9, 29.9, 53.3, 63.4, 44.9 |
| N-substituent | CH: | 36.0, 128.2, 129.2, 127.0, 129.2, 128.2 |
|  | C: | 138.3 |

Step B 1-(3-Bromo-8-chloro-6,11-dihydro-5H-benzo[5,6]cyclohepta[1,2-b]pyridin-11-yl)-N-(4-piperidinyl)-4-piperidinecarboxamide

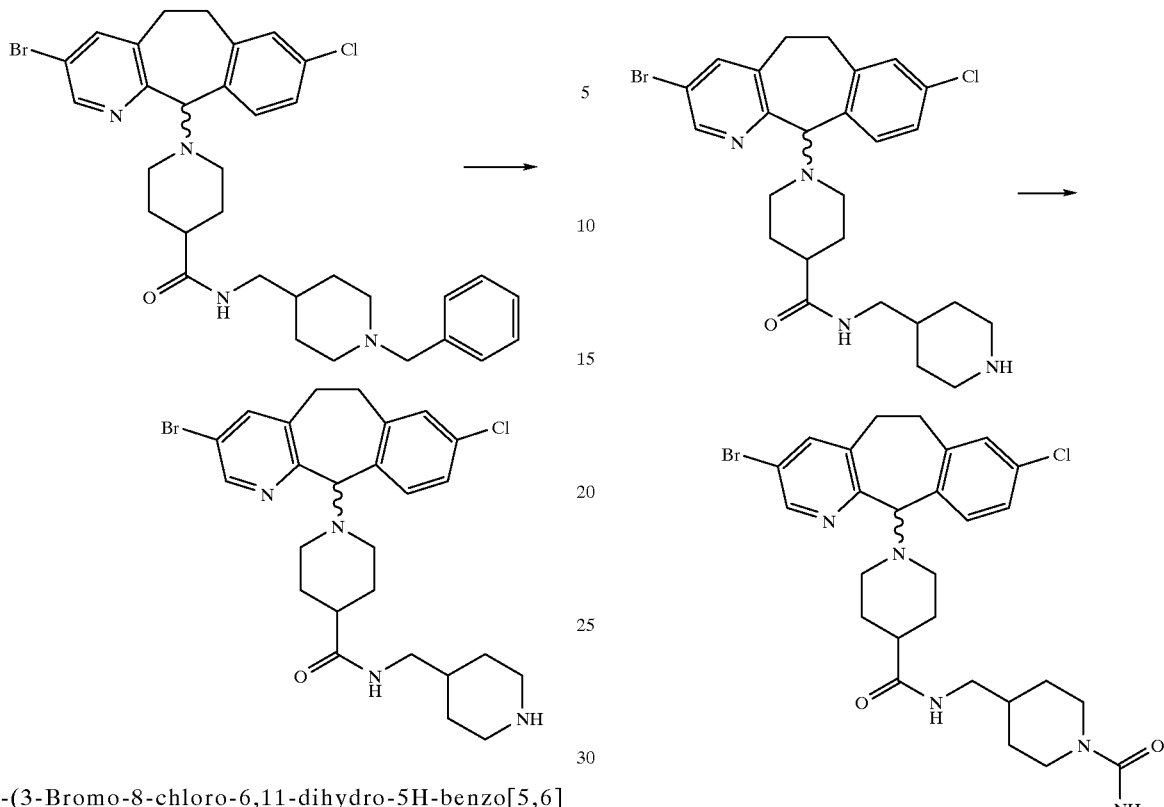

1-(3-Bromo-8-chloro-6,11-dihydro-5H-benzo[5,6]cyclohepta[1,2-b]pyridin-11-yl)-N-[4-(N-benzylpiperidinylmethyl)]-4-piperidinecarboxamide (0.568 g; 1 equivalent) (prepared as described in Step A above) is dissolved in anhydrous dichloromethane (5.9 ml) and the solution is cooled to 0° C. α-Chloroethoxycarbonyl chloride (0.487 ml; 5 equivalents) is added over 30 minutes and the solution is allowed to warm to 25° C. over 2.5 h. The dichloromethane is removed in vacuo and anhydrous methanol (14.2 ml) is added. The solution is heated under reflux for 1.25 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (30×2.5 cm) using 2% (10% concentrated ammonium hydroxide in methanol)-dichloromethane as the eluant to give unreacted 1-(3-bromo-8-chloro-6,11-dihydro-5H-benzo[5,6]cyclohepta[1,2-b]pyridin-11-yl)-N-[4-(N-benzylpiperidinyl)]-4-piperidinecarboxamide (0.1487 g; 23% yield) and the title compound (0.1932 g; 34% yield), FABMS: m/z 531.0 (MH+). The title compound is identical to that prepared in Procedure 2, Step B below. FPT Inhibition=12% @ 0.38 μM

|  |  | $\delta_c$ (CDCl$_3$) |
|---|---|---|
| Tricyclic | CH$_2$: | 30.4, 30.3 |
|  | CH: | 146.9, 141.2, 132.2, 126.1, 130.6, 79.5 |
|  | C: | 119.8, 140.7, 133.9, 136.3, 136.7, 156.7 |
| Piperidine | CH$_2$: | 29.3, 51.5, 51.7, 29.3 |
|  | CH: | 43.7 |
|  | C: | 175.2 |
| Piperidine N-substituent | CH$_2$: | 30.9, 30.9, 46.2, 46.2, 45.2 |
|  | CH: | 36.5 |

Step C
1-(3-Bromo-8-chloro-6,11-dihydro-5H-benzo[5,6]cyclohepta[1,2-b]pyridin-11-yl)-N-[4-(N-carboxamidopiperidinyl)methyl]-4-piperidinecarboxamide 1-(3-Bromo-8-chloro-6,11-dihydro-5H-benzo[5,6]cyclohepta[1,2-b]pyridin-11-yl)-N-(4-piperidinylmethyl)-4-piperidinecarboxamide (0.005 g; 1 equivalent) (prepared as described in Step B above) is dissolved in anhydrous dichloromethane (0.161 ml). Trimethylsilylisocyanate (0.0038 ml; 3 equivalents) is added and the mixture is stirred at 25° C. under argon for 16 h. The mixture is diluted with dichloromethane and washed with saturated aqueous sodium bicarbonate. The dichloromethane layer is dried over magnesium sulfate, filtered and evaporated to dryness to give the title compound which is identical on thin layer chromatography (TLC) to that prepared in Procedure 2, Step C below.

Procedure 2
Step A
1-(3-Bromo-8-chloro-6,11-dihydro-5H-benzo[5,6]cyclohepta[1,2-b]pyridin-11-yl)-N-[4-(N-tert-butoxycarbonylpiperidine)methyl]-4-piperidinecarboxamide

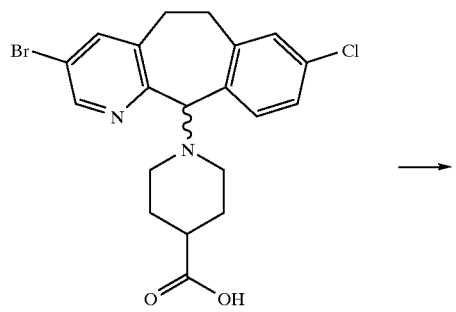

-continued

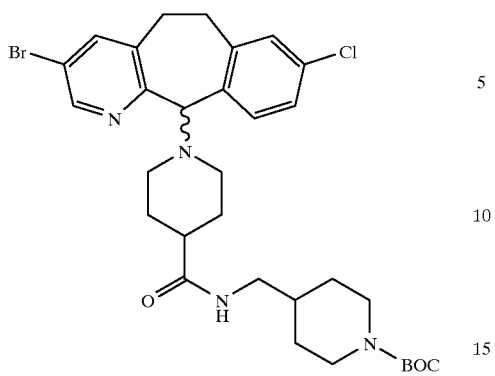

1-(3-Bromo-8-chloro-6,11-dihydro-5H-benzo[5,6]cyclohepta[1,2-b]pyridin-11-yl)-4-piperidinecarboxylate (0.5 g; 1 equivalent) (prepared as described in Preparative Example 2 below) dissolved in anhydrous DMF (18 ml) is added to a solution of 1-N-tert-butoxycarbonyl-4-aminomethylpiperidine (0.1778 g; 1 equivalent) (prepared as described in Preparative Example 3, Step C below), DEC (0.2067 g; 1.3 equivalents), HOBT (0.1457 g; 1.3 equivalents) and N-methylmorpholine (0.1 185 ml; 1.3 equivalents) in anhydrous DMF (8 ml) and the mixture is stirred at 25° C. for 19 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 0.75% (10% concentrated ammonium hydroxide in methanol)-dichloromethane as the eluant to give the title compound (0.4805 g; 71% yield), FABMS: m/z 631 (MH$^+$).

| | | $\delta_c$ (CDCl$_3$) |
|---|---|---|
| Tricyclic | CH$_2$: | 30.4, 30.3 |
| | CH: | 146.9, 141.2, 132.2, 126.1, 130.6, 79.5 |
| | C: | 119.8, 140.7, 133.9, 136.3, 136.7, 156.7 |
| Piperidine | CH$_2$: | 29.8, 51.7, 51.4, 29.3 |
| | CH: | 43.6 |
| | C: | 175.2 |
| Piperidine | CH$_3$: | 28.5 |
| N-substituent | CH$_2$: | 43.6, 43.6, 29.3, 29.3, 44.7 |
| | CH: | 36.4 |
| | C: | 79.5, 154.8 |

Step B 1-(3-Bromo-8-chloro-6,11-dihydro-5H-benzo[5,6]hepta[1,2-b]pyridin-11-yl)-N-(4-piperidinylmethyl)-4-piperidinecarboxamide

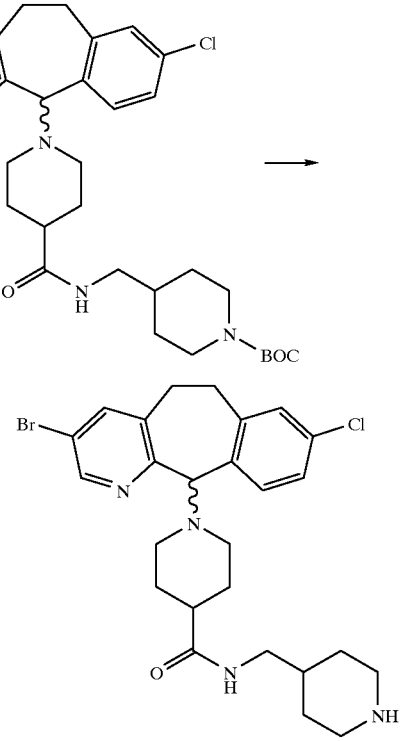

1-(3-Bromo-8-chloro-6,11-dihydro-5H-benzo[5,6]cyclohepta[1,2-b]pyridin-11-yl)-N-[4-(N-tert-butoxycarbonylpiperidine)methyl]-4-piperidine carboxamide (0.3936 g; 1 equivalent) is dissolved in anhydrous dichloromethane (30 ml). Trifluoroacetic acid (6.039 ml; 127 equivalents) is added to the stirred solution at 0° C. under argon. The mixture is stirred at 0° C. for 1.5 h and then allowed to warm to 25° C. for 1 h. The mixture is diluted with dichloromethane and washed with 1.0N sodium hydroxide. The dichloromethane layer is dried over magnesium sulfate, filtered and evaporated to dryness. The product is chromatographed on a silica gel column (60×2.5 cm) using 7% increasing to 10% (10% concentrated ammonium hydroxide in methanol)-dichloromethane as the eluant to give the title compound (0.2023 g; 61% yield), FABMS: m/z 531.1 (MH$^+$).

| | | $\delta_c$ (CDCl$_3$) |
|---|---|---|
| Tricyclic | CH$_2$: | 30.4, 30.3 |
| | CH: | 146.9, 141.2, 132.2, 126.1, 130.6, 79.5 |
| | C: | 119.8, 140.7, 133.9, 136.3, 136.7, 156.7 |
| Piperidine | CH$_2$: | 29.3, 51.4, 51.7, 29.3 |
| | CH: | 43.7 |
| | C: | 175.1 |
| Piperidine | CH$_2$: | 30.7, 30.7, 46.1, 46.1, 45.2 |
| N-substituent | CH: | 36.4 |

Step C 1-(3-Bromo-8-chloro-6,11-dihydro-5H-benzo[5,6]cyclohepta[1,2-b]pyridin-11-yl)-N-[4-(N-carboxamidopiperidinyl)methyl]-4-piperidinecarboxamide

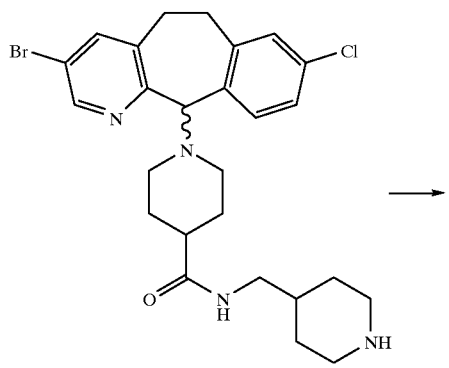

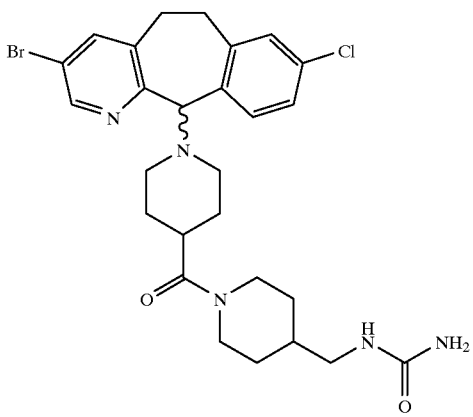

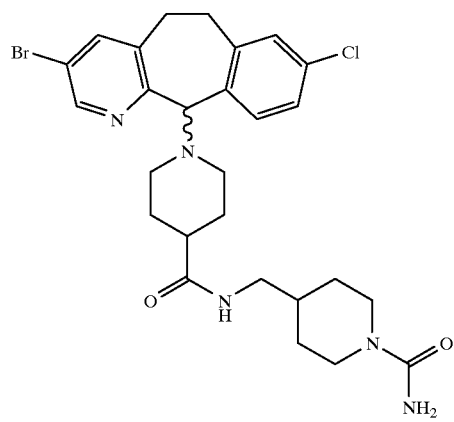

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (0.140 g; 1 equivalent) (prepared as described in Step B above) is dissolved in anhydrous dichloromethane (4.5 ml). Trimethylsilylisocyanate (0.534 ml) (15 equivalents) is added and the mixture is stirred at 25° C. under argon for 18 h. The mixture is diluted with dichloromethane and washed with saturated aqueous sodium bicarbonate. The dichloromethane layer is dried over magnesium sulfate, filtered and evaporated to dryness. The product is chromatographed on a silica gel column (30×2.5 cm) using 4% (10% concentrated ammonium hydroxide in methanol)-dichloromethane as the eluant to give the title compound (0.1084 g; 72% yield), FABMS: m/z 573.9 (MH+). FPT Inhibition=41% @ 1.04 μM.

|  |  | $\delta_c$ (CDCl$_3$) |
|---|---|---|
| Tricyclic | CH$_2$: | 30.4, 30.3 |
|  | CH: | 146.8, 141.2, 132.2, 126.1, 130.6, 79.5 |
|  | C: | 119.8, 140.7, 133.9, 136.3, 136.7, 156.7 |
| Piperidine | CH$_2$: | 29.3, 51.4, 51.7, 29.3 |
|  | CH: | 43.5 |
|  | C: | 175.4 |
| Piperidine N-substituent | CH$_2$: | 29.6, 29.6, 44.6, 44.6, 44.1 |
|  | CH: | 36.1 |
|  | C: | 158.1 |

EXAMPLE 9

1-[1-(3-Bromo-8-chloro-6,11-dihydro-5H-benzo[5,6]cyclohepta[1,2-b]pyridin-11-yl)-4-piperidinylcarbonyl]-4-[(1-aminomethanamido)methyl]piperidine Step A
1-[1-(3-Bromo-8-chloro-6,11-dihydro-5H-benzo[5,6]cyclohepta[1,2-b]pyridin-11-yl)-4-piperidinylcarbonyl]-4-[(N-tert-butoxycarbonylamino)methyl]piperidine

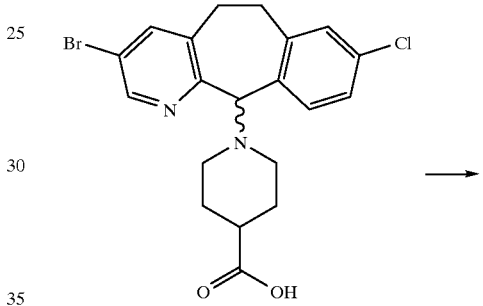

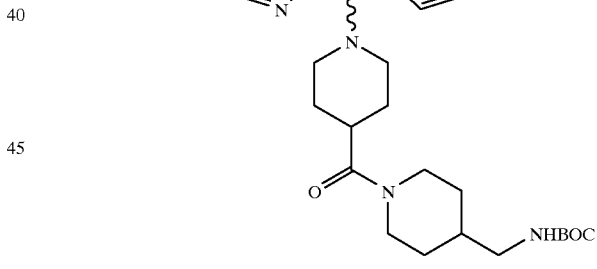

1-(3-Bromo-8-chloro-6,11-dihydro-5H-benzo[5,6]cyclohepta[1,2-b]pyridin-11-yl)-4-piperidinecarboxylate (0.3195 g; 1 equivalent) (prepared as described in Preparative Example 2 below) dissolved in anhydrous DMF (11.5 ml) is added to a solution of 4-[(N-tert-butoxycarbonylamino)-methyl]piperidine (0.1904 g; 1.3 equivalents) (prepared as described in Preparative Example 5, Step C below), DEC (0.1703 g; 1.3 equivalents), HOBT (0.1201 g; 1.3 equivalents) and N-methylmorpholine (0.195 ml; 2.6 equivalents) in anhydrous DMF and the mixture is stirred at 25° C. for 19 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 0.8% (10% concentrated ammonium hydroxide in methanol)-dichloromethane as the eluant to give the title compound (0.3701 g; 86% yield), FABMS: m/z 631.3 (MH⁺).

| | | δ$_c$ (CDCl$_3$) |
|---|---|---|
| Tricyclic | CH$_2$: | 30.7, 30.4 |
| | CH: | 146.8, 141.2, 132.2, 126.0, 130.6, 79.6 |
| | C: | 119.7, 140.7, 133.8, 136.4, 136.7, 156.9 |
| Piperidine | CH$_2$: | 51.6, 29.1, 28.9, 51.9 |
| | CH: | 38.8 |
| | C: | 173.4 |
| Piperidine N-substituent | CH$_3$: | 28.4 |
| | CH$_2$: | 45.3/45.9, 28.9/29.1, 29.5/30.2, 45.3/45.9, 41.7 |
| | CH: | 37.0 |
| | C: | 79.4, 156.1 |

Step B

1-[1-(3-Bromo-8-chloro-6,11-dihydro-5H-benzo[5,6]cyclohepta[1,2-b]pyridin-11-yl)-4-[piperidinyl]-4-aminomethylpiperidine

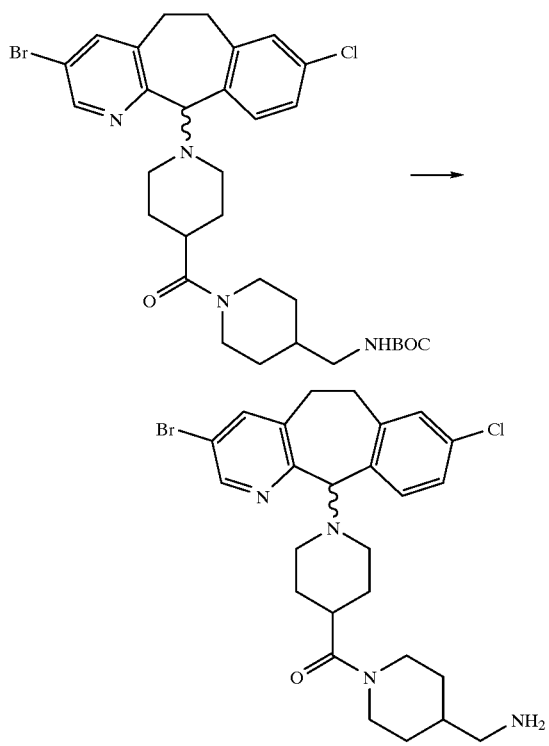

1-[1-(3-Bromo-8-chloro-6,11-dihydro-5H-benzo[5,6]cyclohepta[1,2-b]pyridin-11-yl)-4-piperidinylcarbonyl]-4-[(N-tert-butoxycarbonylamino)methyl]piperidine (0.35 g) (1 equivalent) is dissolved in methanol (3.1 ml). A 10% (v/v) solution of concentrated sulfuric acid in dioxane (7.568 ml) is added and the mixture is stirred at 25° C. under argon for 1.5 h. The mixture is stirred at 0° C. for 1.5 h and then allowed to warm to 25° C. for 1 h. The mixture is diluted with dichloromethane and washed with 1.0N sodium hydroxide. The dichloromethane layer is dried over magnesium sulfate, filtered and evaporated to dryness. The product is chromatographed on a silica gel column (30×2.5 cm) using 4% (10% concentrated ammonium hydroxide in methanol)-dichloromethane as the eluant to give the title compound (0.226 g; 77% yield), FABMS: m/z 531.4 (MH⁺). FPT Inhibition=16% @ 0.38 μM

| | | δ$_c$ (CDCl$_3$) |
|---|---|---|
| Tricyclic | CH$_2$: | 30.4, 30.2 |
| | CH: | 146.8, 141.2, 132.2, 126.0, 130.6, 79.6 |
| | C: | 119.8, 140.7, 133.8, 136.4, 136.7, 156.9 |
| Piperidine | CH$_2$: | 51.6, 29.1, 28.9, 51.9 |
| | CH: | 38.8 |
| | C: | 173.3 |
| Piperidine N-substituent | CH$_2$: | 42.0, 29.7/30.9, 29.0/29.2, 42.0, 45.5 |
| | CH: | 38.8 |

Step C

1-[1-(3-Bromo-8-chloro-6,11-dihydro-5H-benzo[5,6]cyclohepta[1,2-b]pyridin-11-yl)-4-piperidinylcarbonyl]-4-[(1-aminomethanamido)methyl]piperidine

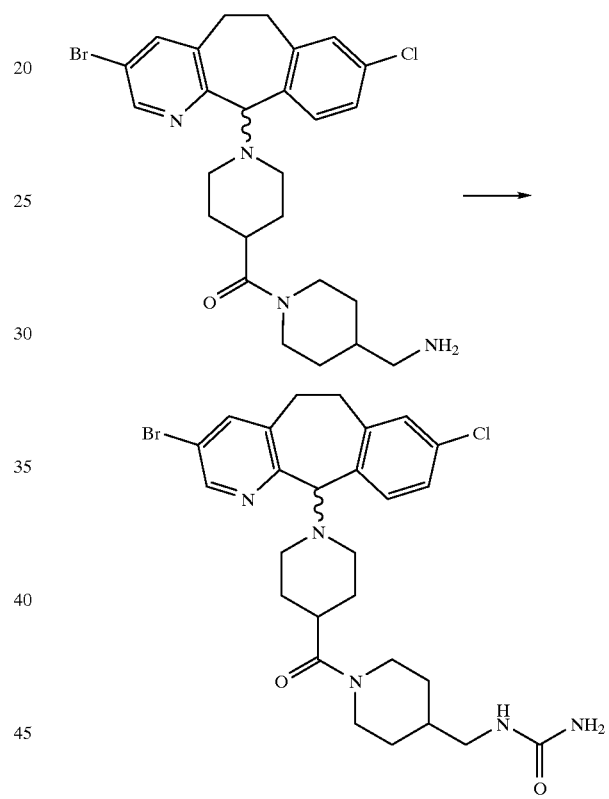

1-[1-(3-Bromo-8-chloro-6,11-dihydro-5H-benzo[5,6]cyclohepta[1,2-b]pyridin-11-yl)-4-piperidinylcarbonyl]-4-[(N-tert-butoxycarbonylamino)methyl]piperidine (0.185 g) (1 equivalent) (prepared as described in Example 9, Step B above) is dissolved in anhydrous dichloromethane (5 ml). Trimethylsilylisocyanate (0.706 ml) (15 equivalents) is added and the mixture is stirred at 25° C. under argon for 22 h. Additional trimethylsilylisocyanate (0.235 ml) (5 equivalents) is added and the stirring is continued for a total of 26.75 h. The mixture is diluted with dichloromethane and washed with saturated aqueous sodium bicarbonate. The dichloromethane layer is dried over magnesium sulfate, filtered and evaporated to dryness. The product is chromatographed on a silica gel column (30×2.5 cm) using 3.5% (10% concentrated ammonium hydroxide in methanol)-dichloromethane to give the title compound (0.1502 g; 75% yield), FABMS: m/z 574.2 (MH⁺).

FPT IC$_{50}$=0.66 μM

| | | δ$_c$ (CDCl$_3$) |
|---|---|---|
| Tricyclic | CH$_2$: | 30.4, 30.2 |
| | CH: | 146.8, 141.2, 132.2, 126.1, 130.6, 79.5 |
| | C: | 119.8, 140.7, 133.9, 136.2, 136.7, 156.7 |
| Piperidine | CH$_2$: | 51.5, 29.0, 28.9, 51.8 |
| | CH: | 38.8 |
| | C: | 173.6 |
| Piperidine N-substituent | CH$_2$: | 41.9, 41.9, 30.7, 29.6, 45.4 |
| | CH: | 36.9 |
| | C: | 159.2 |

EXAMPLE 10
1-(8-chloro-3-bromo-5,6-dihydro-11H-benzo[5,6]-cyclohepta[1,2-b]pyridin-11-yl)piperidine-3-(N-3-pyridylmethylamino)carboxamide

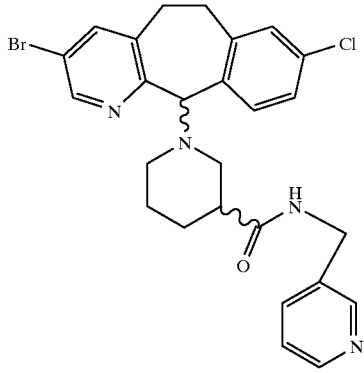

Procedure 1
Step A
Ethyl 1-(3-bromo-8-chloro-6,11-dihydro-5H-benzo[5,6]cyclohepta[1,2-b]pyridin-11-yl)-3-piperidinecarboxylate

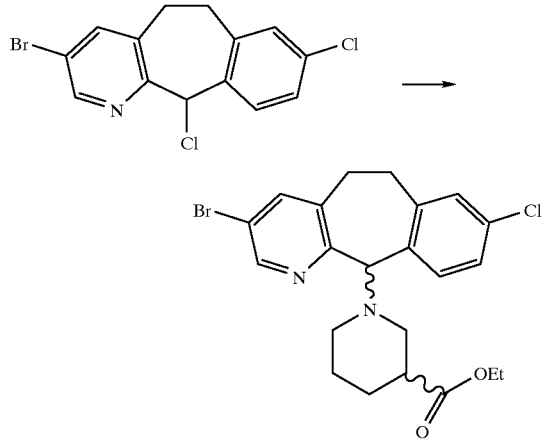

3-Bromo-8,11-dichloro-6,11-dihydro-5H-benzo[5,6]cyclohepta[1,2-b]pyridine (1 g, 2.5 mmol) is dissolved in 10 mL of N,N-dimethylformamide (DMF). Ethylnipecotate (0.6 ml, 3.7 mmol) and N-methylmorpholine (0.69 mL, 6.2 mmol) are added and the reaction mixture is stirred at ambient temperature for 18 hours. The reaction mixture is poured into water and extracted with dichloromethane two times. The combined extracts are dried over magnesium sulfate and the mixture filtered and evaporated to obtain an oil. The oil is chromatographed on silica gel using 10% ethyl acetate/hexanes as the eluent to obtain 0.55 gm of the title compound. FABMS (MH$^+$)=464

Step B
1-(3-Bromo-8-chloro-6,11-dihydro-5H-benzo[5,6]cyclohepta[1,2-b]pyridin-11-yl)-3-piperidinecarboxylate

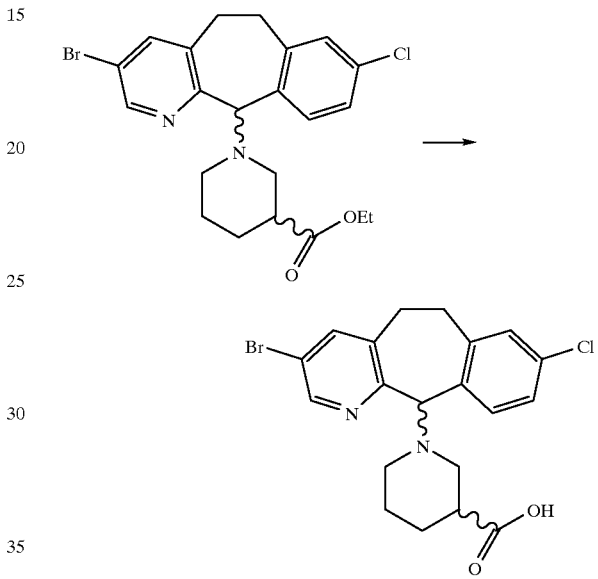

Ethyl 1-(3-bromo-8-chloro-6,11-dihydro-5H-benzo[5,6]cyclohepta[1,2-b]pyridin-11-yl)-3-piperidinecarboxylate (1.9 gm) is refluxed in 25 ml of 6N hydrochloric acid for 8 hours. The HCl and water is evaporated to obtain the title compound, as a solid.

Step C
1-(3-Bromo-8-chloro-6,11-dihydro-5H-benzo[5,6]cyclohepta[1,2-b]pyridin-11-yl)-N-(3-pyridinylmethyl)-3-piperidinecarboxamide

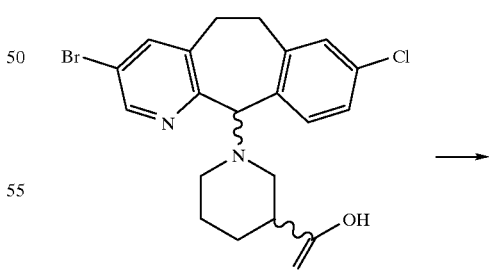

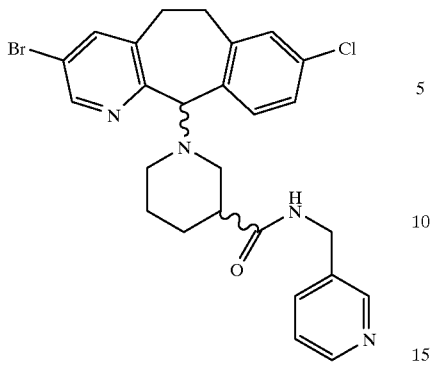

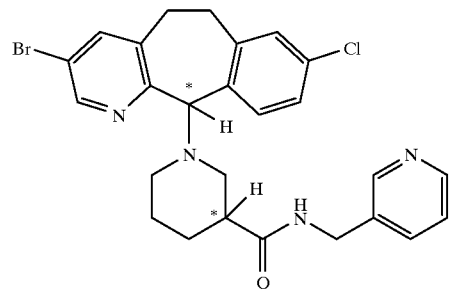

FABMS(MH+) = 526.8
FPT IC$_{50}$ = 0.194 μM

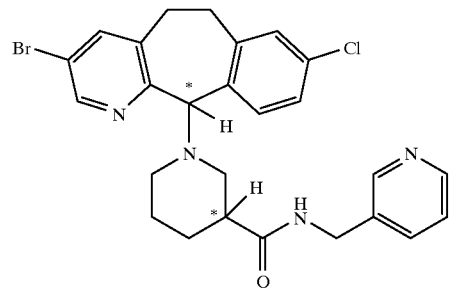

FABMS(MH+) = 526.8
FPT IC$_{50}$ = 0.179 μM

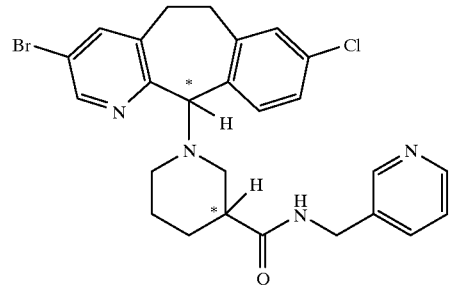

FABMS(MH+) = 526.8
FPT IC$_{50}$ = 0.187 μM

The compound from Example 10, Step B is dissolved in 12 mL of DMF and 1-(3-dimethylaminopropyl)-3-ethylcarbodiimide hydrochloride (DEC) (0.37 g 1.9 mmol), 1-hydroxybenzotriazole (HOBT) (0.36 g), NMM (0.5 mL) and (0.216 g, 2.0 mmol) of 3-aminomethylpyridine are added and the reaction mixture is stirred at ambient temperature. After 17 hours the reaction mixture is poured into water and extracted with dichloromethane two times. The combined extracts are dried over magnesium sulfate and the mixture filtered and evaporated to obtain an oil. The oil is chromatographed on silica gel using 5% methanol/dichloromethane as the eluent to obtain 0.44 gm of the title compound.

FABMS (MH+)=603
FPT IC$_{50}$=0.21 μM

Step D
Separation of Isomers

The compound of Example 10, Procedure 1, Step C, is separated into its four optical isomers by HPLC chromatography with a Chiralpak® AD analytical (0.46 cm×25 cm) chiral column (amylose tris(3,5-dimethylphenyl carbamate) coated on a 10 μM silica-gel substrate (trademark of of Chiral Technologies, Exton, Pa.), using as the eluting solvent, 20% isopropanlol/hexanes/0.02% diethylamine at 1 mL/minute, the four compounds elute at 10.27 (Isomer A), 11.43 (Isomer B), 11.57 (Isomer C) and 18.37 (Isomer D) minutes.

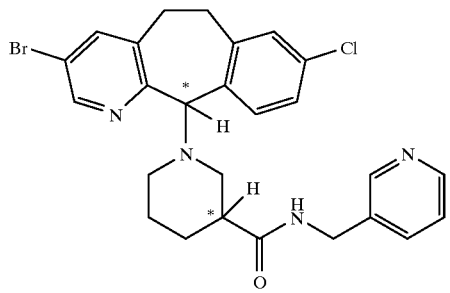

FABMS(MH+) = 526.8
FPT Inhibition = 6.1% @ 1.14 μM

Procedure 2

Step A

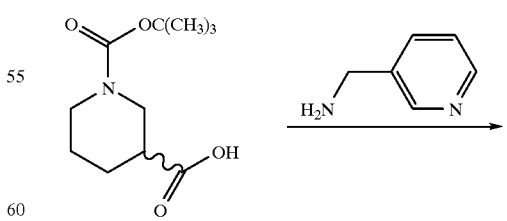

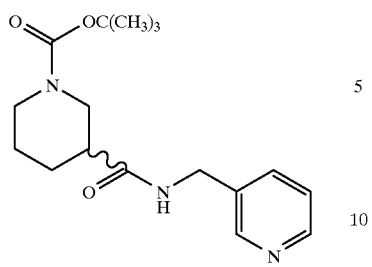

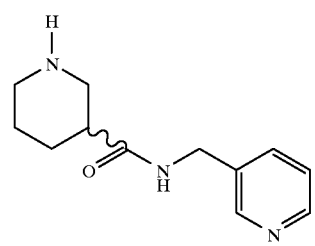

To a solution of N-(tert-butoxycarbonyl)nipecotic acid (0.50 g, 2.41 mmol) in dichloromethane (10 mL) is added 3-(aminomethyl)pyridine (0.27 mL, 2.65 mmol), 1-hydroxybenzotriazole monohydrate (HOBT) and 1,3-dicyclohexylcarbodiimide (0.547 g, 2.65 mmol). The mixture is stirred at room temperature for 16 hr and is then filtered. The solution is purified by flash chromatography (SiO$_2$, 2% methanol in CH$_2$Cl$_2$) affording 0.67 g of the product.

A solution of the product of Example 10, Procedure 2, Step A, (0.04 g, 0.125 mmol) in CH$_2$Cl$_2$ (3 mL) is treated with trifluoroacetic acid (TFA) (0.5 mL) for 1 hr. The mixture is then evaporated to dryness in vacuo and azeotroped with methanol (3×5 mL portions).

Step C

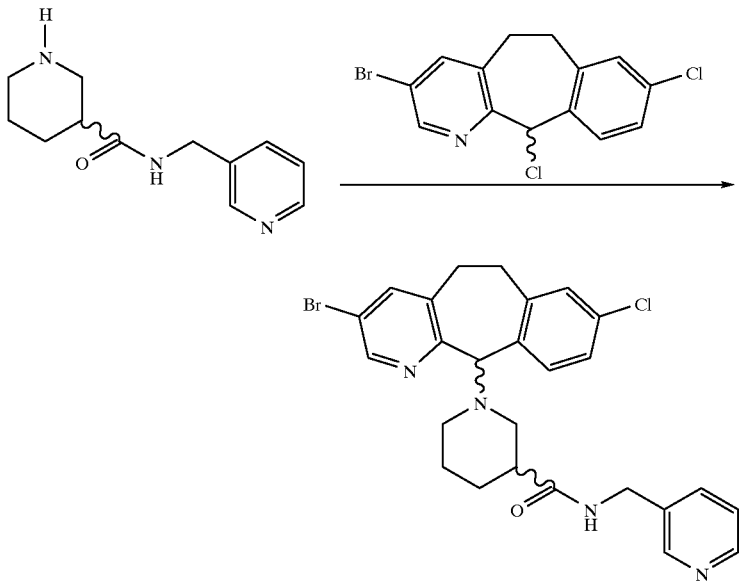

Step B

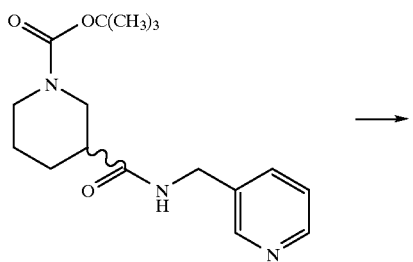

The residue from Example 10, Procedure 2, Step B above, is then dissolved in CH$_3$CN (1 mL) and a solution of 3-bromo-8,11-dichloro-6,11-dihydro-5H-benzo[5,6]cyclohepta[1,2-b]pyridine (0.07 g, 0.2 mmol) in CH$_3$CN is added, followed by 1,2,2,6,6-pentamethylpiperidine (0.2 mL, 1.1 mmol). The solution is heated at 45° C. for 16 hr and then evaporated to dryness in vacuo. The residue is purified by flash chromatography (SiO$_2$, 3% methanol in CH$_2$Cl$_2$) affording 0.04 g of the title compound.

1H NMR (300 Mhz) CDCl3; d=1.45–1.75 (m, 2H); 1.8–1.92 (m, 1H); 2.02–2.15 (m, 1H); 2.16–2.30 (m, 1H); 2.38–2.52 (m, 2H); 2.58–2.72 (m, 2H); 3.16–3.3 (m, 1H); 3.46–3.70 (m, 2H); 3.70–3.82 (m, 1H); 4.32 (br. s, 2H); 4.39 (d, 1H); 4.45–4.52 (m, 1H); 6.93 (br. s, 0.5H); 7.06–7.17 (m, 3H); 7.22–7.28 (m, 1H); 7.35 (br. s, 0.5H); 7.45–7.52 (m, 1H); 7.53 (d, 0.5H); 8.38 (d, 0.5H); 8.49 (br. s, 1H); 1.58 (m, 1H).

EXAMPLE 11

1-(3-bromo-8-chloro-6,11-dihydro-5H-benzo[5,6]cyclohepta[1,2-b]pyridin-11-yl)-N-(3-pyridinyl)-3-piperidinecarboxamide

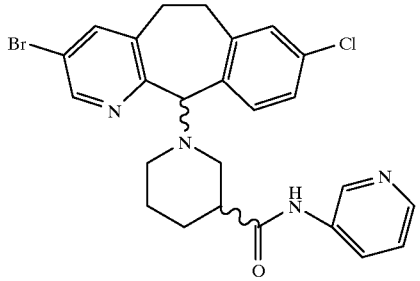

1-(3-Bromo-8-chloro-6,11-dihydro-5H-benzo[5,6]cyclohepta[1,2-b]pyridin-11-yl)-3-piperidinecarboxylate (0.12 gm, 0.27 mmol) from Example 10, Procedure 1, Step B, is dissolved in 4 ml of DMF. 1-(3-Dimethylaminopropyl)-3-ethyl carbodiimide hydrochloride (DEC), (79 mg, 0.41 mmol), 1-hydroxybenzotriazole (HOBT) (55 mg, 0.41 mmol), N-methyl morpholine (NMM) (0.29 ml, 2.7 mmol), and 3-amino pyridine (0.05 gm) are added and the reaction mixture is stirred for 18 hours. The reaction mixture is poured into water and extracted with ethyl acetate three times. The combined extracts are dried over magnesium sulfate, filtered and chromatographed on silica gel to obtain 42 mg of title compound. FABMS (MH$^+$)=512.8

FPT IC$_{50}$=0.065 $\mu$M

EXAMPLE 12

1-(3-Bromo-8-chloro-6,11-dihydro-5H-benzo[5,6]cyclohepta[1,2-b]pyridin-11-yl)-N-(4-pyridinylmethyl)-2S-piperidinecarboxamide—Isomer A1 amide

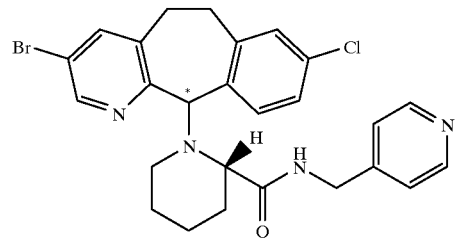

Step A1
L-Pipecolinic Acid Ethyl Ester Hydrochloride

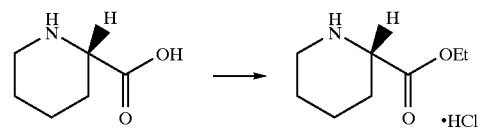

L-Pipecolinic acid (0.9 g, 6.97 mmol) is dissolved in 40 mL of absolute EtOH. HCl gas is bubbled for ~1 minute. The reaction mixture is refluxed for 20 min, cooled and the solvents removed by rotary evaporation to give 1.34 g of the title compound, a wax that is used without further purification.

Step A2
D-Pipecolinic Acid Ethyl Ester Hydrochloride

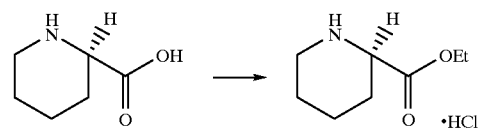

Using essentially the same conditions as described in Example 12, Step A1, but replacing L-Pipecolinic acid with D-Pipecolinic acid, the title compound is obtained.

Step B

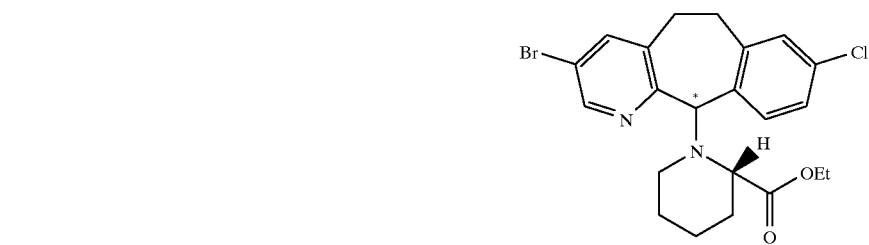

Isomer A1 ester

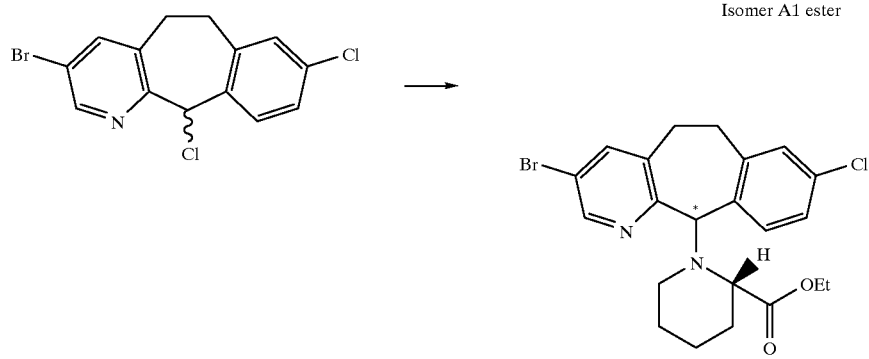

Isomer B1 ester

3-Bromo-8,11-dichloro-6,11-dihydro-5H-benzo[5,6]cyclohepta[1,2-b]pyridine (1.10 g, 3.00 mmol) and L-pipecolinic acid ethyl ester hydrochloride from Example 12, Step A1 (1.34 g, 6.98 mmol), triethylamine (2.91 μL, 21 mmol) are dissolved in dry $CH_2Cl_2$ (20 ml) and the mixture is stirred at 25° C. under nitrogen for 72 h. The reaction mixture is washed with saturated $NaHCO_3$, $H_2O$, brine and then filtered through $Na2SO_4$ and evaporated to dryness. The product is chromatographed on a silica gel column using 1% ethyl acetate-dichloromethane as the eluant to separate the two separable diastereomeric isomers (i.e. Isomers A1 ester and B1 ester), the less polar being referred to as Isomer A1 ester and the more polar isomer being referred to as Isomer B1 ester. FABMS $MH^+$=464.

Step C

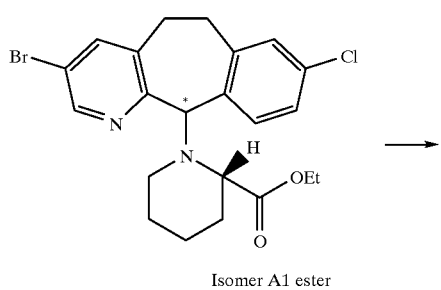

Isomer A1 ester

-continued

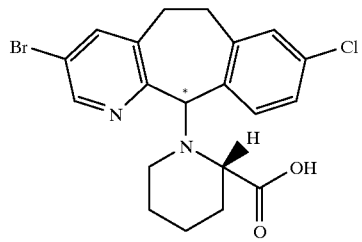

Isomer A1 acid

Isomer A1 ester from Example 12, Step B (0.26 g, 0.6 mmol) is dissolved in 6 mL of ethanol and 1.4 mL of 1M LiOH (1.4 mmol) is added. The reaction mixture is heated on oil bath at 80° C. for 10 h, cooled and 1.5 mL of 1N HCl is then added to adjust the pH to ~4.5. Solvents are then removed by evaporation and the resulting crude acid is used in the next reaction without further purification.

Step D

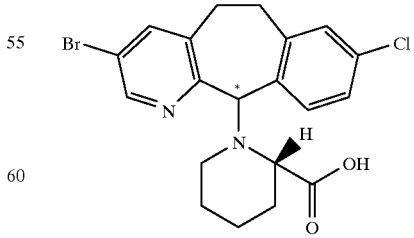

Isomer A1 acid

-continued

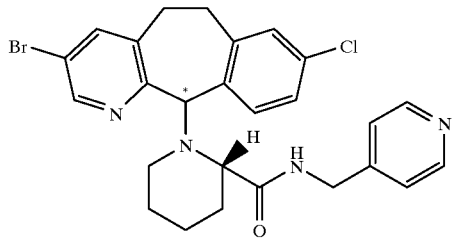

Isomer A1 amide

Isomer A1 acid from Example 12, Step C (from 0.26 g, 0.6 mmol of Isomer A ester) is dissolved in 3 mL of DMF and NMM (184 µL, 1.6 mmol), 4-(aminomethyl)pyridine (74 µL, 0.078 g, 0.73 mmol), HOBT(0.098 g, 0.72 mmol), DEC(0.139 g, 0.72 mmol) are then added. The reaction mixture is stirred at room temperature for 16 h. DMF is removed by rotary evaporation and the resulting crude mixture is partitioned between EtOAc-NaHCO$_3$. The organic phase is washed with H$_2$O, brine and filtered though Na$_2$SO$_4$ to give crude product that is purified by flash chromatography eluting with 3% (10% NH$_4$OH—CH$_3$OH)—CH$_2$Cl$_2$ solvent system to obtain the title compound, a white solid FAB-MS MH$^+$=527

FPT Inhibition=18% @ 1.1 µM

EXAMPLE 13

1-(3-Bromo-8-chloro-6,11-dihydro-5H-benzo[5,6]cyclohepta[1,2-b]pyridin-11-yl)-N-(4-pyridinylmethyl)-2S-piperidinecarboxamide—Isomer B1 amide

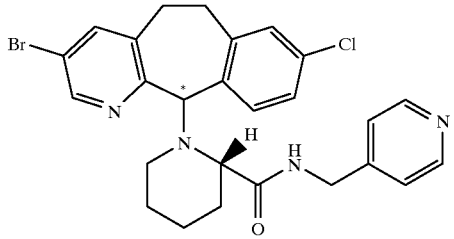

Isomer B1 amide

Using the method of Example 12, Steps C and D, except that Isomer B1 ester from Example 12, Step B, is used instead of Isomer A1 ester, the title compound is obtained. MH$^+$=527

FPT Inhibition =21% @ 1.1 µM

EXAMPLE 14

Using the method of Examples 12 and 13, except that D-pipecolinic acid ethyl ester hydrochloride is used in place of L-pipecolinic acid ethyl ester hydrochloride, the following two diasteriomers are obtained:

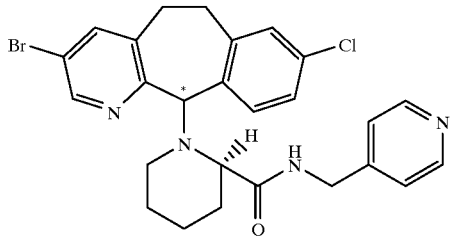

Isomer A2 amide

MH$^+$ = 527
FPT Inhibition = 0% @ 1.1 µM

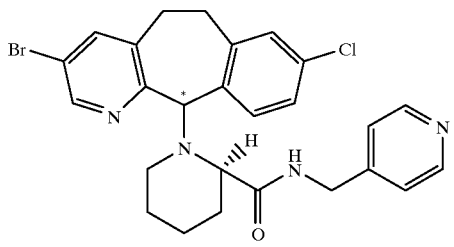

Isomer B2 amide

MH$^+$ = 527
FPT Inhibition = 13% @ 1.1 µM

EXAMPLE 15

Using the method of Examples 12–14, except that in Example 12, Step D, 3-(aminomethyl)pyridine is used in place of 4-(aminomethyl)pyridine, the following four diasteriomers are prepared.

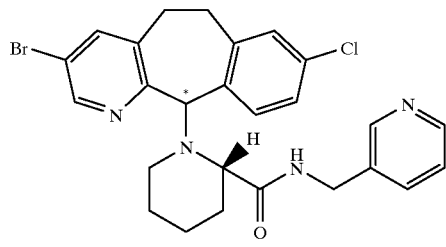

Isomer C1 amide

MH$^+$ = 527
melting point (m.p.) = 198.5–199° C.
FPT IC$_{50}$ = 0.3 µM

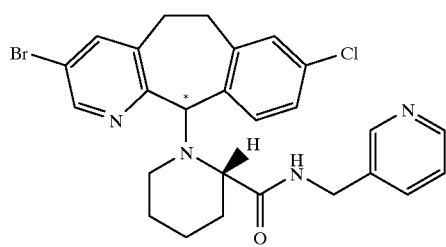

Isomer D1 amide

MH$^+$ = 527
m.p. = 180.9–181.5°C.
FPT IC$_{50}$ = 0.16 µM

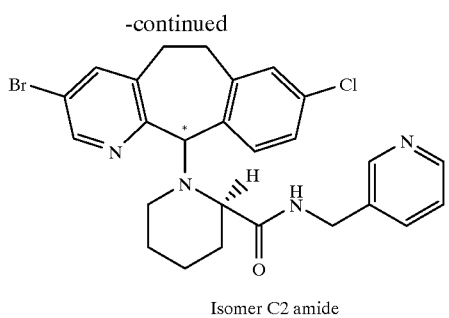

Isomer C2 amide

MH+ = 527
m.p. = 168.2–168.4°C.
FPT Inhibition = 11% @ 0.38 μM

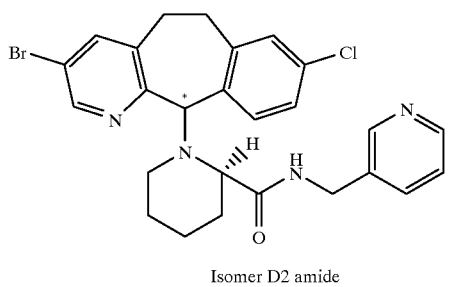

Isomer D2 amide

MH+ = 527
m.p. = 205.5–206.4°C.
FPT Inhibition = 0% @ 0.38 μM

EXAMPLE 16
1-(3,10-Dibromo-8-chloro-6,11-dihydro-5H-benzo[5,6]cyclohepta[1,2-b]pyridin-11-yl)-N-(3-pyridinylmethyl)-3-piperidinecarboxamide

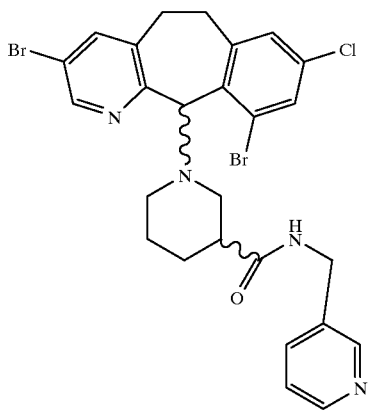

Using the method of Example 10, Procedure 1, except that the compound 3,10-dibromo-8,11-dichloro-6,11-dihydro-5H-benzo[5,6]cyclohepta[1,2-b]pyridine is substituted for 3-bromo-8,11-dichloro-6,11-dihydro-5H-benzo[5,6]cyclohepta[1,2-b]pyridine, the title compound is obtained. FABMS MH+=605.7

FPT IC$_{50}$=0.027 μM

EXAMPLE 17
1-(3,10-Dibromo-8-chloro-6,11-dihydro-5H-benzo[5,6]cyclohepta[1,2-b]pyridin-11-yl)-N-(3-pyridinylmethyl)-3-piperidinecarboxamide Using the method of Example 10, Procedure 1, except that the compound 3,10-dibromo-8,11-dichloro-6,11-dihydro-5H-benzo[5,6]cyclohepta[1,2-b]pyridine is substituted for 3-bromo-8,11-dichloro-6,11-dihydro-5H-benzo[5,6]cyclohepta[1,2-b]pyridine and optically pure ethylnipecotate is used, the title compound is obtained. Optically pure ethyinipecotate can be prepared from L-tartaric acid according to (Recl. Trav. Chim. P. 899, 1951).

Separation of the resulting two isomers by HPLC chromatography is performed on a Chiral Techniogies AD analytical (0.46 cm×25 cm) chiral column using 10% isopropanol/hexanes/0.02% diethylamine at 1 mL/minute. The two compounds are eluted at 14.85 (Isomer A) and 24.7 (Isomer B) minutes.

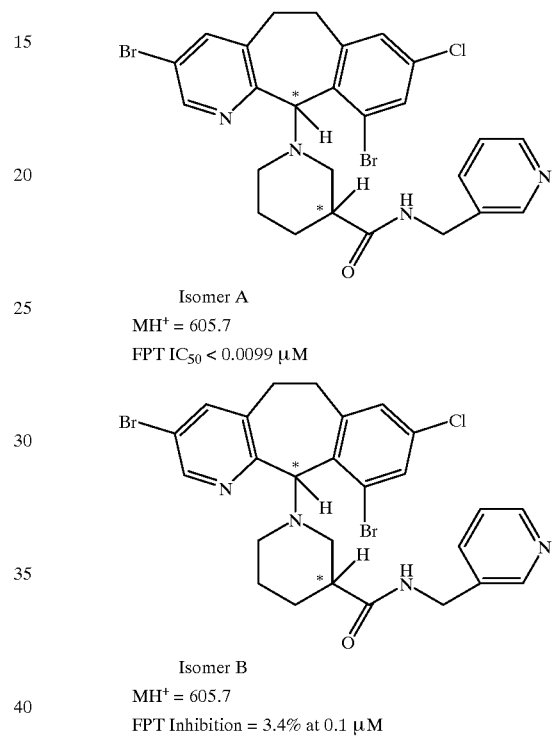

Isomer A
MH+ = 605.7
FPT IC$_{50}$ < 0.0099 μM

Isomer B
MH+ = 605.7
FPT Inhibition = 3.4% at 0.1 μM

EXAMPLE 18
1-(3-Bromo-8-chloro-6,11-dihydro-5H-benzo[5,6]cyclohepta[1,2-b]pyridin-11-yl)-N-(3-pyridinylmethyl)-3-piperidineacetamide

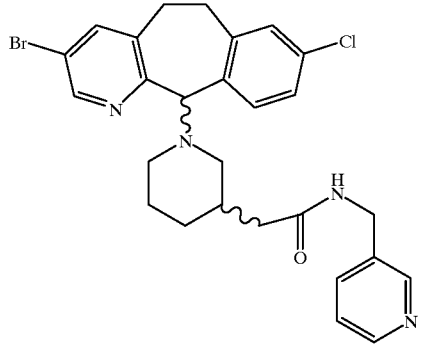

Using the method of Example 10, Procedure 1, except that 3-ethylpiperidineacetate is substituted for ethylnipecotate, the title compound is obtained. FABMS(MH+)=541.0

FPT Inhibition=9% @ 1.1 μM

EXAMPLE 19
1-(3-Bromo-8-chloro-6,11-dihydro-5H-benzo[5,6]cyclohepta[1,2-b]pyridin-11-yl)-N-(3-pyridinyl)-3-piperidineacetamide

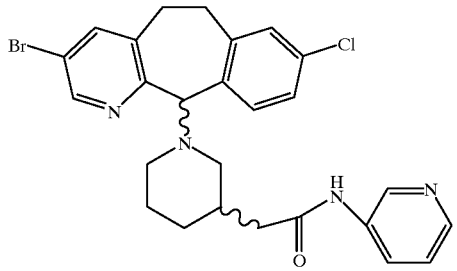

Using the method of Example 10, Procedure 1, except that 3-ethylpiperidineacetate is substituted for ethylnipecotate, and Example 11, except that nicotinic acid is substituted for 3-pyridylacetic acid, the title compound is obtained.
FABMS(MH+)=526.9
FPT Inhibition=15% @ 1.1 μM

EXAMPLE 20

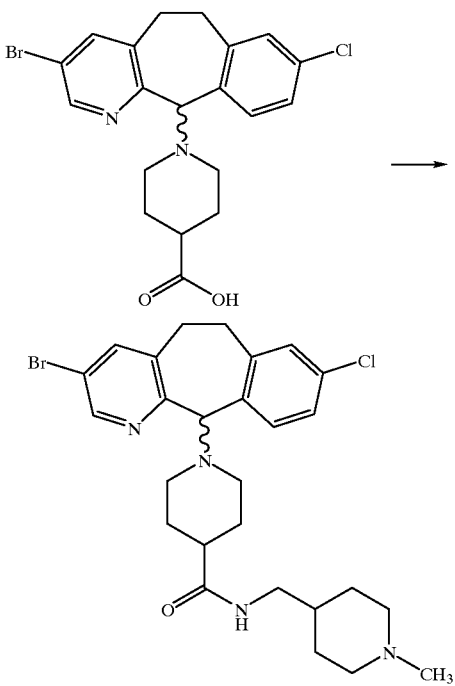

1-(3-Bromo-8-chloro-6,11-dihydro-5H-benzo[5,6]cyclohepta[1,2-b]pyridin-11-yl)-4-piperidinecarboxylate (1 equivalent) (prepared as described in Preparative Example 2) is reacted with 1-N-methyl-4-(aminomethyl)piperidine (1.3 equivalents) (prepared by reductive formylation of 4-ethoxycarbonylaminomethylpyridine, followed by hydrolysis of the protecting group under standard conditions) under similar conditions to those described in Preparative Example 2, below, to give the title compound.

EXAMPLE 21

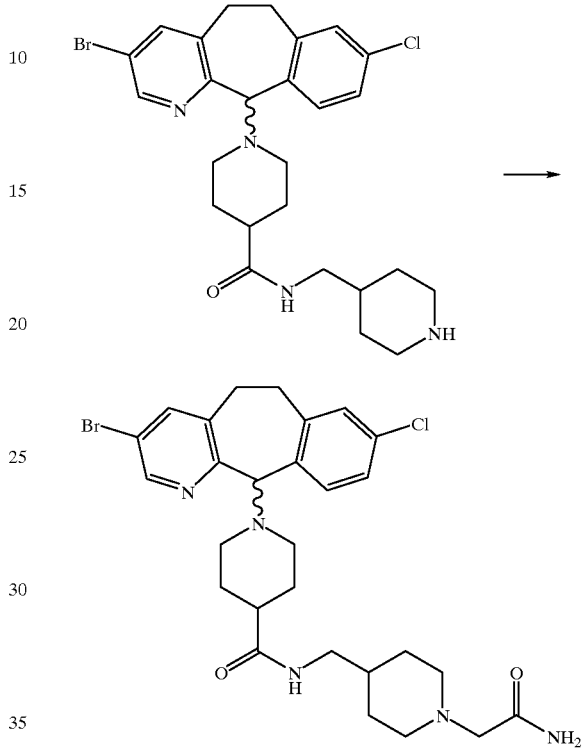

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) is reacted with 2-bromoacetamide (1.1 equivalents) and sodium carbonate in anhydrous DMF at 25° C. to give the title compound.

EXAMPLE 22

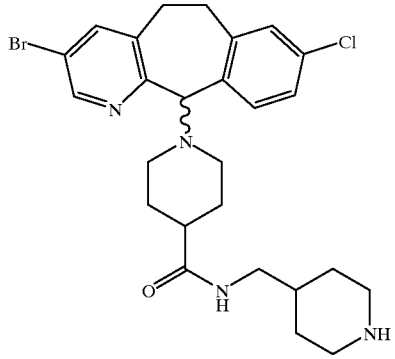

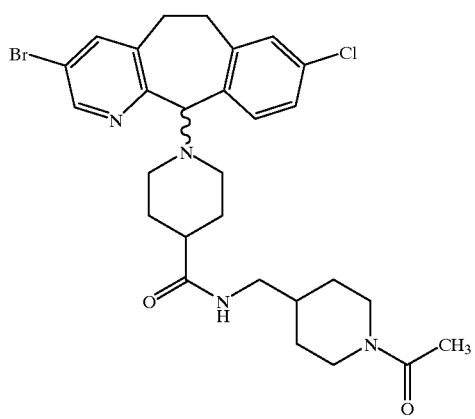

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) is reacted with an excess of acetic anhydride in methanol at 25° C. for 24 h to give the title compound.

EXAMPLE 23

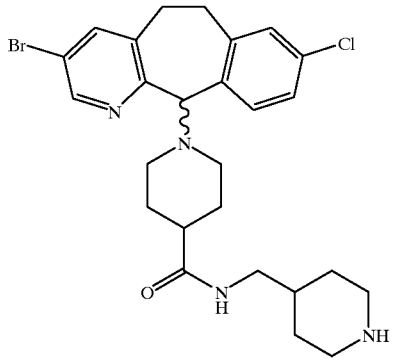

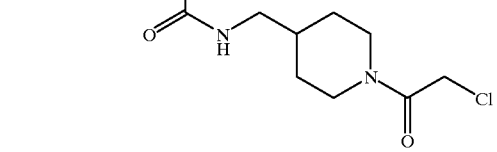

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) is reacted with chloroacetyl chloride (1.1 equivalents) and triethylamine (2 equivalents) in dichloromethane to give the intermediate chloroacetate. The latter is reacted with an excess of dimethylamine in the presence of sodium carbonate in DMF at 25° C. to give the title compound.

EXAMPLE 24

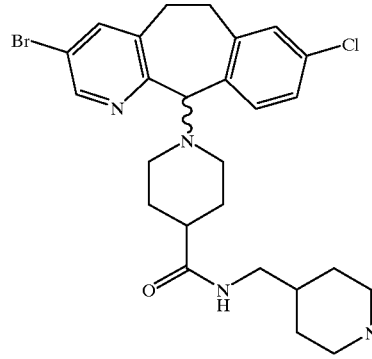

53
-continued

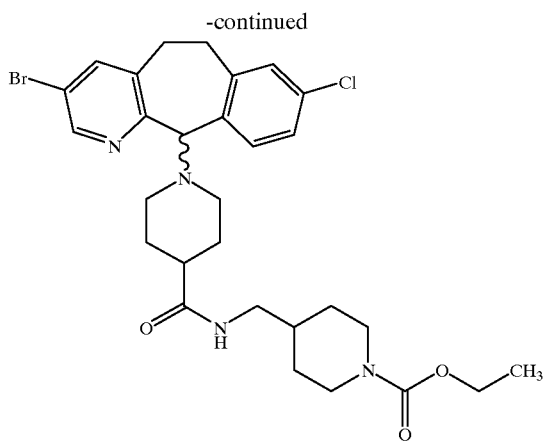

54
-continued

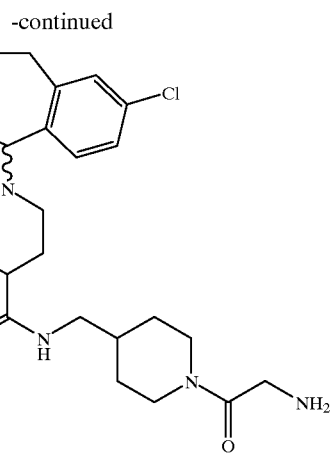

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) is reacted with ethylchloroformate (1.1 equivalents) in anhydrous dichloromethane at 25° C. for 24 h to give the title compound.

EXAMPLE 25

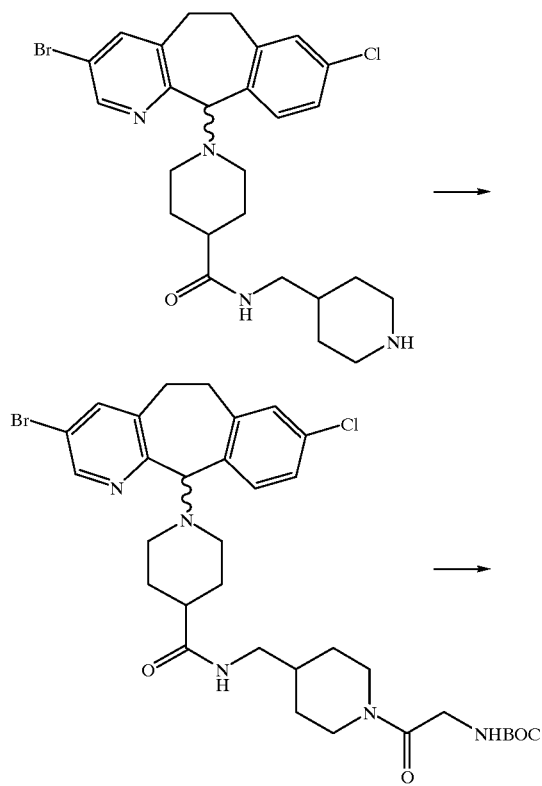

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) is reacted with N-(tert-butoxycarbonyl)glycine (1.3 equivalents), DEC.HCl (1.3 equivalents), HOBT (1.3 equivalents) and N-methylmorpholine (1.3 equivalents) in anhydrous DMF at 25° C. for 24 h to give the N-BOC intermediate. The latter is dissolved in methanol and reacted with 10% concentrated sulfuric acid in dioxane at 25° C. for 2 h to give after basification and chromatography on silica gel, the title compound.

EXAMPLE 26

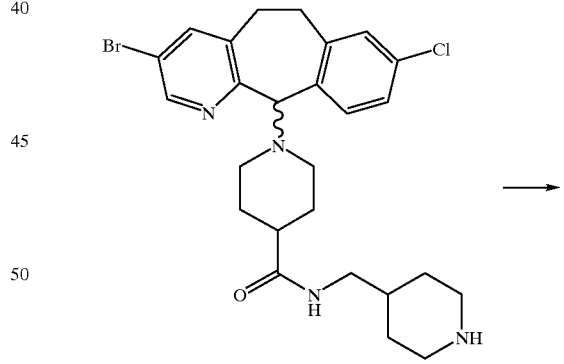

-continued

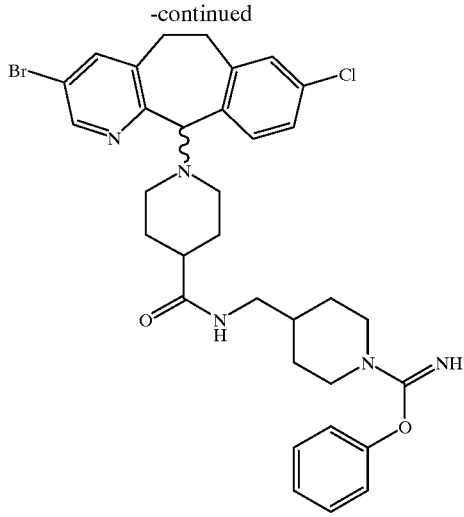

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) in dichloromethane is reacted with phenyl cyanate (2 equivalents) and diisopropylethylamine at 25° C. for 15 minutes to give the title compound.

EXAMPLE 27

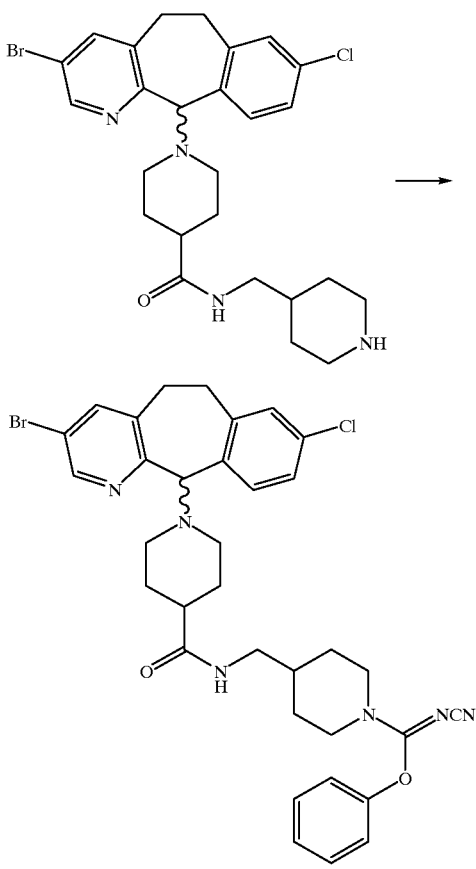

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) and diphenylcyanocarbonimidate (1.2 equivalents) are dissolved in 2-propanol and the mixture is heated at 80° C. for 24 h to give the title compound.

EXAMPLE 28

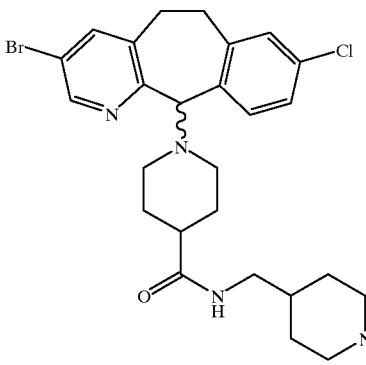

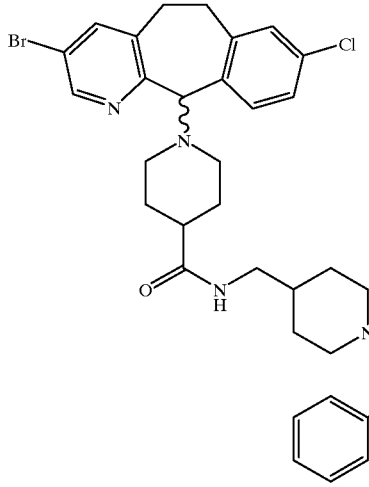

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) and diphenylsulfamoylcarbonimidate (1.2 equivalents) [prepared as described in: M. Haake and B. Schummelfeder, Synthesis, 753–758 (1991)] are dissolved in 2-propanol and the mixture is heated at 80° C. for 24 h to give the title compound.

EXAMPLE 29

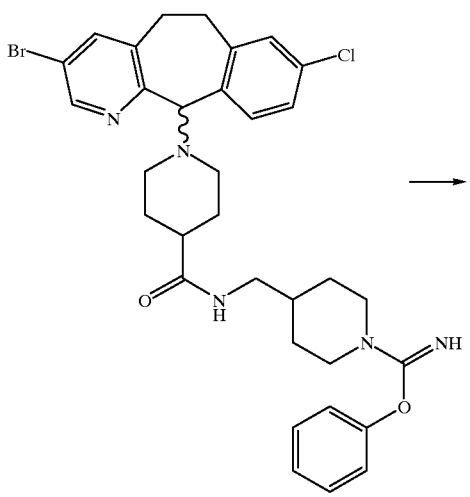

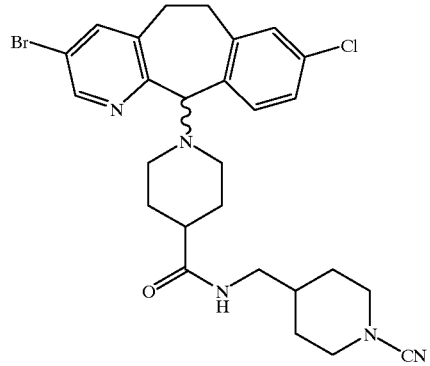

The phenoxyimidate (1 equivalent) (prepared as described in Example 26 above) is dissolved in anhydrous THF. A 60% sodium hydride dispersion in oil 4 equivalents) is added and the mixture is stirred at 25° C. for 2 h. The mixture is diluted with dichloromethane and washed with 1N sodium hydroxide. Chromatography on silica gel affords the title compound.

EXAMPLE 30

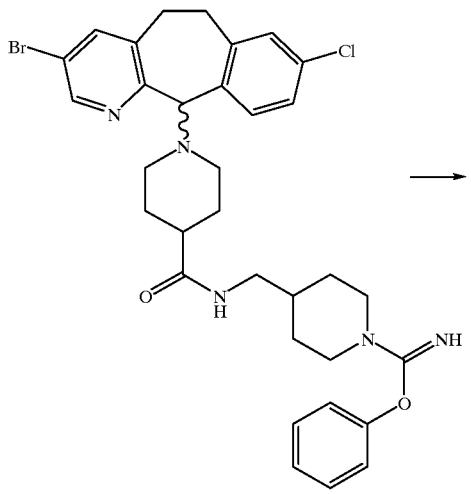

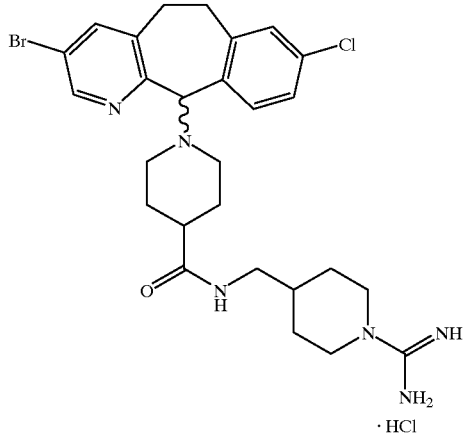

The phenoxyimidate (1 equivalent) (prepared as described in Example 26 above) is dissolved in concentrated ammonium hydroxide and ammonium chloride (1 equivalent) is added. The mixture is heated in a sealed tube at 90° C. to give the title compound.

EXAMPLE 31

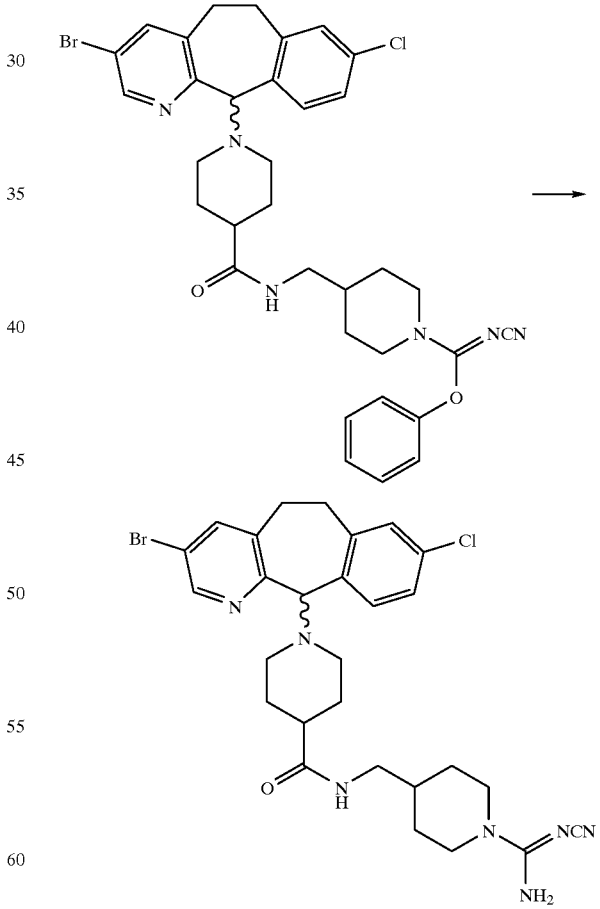

The N-cyanophenoxyimidate (1 equivalent) (prepared as described in Example 27 above) is dissolved in concentrated ammonium hydroxide and the mixture is stirred at 25° C. for 24 h to give the title compound.

EXAMPLE 32

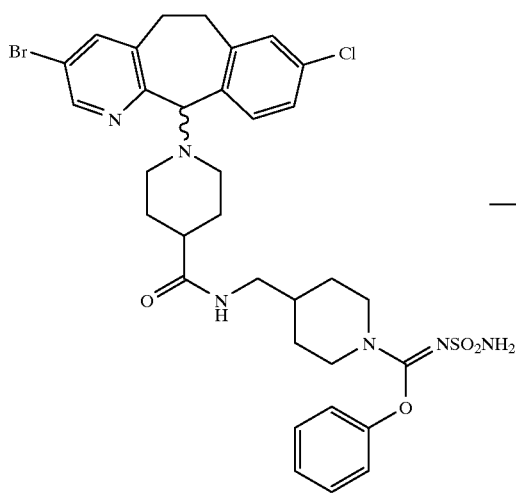

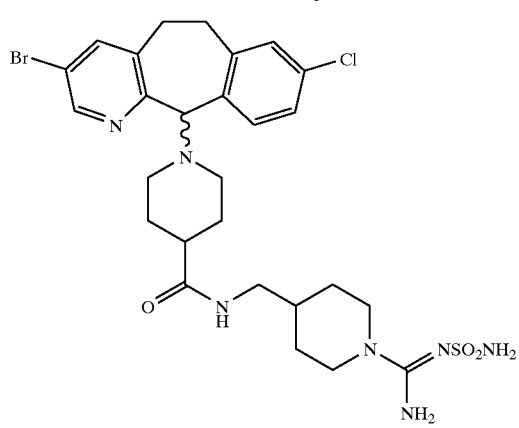

The N-sulfamoylphenoxyimidate (1 equivalent) (prepared as described in Example 28 above) is dissolved in concentrated ammonium hydroxide and the mixture is stirred at 25° C. for 24 h to give the title compound.

EXAMPLE 33

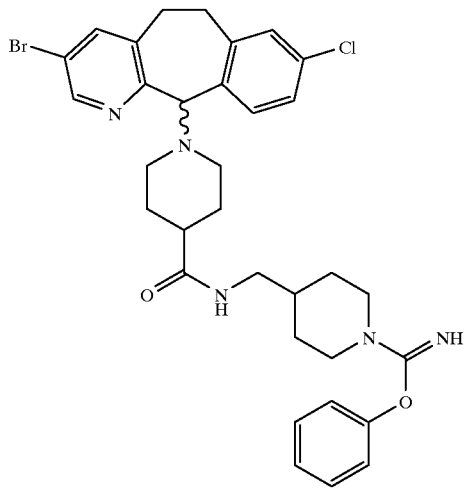

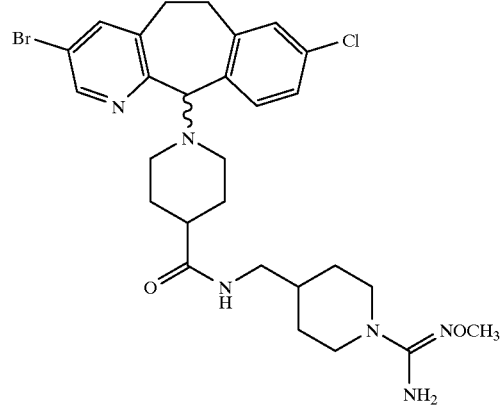

The phenoxyimidate (1 equivalent) (prepared as described in Example 26 above) is dissolved in methanol. An aqueous solution of methoxylamine (1 equivalent) [prepared by dissolving methoxylamine hydrochloride (1 equivalent) in 50% (w/v) sodium hydroxide (1 equivalent)] is added and the mixture is stirred at 25° C. to give the title compound.

EXAMPLE 34

Using the method of Example 14 except that 3,10-dibromo-8,11-dichloro-6,11-dihydro-5H-benzo[5,6]cyclohepta[1,2-b]pyridine is substituted for 3-bromo-8,11-dichloro-6,11-dihydro-5H benzo[5,6]cyclohepta[1,2-b]pyridine, the following two compounds are obtained:

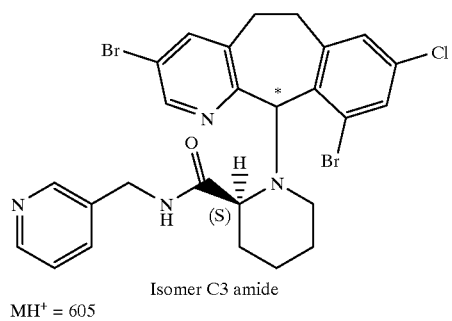

Isomer C3 amide
MH$^+$ = 605
FPT IC$_{50}$ = 0.3 μM

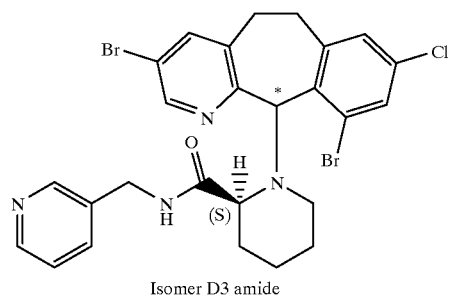

Isomer D3 amide
MH$^+$ = 605
FPT IC$_{50}$ = 0.0.0042 μM

EXAMPLE 35

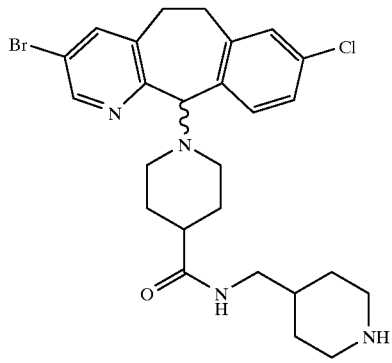

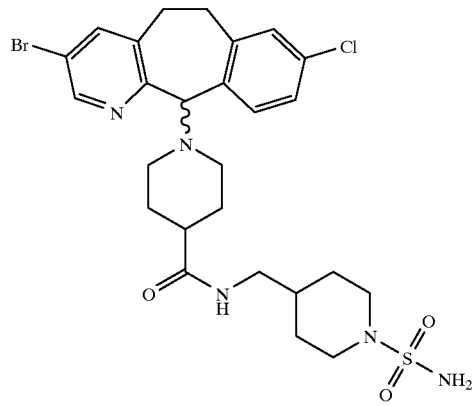

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) and sulfamide (10 equivalents) are added to water and the mixture is stirred under reflux at 100° C. for 43 h to give the title compound.

EXAMPLE 36

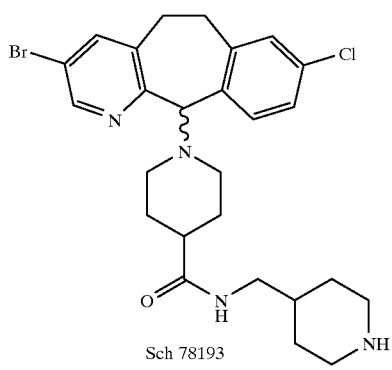

Sch 78193

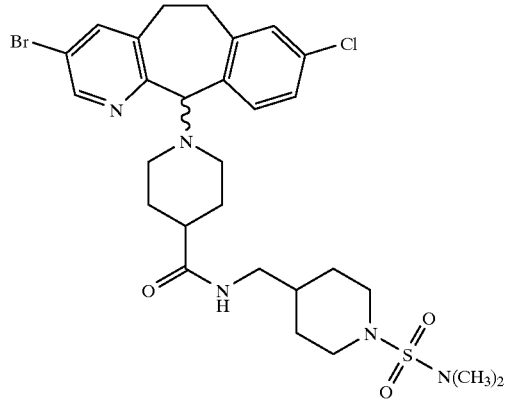

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) in dichloromethane is reacted with dimethylsulfamoyl chloride (1.1 equivalents) in the presence of triethylamine (2 equivalents) at from 0° C. to 25° C. to give the title compound.

EXAMPLE 37

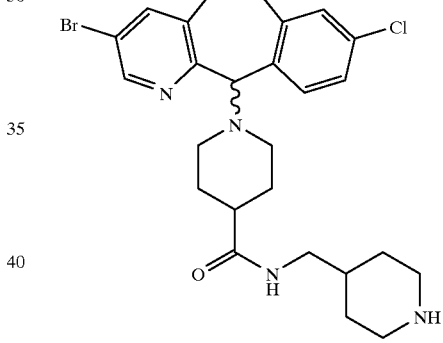

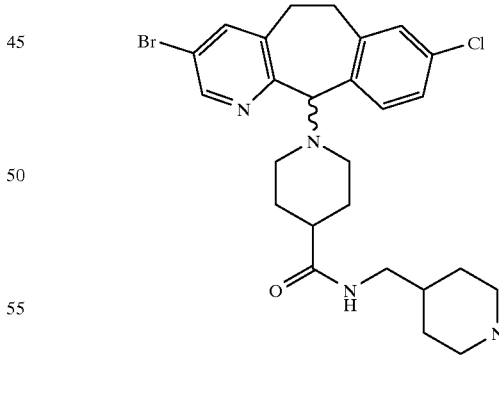

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) in

EXAMPLE 38

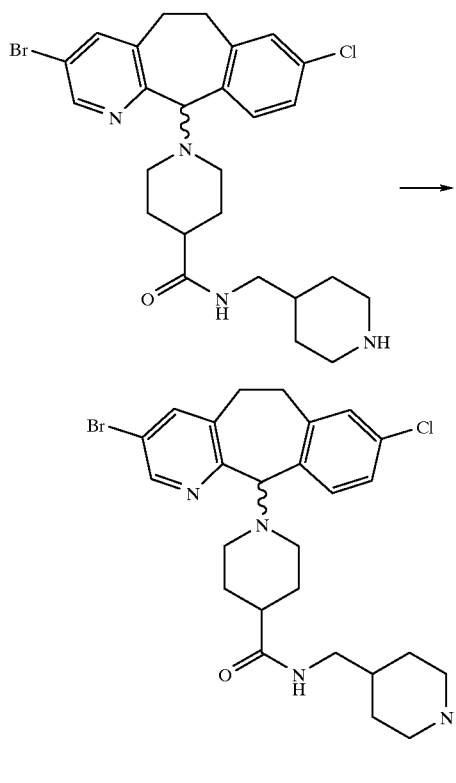

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) in DMF is reacted with dimethylphosphinic chloride (1.1 equivalents) and sodium carbonate at 25° C. to give the title compound.

EXAMPLE 39

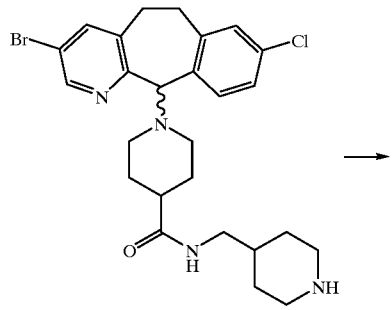

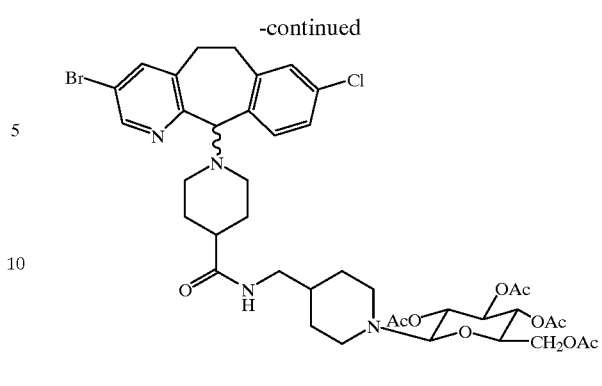

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) in DMF is reacted with tetra-O-acetyl-D-glucopyranosyl bromide (1.1 equivalents) in the presence of sodium carbonate to give the title compound.

EXAMPLE 40

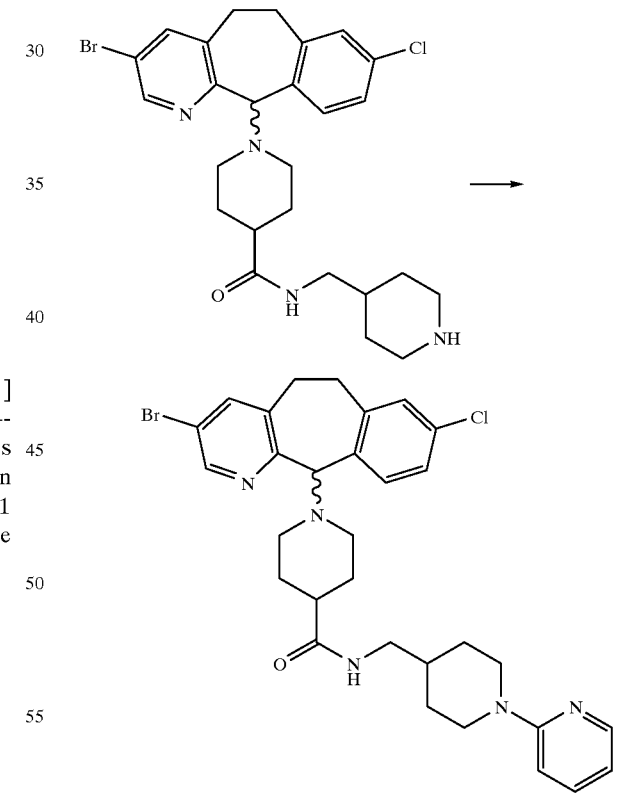

1-(3-Bromo-8-chloro-6,11-dihydro-5H-benzo[5,6]cyclohepta[1,2-b]pyridin-11-yl)-N-(4-piperidinylmethyl)-4-piperidinecarboxamide (1 equivalent) (prepared as described in Example 8, Procedures 1 or 2, Step B above) in DMF is reacted with 2-chloropyridine (1.1 equivalents) in the presence of sodium carbonate to give the title compound.

EXAMPLE 41

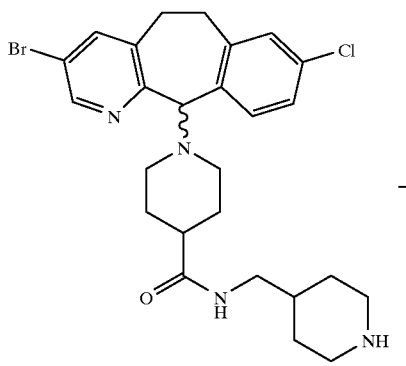

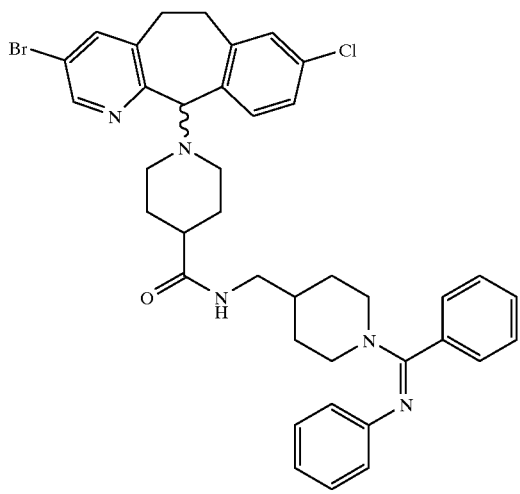

Benzanilide is converted into the choloroimidate (as described in: A. C. Honz and E. C. Wagner, Org. Syn. Coll. Vol. 4, 383–386 (1963) (1.1 equivalents) and this is reacted with 1-(3-Bromo-8-chloro-6,11-dihydro-5H-benzo[5,6] cyclohepta[1,2-b]pyridin-11-yl)-N-(4-piperidinylmethyl)-4-piperidine-carboxamide (1 equivalent) (prepared as described in Example 8, Procedures 1 or 2, Step B above) in pyridine at reflux temperature to give the title compound.

EXAMPLE 42

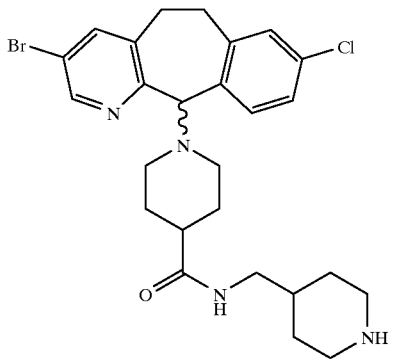

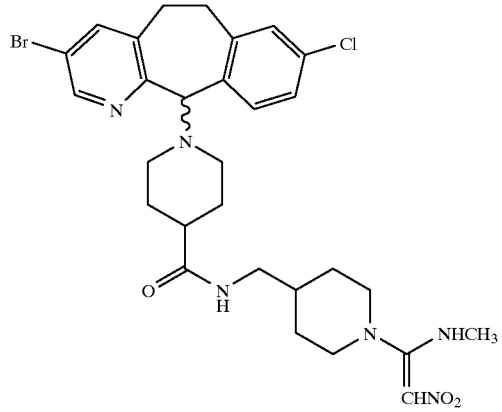

Copper(I)chloride (1 equivalent) is dissolved in anhydrous acetonitrile. To this solution, a solution of 1-(3-Bromo-8-chloro-6,11-dihydro-5H-benzo[5,6]cyclohepta[1,2-b] pyridin-11-yl)-N-(4-piperidinylmethyl)-4-piperidine-carboxamide (1 equivalent) (prepared as described in Example 8, Procedures 1 or 2, Step B above), 1-methylthio-1-methylamino-2-nitroethene (1 equivalent) (prepared as described in Canadian Patent 1,178,289 (1984)) and triethylamine in anhydrous acetonitrile is added dropwise over 10 minutes with stirring. The solid is filtered off. The volume is reduced and dichloromethane is added. The mixture is washed with aqueous sodium bicarbonate and the dichloromethane layer is dried over magnesium sulfate, filtered and evaporated to dryness. The residue is purified on silica gel to give the title compound.

EXAMPLE 43

1-(3-Bromo-8-chloro-6,11-dihydro-5H-benzo[5,6] cyclohepta[1,2-b]pyridin-11-yl)-N-(3-pyridylmethyl)-4-piperidineacetamide

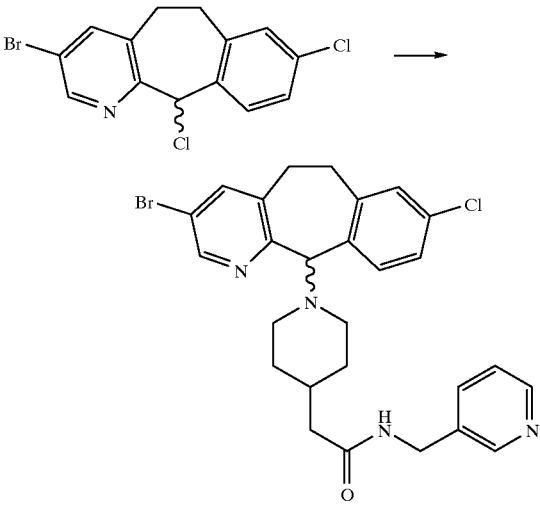

3-Bromo-8,11-dichloro-6,11-dihydro-5H-benzo[5,6] cyclohepta[1,2-b]pyridine (0.317 g, 0.924 mmoles) is dissolved in anhydrous THF (4.6 ml). N-(3-pyridylmethyl)-4-piperidineacetamide (prepared as described in Preparative Example 7, Step B) (0.2803 g, 1.2 mmoles) and triethylamine (0.386 ml, 2.77 mmoles) in anhydrous dichloromethane (5 ml) are added and the mixture is stirred at 25° C. for 18 h. The solution is diluted with dichloromethane and washed with 1N NaOH, dried over magnesium sulfate, filtered and evaporated to dryness. The product is chromatographed on silica gel using 4% (10% conc. ammonium hydroxide in methanol)-dichloromethane as the eluant to give the title compound (0.219 g, 44%), SIMS: m/z 539 (MH$^+$), FPT INH 43% @ 0.22 $\mu$M.

| | | $\delta_c$ (CDCl$_3$) |
|---|---|---|
| Tricyclic: | CH$_2$: | 30.3, 30.5 |
| | CH: | 79.5, 126.1, 130.5, 132.4, 141.1, 146.9 |
| | C: | 120.2, 126.4, 134.1, 135.5, 136.4, 143.5, 154.0 |
| Piperidine: | CH$_2$: | 41.0, 46.8, 47.0, 50.9, 50.9 |
| | CH: | 33.5 |
| | C: | 172.0 |
| Pyridine substituent: | CH$_2$: | 43.6 |
| | CH: | 123.7, 135.7, 148.9, 149.1 |
| | C: | 133.8 |

EXAMPLE 44
1-(3-Bromo-8-chloro-6,11-dihydro-5H-benzo[5,6]cyclohepta[1,2-b]pyridin-11-yl)-N-(3-pyridylmethyl)-4-piperidinepropanamide

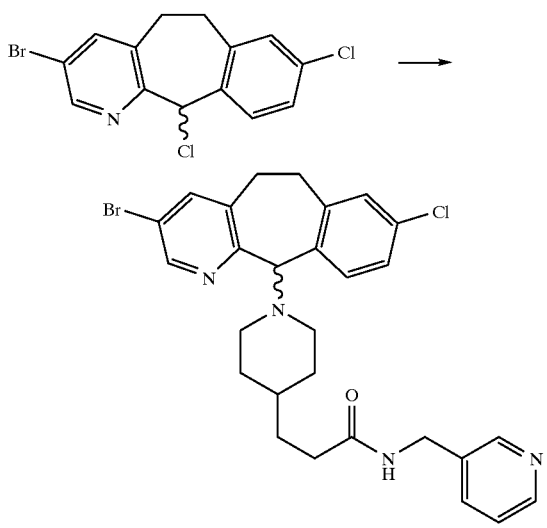

3-Bromo-8,11-dichloro-6,11-dihydro-5H-benzo[5,6]cyclohepta[1,2-b]pyridine (0.317 g, 0.924 mmoles) is dissolved in anhydrous THF (5 ml). N-(3-pyridylmethyl)-4-piperidinepropanamide (prepared as described in Preparative Example 8, Step C) (0.2972 g, 1.2 mmoles) and triethylamine (0.386 ml, 2.77 mmoles) in anhydrous dichloromethane (20 ml) are added and the mixture is stirred at 25° C. for 20 h. The solution is diluted with dichloromethane and washed with 1N NaOH, dried over magnesium sulfate, filtered and evaporated to dryness. The product is chromatographed on silica gel using 2.5% (10% conc. ammonium hydroxide in methanol)-dichloromethane as the eluant to give the title compound (0.3022 g, 59%), ESIMS: m/z 553.2 (MH$^+$), FPT INH 39% @ 0.35 $\mu$M.

| | | $\delta_c$ (CDCl$_3$) |
|---|---|---|
| Tricyclic: | CH$_2$: | 30.3, 30.5 |
| | CH: | 79.6, 126.0, 130.5, 132.3, 141.1, 146.8 |
| | C: | 119.6, 133.7, 136.6, 136.6, 140.6, 157.1 |
| Piperidine: | CH$_2$: | 32.1, 32.4, 32.4, 34.0, 52.0, 52.3 |
| | CH: | 35.6 |
| | C: | 173.2 |
| Pyridine substituent: | CH$_2$: | 41.0 |
| | CH: | 123.6, 136.6, 148.9, 149.2 |
| | C: | 134.2 |

EXAMPLE 45
1-(8-Chloro-3,10-dibromo-6,11-dihydro-5H-benzo[5,6]cyclohepta[1,2-b]pyridin-11-yl)-N-(3-pyridylmethyl)-4-piperidineacetamide

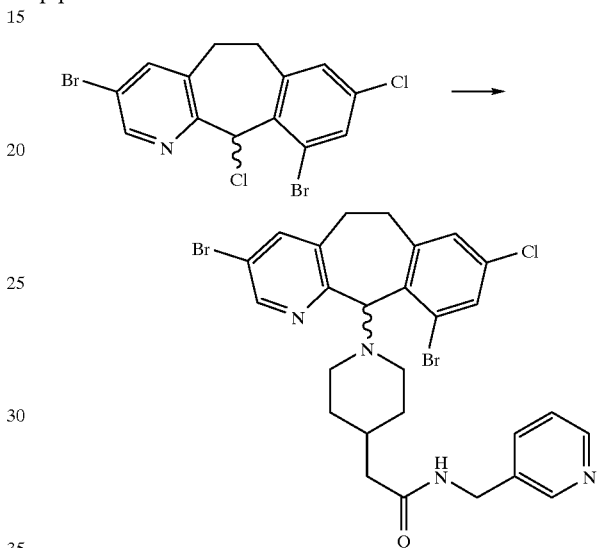

3,10-Dibromo-8,11-dichloro-6,11-dihydro-5H-benzo[5,6]cyclohepta[1,2-b]pyridine (prepared as described in Preparative Example 6, Step F) (0.2426 g, 0.575 mmoles) is dissolved in anhydrous THF (2.86 ml). N-(3-pyridylmethyl)-4-piperidineacetamide (prepared as described in Preparative Example 7, Step B) (0.175 g, 0.748 mmoles) and triethylamine (0.24 ml, 1.725 mmoles) in anhydrous THF (5 ml) are added and the mixture is stirred at 25° C. for 138 h. The solution is evaporated to dryness and the residue is dissolved in dichloromethane and washed with 1N NaOH, dried over magnesium sulfate, filtered and evaporated to dryness. The product is chromatographed on silica gel using 5% (10% conc. ammonium hydroxide in methanol)-dichloromethane as the eluant to give the title compound (0.021 g, 6%), ESIMS: m/z 617.2 (MH$^+$), FPT IC$_{50}$=0.042 $\mu$M.

| | | $\delta_c$ (CDCl$_3$) |
|---|---|---|
| Tricyclic: | CH$_2$: | 32.4, 32.4 |
| | CH: | 75.6, 129.6, 130.7, 141.6, 147.2 |
| | C: | 119.9, 126.2, 133.8, 136.2, 136.2, 143.2, 155.0 |
| Piperidine: | CH$_2$: | 29.9, 31.2, 41.0, 51.0, 51.5 |
| | CH: | 33.4 |
| | C: | 171.9 |
| Pyridine substituent: | CH$_2$: | 43.6 |
| | CH: | 123.7, 135.7, 148.9, 149.1 |
| | C: | 134.1 |

EXAMPLE 46
4-Carboxamido-1-[1-(8-chloro-3,10-dibromo-6,11-dihydro-5H-benzo[5,6]cyclohepta[1,2-b]pyridin-11-yl)-4-piperidineacetyl]piperidine

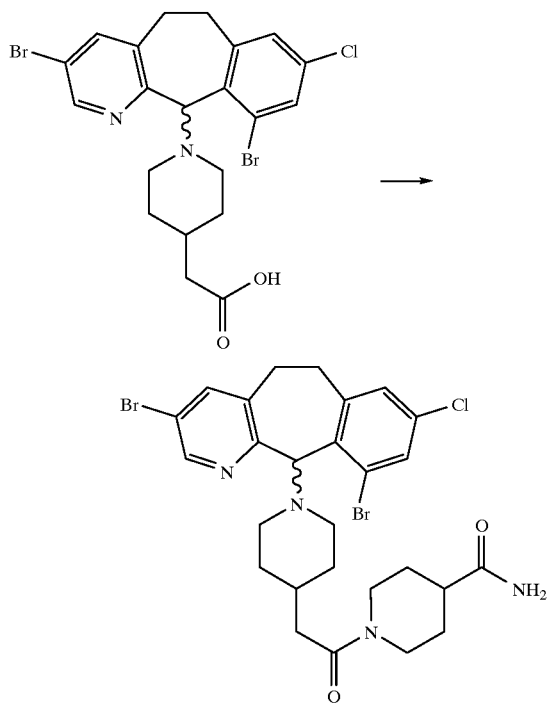

1-(8-Chloro-3,10-dibromo-6,11-dihydro-5H-benzo[5,6]cyclohepta[1,2-b]pyridin-11-yl)-4-piperidineacetic acid (0.5287 g, 1 mmole) (prepared as described in Preparative Example 10, Step B), isonipecotamide (0.1666 g, 1.3 mmoles), DEC.HCl (0.2492 g, 1.3 mmoles), HOBT (0.1757 g, 1.3 mmoles) and NMM (0.1315 g, 1.3 mmoles) are dissolved in anhydrous DMF (10 ml) and the mixture is stirred at 25° C. under argon for 24 h. The solution is evaporated to dryness and the residue is dissolved in dichloromethane, washed with 1N NaOH, dried over magnesium sulfate, filtered and evaporated to dryness. The product is chromatographed on silica gel using 0.75% (10% conc. ammonium hydroxide in methanol)-dichloromethane as the eluant to give the title compound.

EXAMPLE 47

3-Carboxamido-10-[1-(8-chloro-3,10-dibromo-6,11-dihydro-5H-benzo[5,6]cyclohepta[1,2-b]pyridin-11-yl)-4-piperidineacetyl]piperidine

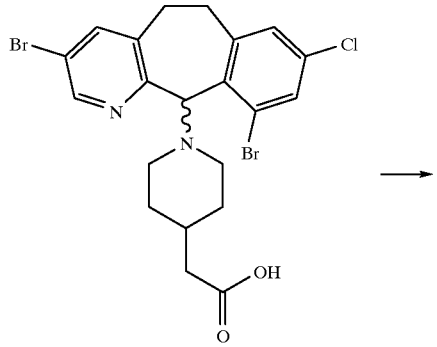

1-(8-Chloro-3,10-dibromo-6,11-dihydro-5H-benzo[5,6]cyclohepta[1,2-b]pyridin-11-yl)-4-piperidineacetic acid (0.5287 g, 1 mmole) (prepared as described in Preparative Example 10, Step B) and nipecotamide (0.1666 g, 1.3 mmoles), DEC.HCl (0.2492 g, 1.3 mmoles), HOBT (0.1757 g, 1.3 mmoles) and NMM (0.1315 g, 1.3 mmoles) are dissolved in anhydrous DMF (10 ml) and the mixture is stirred at 25° C. under argon for 24 h. The solution is evaporated to dryness and the residue is dissolved in dichloromethane, washed with 1N NaOH, dried over magnesium sulfate, filtered and evaporated to dryness. The product is chromatographed on silica gel using 0.75% (10% conc. ammonium hydroxide in methanol)-dichloromethane as the eluant to give the title compound.

EXAMPLE 48

4-[1-(8-Chloro-3,10-dibromo-6,11-dihydro-5H-benzo[5,6]cyclohepta[1,2-b]pyridin-11-yl)-4-piperidineacetyl]-1-piperazinecarboxamide

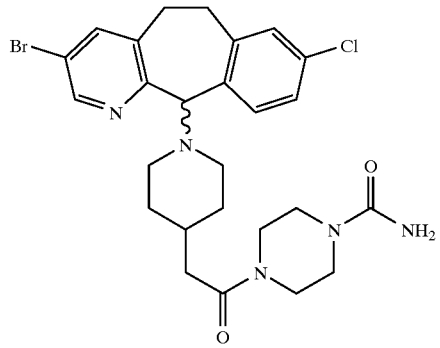

Step A

4-[1-(8-Chloro-3,10-dibromo-6,11-dihydro-5H-benzo[5,6]cyclohepta[1,2-b]pyridin-11-yl)-4-piperidineacetyl]-1-N-tert-butoxycarbonylpiperazine

71

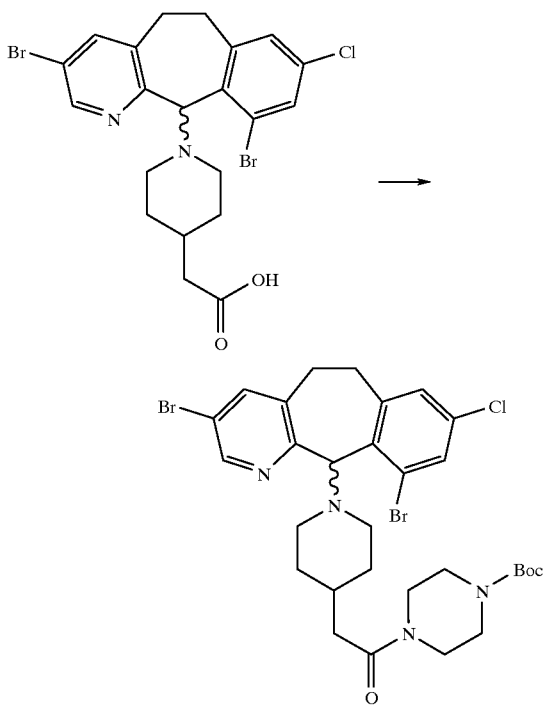

1-(8-Chloro-3,10-dibromo-6,11-dihydro-5H-benzo[5,6]cyclohepta[1,2-b]pyridin-11-yl)-4-piperidineacetic acid (0.5287 g, 1 mmole) (prepared as described in Preparative Example 10, Step B) and 1-N-tert-butoxycarbonylpiperazine (0.1667 g, 1.3 mmoles), DEC.HCl (0.2492 g, 1.3 mmoles), HOBT (0.1757 g, 1.3 mmoles) and NMM (0.1315 g, 1.3 mmoles) are dissolved in anhydrous DMF (10 ml) and the mixture is stirred at 25° C. under argon for 24 h. The solution is evaporated to dryness and the residue is dissolved in dichloromethane, washed with 1N NaOH, dried over magnesium sulfate, filtered and evaporated to dryness. The product is chromatographed on silica gel using 0.75% (10% conc. ammonium hydroxide in methanol)-dichloromethane as the eluant to give the title compound.

Step B

1-[1-(8-Chloro-3,10-dibromo-6,11-dihydro-5H-benzo[5,6]cyclohepta[1,2-b]pyridin-11-yl)-4-piperidineacetyl]piperazine

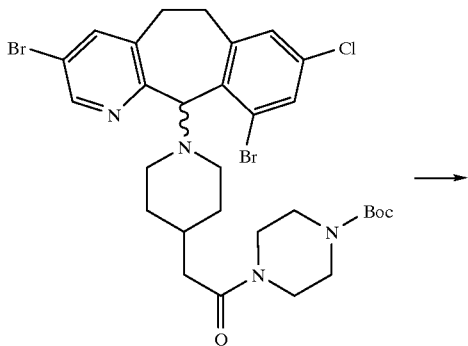

72

-continued

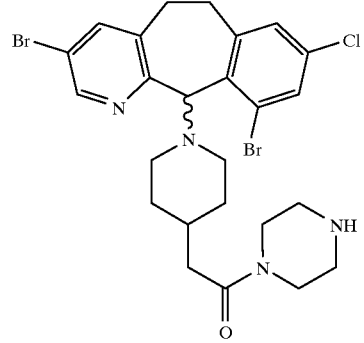

4-[1-(8-Chloro-3,10-dibromo-6,11-dihydro-5H-benzo[5,6]cyclohepta[1,2-b]pyridin-11-yl)-4-piperidineacetyl]-1-N-tert-butoxycarbonylpiperazine (prepared as described in Step A above) is converted into 1-[1-(8-Chloro-3,10-dibromo-6,11-dihydro-5H-benzo[5,6]cyclohepta[1,2-b]pyridin-11-yl)-4-piperidineacetyl]piperazine by essentially the same procedure as described in Example 8, Procedure 2, Step B.

Step C

4-[1-(8-Chloro-3,10-dibromo-6,11-dihydro-5H-benzo[5,6]cyclohepta[1,2-b]pyridin-11-yl)-4-piperidineacetyl]-1-piperazinecarboxamide

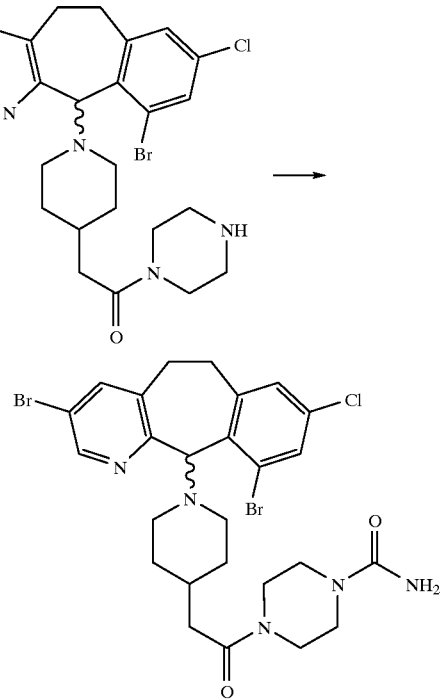

1-[1-(8-Chloro-3,10-dibromo-6,11-dihydro-5H-benzo[5,6]cyclohepta[1,2-b]pyridin-11-yl)-4-piperidineacetyl]piperazine (prepared as described in Step B above) is converted into 4-[1-(8-Chloro-3,10-dibromo-6,11-dihydro-5H-benzo[5,6]cyclohepta[1,2-b]pyridin-11-yl)-4-piperidineacetyl]-1-piperazinecarboxamide by essentially the same procedure as decribed in Example 8, Procedure 2, Step C above.

EXAMPLE 49

N-cyclopropyl-1-(3,10-dibromo-8-chloro-6,11-dihydro-5H-benzo[5,6]cyclohepta[1,2-b]pyridin-11-yl)-3piperidinecarboxamide -

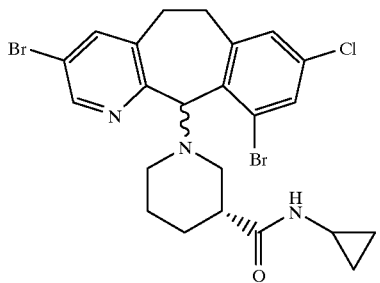

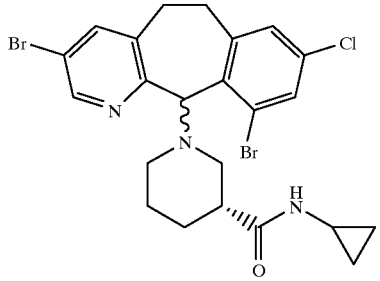

Following the method of Example 10, Procedure 1, except that (a) the compound 3,10-dibromo-8,10-dichloro-6,11-dihydro-5H-benzo[5,6]cyclohepta[1,2-b]pyridine is substituted for 3-bromo-8,10-dichloro-6,11-dihydro-5H-benzo[5,6]cyclohepta[1,2-b]pyridine in Step A, and (b) cyclopropyl amine is substituted for 3-aminomethylpyridine in Step C, the title compound is obtained. FABMS (MH+)=554. FPT IC$_{50}$=0.58 uM.

EXAMPLE 50

1-(3,10-Dibromo-8-chloro-6,11-dihydro-5H-benzo[5,6]cyclohepta[1,2-b]pyridin-11-yl)-N-methyl-3-piperidinecarboxamide

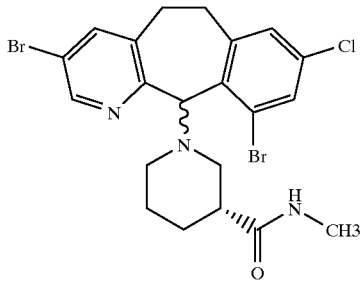

Following the method of Example 10, Procedure 1, except that (a) the compound 3,10-dibromo-8,10-dichloro-6,11-dihydro-5H-benzo[5,6]cyclohepta[1,2-b]pyridine is substituted for 3-bromo-8,10-dichloro-6,11-dihydro-5H-benzo[5,6]cyclohepta[1,2-b]pyridine in Step A, and (b) methylamine is substituted for 3-aminomethylpyridine in Step C, the title compound is obtained. FABMS (MH+)=528. FPT IC$_{50}$=0.96 uM.

EXAMPLE 51

1-(3,10-Dibromo-8-chloro-6,11-dihydro-5H-benzo[5,6]cyclohepta[1,2-b]pyridin-11-yl)-N-(3-pyridinylmethyl)-3-piperidinecarboxamide N1-oxide (Isomer B)

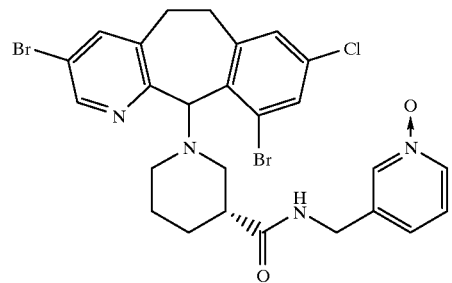

Following the method of Example 10, Procedure 1, except that (a) the compound 3,10-dibromo-8,10-dichloro-6,11-dihydro-5H-benzo[5,6]cyclohepta[1,2-b]pyridine is substituted for 3-bromo-8,10-dichloro-6,11-dihydro-5H-benzo[5,6]cyclohepta[1,2-b]pyridine in Step A, and (b) 3-aminomethylpyridine-N-oxide is substituted for 3-aminomethylpyridine in Step C, the title compound is obtained. FABMS (MH+)=619.

FPT IC$_{50}$=0.1 uM.

EXAMPLE 52

1-(3,10-Dibromo-8-chloro-6,11-dihydro-5H-benzo[5,6]cyclohepta[1,2-b]pyridin-11-yl)-N-[2-(3-pyridinyl)ethyl]-3-piperidincarboxamide

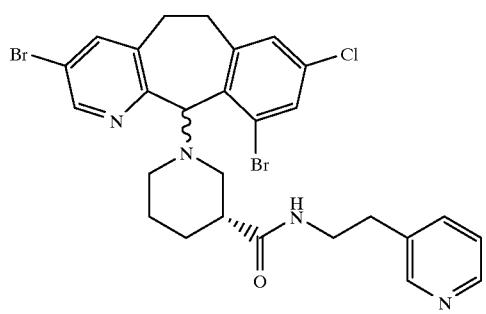

Following the method of example 10, procedure 1, except that (a) the compound 3,10-dibromo-8,10-dichloro-6,11-dihydro-5H-benzo[5,6]cyclohepta[1,2-b]pyridine is substituted for 3-bromo-8,10-dichloro-6,11-dihydro-5H-benzo[5,6]cyclohepta[1,2-b]pyridine in Step A, and (b) 3-aminoethylpyridine is substituted for 3-aminomethylpyridine in Step C, the title compound is obtained. FABMS (MH+)=617.

FPT IC$_{50}$=0.081 uM

EXAMPLE 53

1-(3,10-Dibromo-8-chloro-6,11-dihydro-5H-enzo[5,6]cyclohepta[1,2-b]pyridin-11-yl)-N-[[1-[(dimethylamino)acetyl]-4-piperidinyl]methyl]-3-piperidinecarboxamide

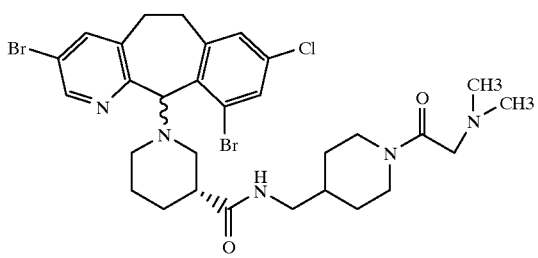

Following the method of Example 10, Procedure 1, except that (a) the compound 3,10-dibromo-8,10-dichloro-6,11-dihydro-5H-benzo[5,6]cyclohepta[1,2-b]pyridine is substituted for 3-bromo-8,10-dichloro-6,11-dihydro-5H-benzo[5,6]cyclohepta[1,2-b]pyridine in Step A, and (b) dimethylaminoacetyl-4-piperidinylmethyl-3-amine is substituted for 3-aminomethylpyridine in Step C, the title compound is obtained.

FABMS (MH+)=694. FPT $IC_{50}$=0.11 uM

EXAMPLE 54

1-(3,10-Dibromo-8-chloro-6,11-dihydro-5H-benzo[5,6]cyclohepta[1,2-b]pyridin-11-yl)-N-[3-(2-oxo-1-pyrrolidinyl)propyl]-3-piperidinecarboxamide

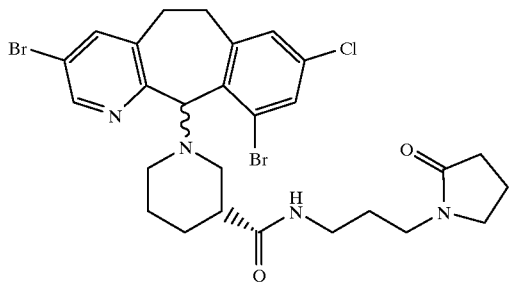

Following the method of Example 10, Procedure 1, except that (a) the compound 3,10-dibromo-8,10-dichloro-6,11-dihydro-5H-benzo[5,6]cyclohepta[1,2-b]pyridine is substituted for 3-bromo-8,10-dichloro-6,11-dihydro-5H-benzo[5,6]cyclohepta[1,2-b]pyridine in Step A, and (b) 3-aminopropylpyrrolidinone amine is substituted for 3-aminomethylpyridine in Step C, the title compound is obtained. FABMS (MH+)=637.

FPT $IC_{50}$=1 uM

Preparation of Starting Materials

Starting materials useful in preparing the compounds of the present invention are exemplified by the following preparative examples, which should not be construed to limit the scope of the disclosure. The tricylic compounds (3.0) and substituted piperidinyl compounds (7.0) used as starting materials are known in the art and/or can be prepared using known methods, such as taught in U.S. Pat. Nos. 5,089,496; 5,151,423; 4,454,143; 4,355,036; PCT/US94/11390 (WO95/10514); PCT/US94/11391 (WO 95/10515); PCT/US94/11392 (WO95/10516); Stanley R. Sandler and Wolf Karo, Organic Functional Group Preparations, 2nd Edition, Academic Press, Inc., San Diego, Calif., Vol. 1–3, (1983); in J. March, Advanced Organic Chemistry, Reactions & Mechanisms, and Structure, 3rd Edition, John Wiley & Sons, New York, 1346 pp. (1985); in G. R. Newkome (Ed.), Pyrdine and its Derivatives, John Wiley and Sons Inc., New York, N.Y., Vol.1–5, (1984); A. J. Boulton and A. McKillop (Eds.), Comprehensive Heterocyclic Chemistry, Volume 2, Part 2A, Six Membered Rings With One Nitrogen Atom, Pergamon Press, Elmsford, N.Y., (1960–1985); and Chia-Lin J. Wang and Mark A. Wuonola, Recent Progress in the Synthesis and Reactions of Substituted Piperidines. A Review, Organic Preparations and Procedures International Vol 24, p. 585, (1992).The starting materials may also be prepared as taught in copending U.S. application Ser. No. 08/410,187 filed Mar. 24, 1995, copending U.S. application Ser. No. 08/577,951 filed Dec. 22, 1995, and copending U.S. application Ser. No. 08/615,760 filed Mar. 13, 1996; the disclosures being incorporated herein by reference. Alternative mechanistic pathways and analogous structures within the scope of the invention may be apparent to those skilled in the art.

For example, piperidinyl compounds of formula (7.0), wherein T=—CO— or —$CR^{30}R^{31}$— can be prepared by initially preparing a pyridine compound substituted with the requisite 2-, 3-, or 4 —$(CH_2)_nCR^{30}R^{31}Z$ or —$(CH_2)_nCOZ$ moiety, together with any optional —$R^5$, —$R^6$, —$R^7$ and/or —$R^8$ moieties, as described, in the references cited above. The 2-, 3- or 4-substituted pyridine compound can subsequently be reduced using conventional reduction procedures, such as catalytic hydrogenation, to give the desired piperidinyl compound (7.0). One skilled in the art will appreciate that in cases where —$R^5$, —$R^6$, —$R^7$, —$R^8$ and/or Z moieties also contain reducible groups, it may useful to utilize alternative methods.

The sulfonylpiperidinyl compounds of formula (7.0), wherein T=—$SO_2$— can be prepared by reacting the appropriate 2-, 3-, or 4-hydroxy-N-blocked-piperidine with a suitable chlorinating agent such as thionyl chloride to obtain the 2-, 3-, or 4-chloro-N-blocked piperidine, using N-blocking groups such as benzyloxycarbonyl or tert-butoxycarbonyl. The 2-, 3-, or 4-chloro-N-blocked piperidine can then be reacted with sodium bisulfite to obtain the corresponding 2-, 3-, or 4-sulfonic acid N-blocked piperidine sodium salt. This salt is then reacted with an appropriate chlorinating agent such as phosphorus pentachloride or phosphorus oxychloride to obtain the corresponding 2-, 3- or 4-sulfonylchloride-N-blocked piperidine. This sulfonyl chloride is then reacted with the corresponding agent containing the desired Z group (i.e. amines, alkylating agents and the like) to obtain the desired sulfonylpiperidine (7.0).

The sulfonylpiperidine wherein T=—SO— (with the proviso that Z is not —$NR^{40}R^{42}$) can be prepared by reacting the appropriate 2-, 3-, or 4-hydroxy-N-blocked-piperidine with a suitable chlorinating agent such as thionyl chloride to obtain the 2-, 3-, or 4-chloro-N-blocked piperidine, using N-blocking groups such as benzyloxycarbonyl or tert-butoxycarbonyl. The 2-, 3-, or 4-chloro-N-blocked piperidine can then reacted with the corresponding substituted sulfide (i.e. arylsulfide, alkylsulfides and the like) to obtain the appropriate 2-, 3-, or 4-sulfide-N-blockedpiperidine. This compound can then be reacted with an oxidizing agent such as meta-chloroperbenzoic acid to obtain the desired sulfonylpiperidine (7.0).

Preparative Example 1

4-Piperidinyl-N-(4-pyridinyl)carboxamide

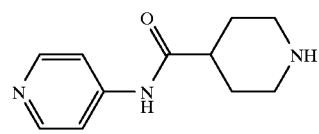

Step A
1-N-(tert-Butoxycarbonyl-4-piperidine carboxylic acid or 1-N-(tert-butoxycarbonyl)isonipecotic acid

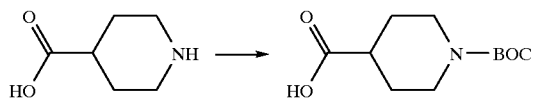

Isonipecotic acid (5 g; 1 equivalent) is dissolved in water (50 ml) and a solution of di-tert-butyldicarbonate (8.62 g; 1.02 equivalents) in THF (70 ml) is added with stirring. The mixture is stirred at 80° C. for 2 h and then evaporated to dryness. The residue is partitioned between dichloromethane and brine and the dichloromethane layer is dried over magnesium sulfate, filtered and evaporated to dryness. The product is chromatographed on a silica gel column (30×5 cm) using 15% (10% concentrated ammonium hydroxide in methanol)-dichloromethane as the eluant to give the title compound (4.3109 g; 49% yield), CIMS: m/z 230 (MH$^+$).

Step B
1-N-(tert-Butoxycarbonyl)-4-piperidinyl-N-(4-pyridinyl) carboxamide

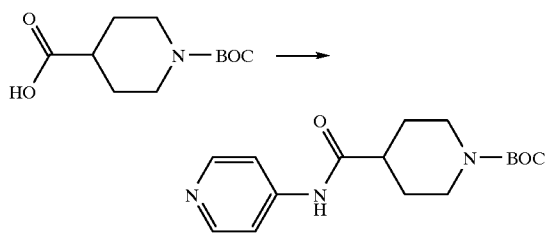

1-N-(tert-Butoxycarbonyl)-4-piperidinecarboxylic acid (1.218; 1 equivalent) (prepared as described in Step A above), DEC (1.0184 g; 1 equivalent), HOBT (0.7179 g; 1 equivalent) and N-methylmorpholine (0.5841 ml; 1 equivalent) are dissolved in anhydrous DMF (30 ml) and the mixture is stirred under argon at 25° C. for 19 h. The solution is evaporated to dryness. The residue is taken up in dichloromethane and washed with water. The dichloromethane layer is dried over magnesium sulfate, filtered and evaporated to dryness. The product is chromatographed on a silica gel column (60×2.5 cm) using 5% (10% concentrated ammonium hydroxide in methanol)-dichloromethane as the eluant to give the title compound (0.8142 g; 50% yield), CIMS: m/z 306 (MH$^+$).

Step C
4-Piperidinyl-N-(4-pyridinyl)carboxamide

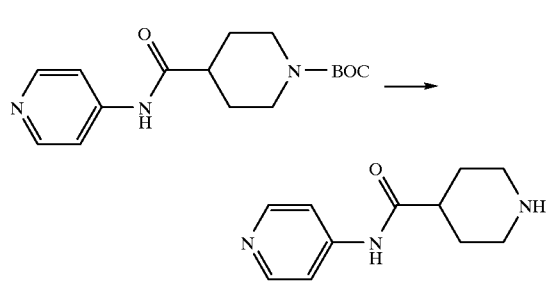

1-N-(tert-Butoxycarbonyl)-4-piperidinyl-N-(4-pyridyl) carboxamide (1 g; 1 equivalent) is dissolved in 10% (v/v) concentrated sulfuric acid in dioxane (24.36 ml) and the mixture is stirred at 25° C. for 0.5 h. The mixture is poured into water (150 ml) and neutralized with Amberlite IRA401S(OH$^-$) ion exchange resin (300 ml). The resin is eluted with water (1500 ml) and the eluant is evaporated to give the title compound (0.4258 g; 63% yield), CIMS: m/z 206 (MH$^+$).

Preparative Example 2
1-[3-Bromo-8-chloro-6,11-dihydro-5H-benzo[5,6] cyclohepta[1,2-b]pyridin-11-yl]-4-piperidinecarboxylate

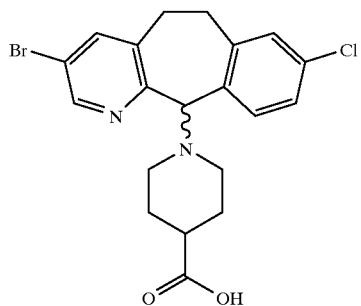

Procedure 1
Step A
Ethyl 1-[3-bromo-8-chloro-6,11-dihydro-5H-benzo[5,6] cyclohepta[1,2-b]pyridin-11-yl]-4-piperidinecarboxylate

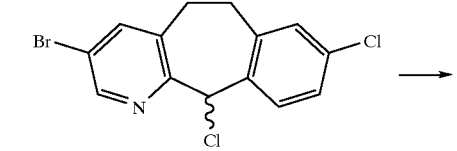

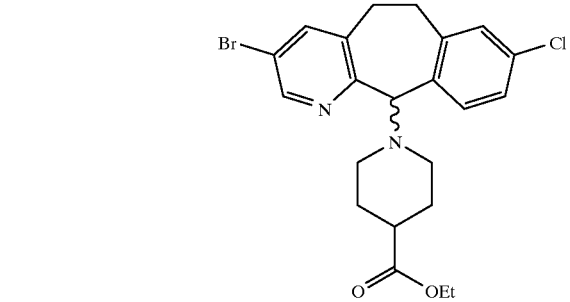

3-Bromo-8,11-dichloro-6,11-dihydro-5H-benzo[5,6] cyclohepta[1,2-b]pyridine (1 g; 1 equivalent) and ethyl isonipecotate (2.3735 ml) (5 equivalents) are dissolved in dry THF (20 ml) and the mixture was stirred at 25° C. under argon for 19 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (30×5 cm) using 0.75% (10% concentrated ammonium hydroxide in methanol)-dichloromethane as the eluant to give the title compound (1.5134 g; 100% yield), CIMS: m/z 463.15 (MH$^+$).

Step B
1-[3-Bromo-8-chloro-6,11-dihydro-5H-benzo[5,6] cyclohepta[1,2-b]pyridin-11-yl]-4-piperidinecarboxylate

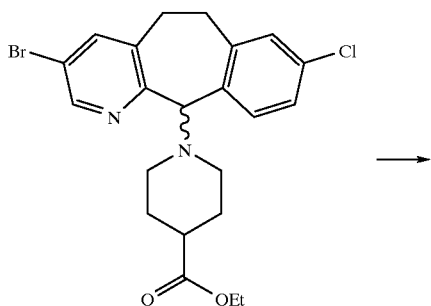
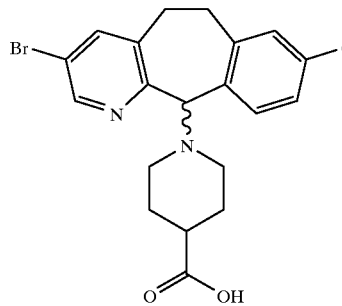

Ethyl 1-[3-bromo-8-chloro-6,11-dihydro-5H-benzo[5,6]cyclohepta[1,2-b]pyridin-11-yl]-4-piperidinecarboxylate (0.250 g; 1 equivalent) (prepared as described in Step A above), is dissolved in ethanol (3 ml) and dichloromethane (3 ml) and 1.0M lithium hydroxide in water (1.3044 ml; 2.42 equivalents) is added The mixture is stirred at 50° C. for 5 h. 1.0N Hydrochloric acid (1.5169 ml ) (2.81 equivalents) is added and the solution is evaporated to dryness after stirring for 5 min. to give the title compound which is used without further purification.
Procedure 2
1-[3-Bromo-8-chloro-6,11-dihydro-5H-benzo[5,6]cyclohepta[1,2-b]pyridin-11-YL]-4-piperidinecarboxylate

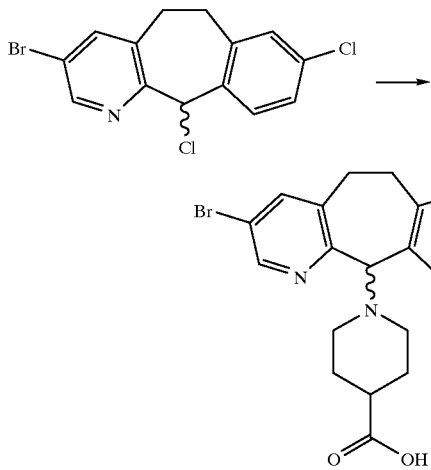
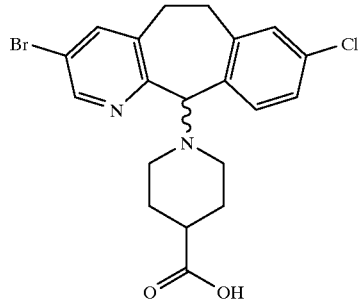

3-Bromo-8,11-Dichloro-6,11-dihydro-5H-benzo[5,6]cyclohepta[1,2-b]pyridine (prepared as described in Preparative Example 40, Step B in INO291K) (0.5 g; 1 equivalent), isonipecotic acid (0.3978 g; 2 equivalents) and 4-N-methylmorpholine (0.847 ml; 5 equivalents) are dissolved in anhydrous DMF (9.6 ml) and the mixture is heated at 80° C. for 16.5 h. The solution is evaporated to dryness and the product is chromatographed on a silica gel column (60×2.5 cm) using 10% ethyl acetate in hexane, followed by 1% (10% concentrated ammonium hydroxide in methanol)-dichloromethane as the eluant to give the title compound (0.2426 g; 36% yield), CIMS: m.z 435.1 (MH$^+$).

Preparative Example 3
4-(Aminomethyl)-1-N-(tert-butoxycarbonyl)piperidine

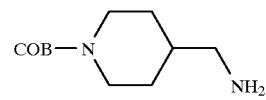

Ref.: J. D. Prugh, L. A. Birchenough and M. S. Egbertson, Synthetic Communications, 22(16), 2357–2360 (1992).
Step A
4-(Benzylidineaminomethyl)piperidine

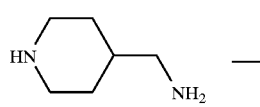

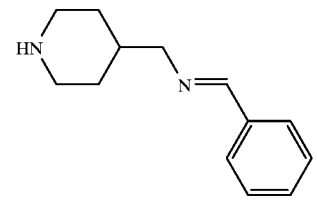

4-Aminomethylpiperidine (11.4 g) (1 equivalent) is dissolved in anhydrous toluene (125 ml) and benzaldehyde (10.6 g) (1 equivalent) is added. The mixture is heated at 120° C. under reflux for 4 h, using a Dean-Stark trap to remove water. The crude solution of the title compound is used directly in Step B below.
Step B
1-N-(tert-Butoxycarbonyl)-4-(benzylidineaminomethyl)piperidine

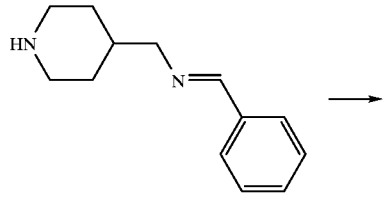

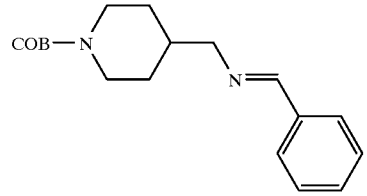

4-(Benzylideneaminomethyl)piperidine in toluene (From Step A above) is treated with di-tert-butyldicarbonate (24 g) (1.1 equivalents) in portions over 0.5 h. The mixture is stirred at 25° C. for 69 h. The solution is evaporated to dryness to give the title compound which is used directly in Step C below.

Step C
4-(Aminomethyl)-1-N-(tert-butoxycarbonyl)piperidine

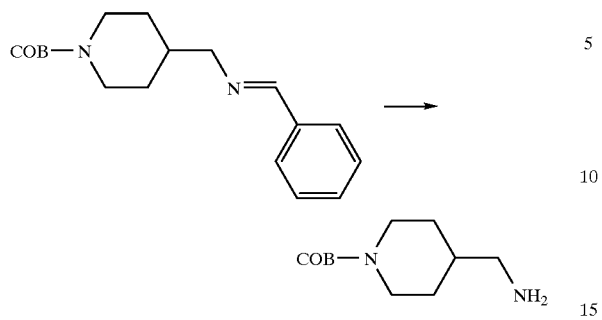

1-N-(tert-Butoxycarbonyl)-4-(benzylideneaminomethyl) piperidine (prepared as described in Step B above) is dissolved in 1.0N aqueous potassium hydrogen sulfate (220 ml) and the mixture is stirred at 25° C. for 4 h. The solution is extracted with ether (3×200 ml) and the ether is discarded. The aqueous layer is adjusted to pH 12.5 using 50% aqueous sodium hydroxide and the solution is then saturated with solid sodium chloride and extracted with dichloromethane. The dichloromethane layer is dried over magnesium sulfate, filtered and evaporated to dryness. The product is chromatographed on a silica gel column (60×5 cm) using 1% increasing to 7% (10% concentrated ammonium hydroxide in methanol)-dichloromethane as the eluant to give the title compound (9.82 g; 46% yield), an oil, CIMS: m/z 215 (MH+).

Preparative Example 4
1-N-Benzyl-4-(aminomethyl)piperidine

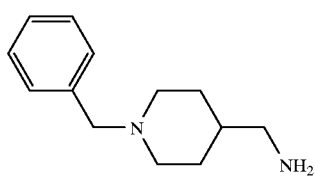

Step A
1-N-Benzyl-4-piperidinecarboxamide

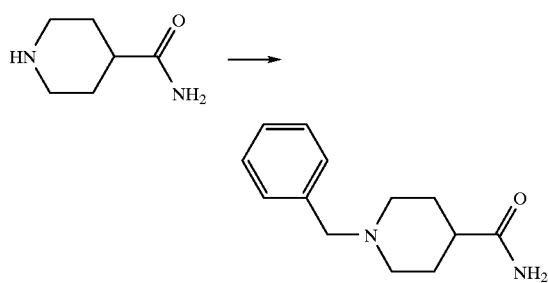

4-Piperidinecarboxamide (5 g; 1 equivalent) and triethylamine (16.3 ml) (3 equivalents) are dissolved in anhydrous dichloromethane (30 ml) and anhydrous DMF (80 ml). A solution of benzyl bromide (4.55 ml) (0.98 equivalents) in anhydrous dichloromethane (10 ml) is added dropwise over 10 min and the mixture is stirred at 25° C. for 22 h. The mixture is filtered and the filtrate is evaporated to dryness. The product is chromatographed on a silica gel column (60×5 cm) using dichloromethane (1 liter) and then 5% (10% concentrated ammonium hydroxide in methanol)-dichloromethane as the eluant to give the title compound (6.15 g; 72% yield), CIMS: m/z 219.05 (MH+).

Step B
1-N-Benzyl-4-(aminomethyl)piperidine

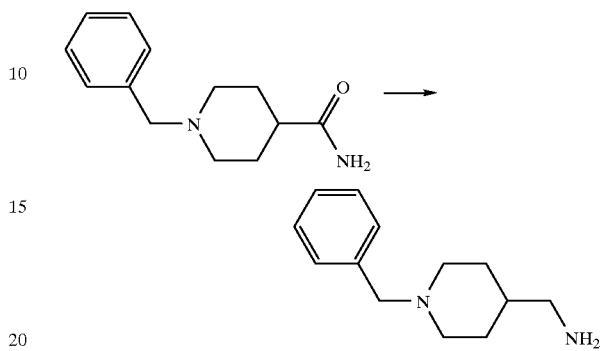

1-N-Benzyl-4-piperidinecarboxamide (1 g; 1 equivalent) (prepared as described in Step A above) is dissolved in anhydrous THF (25 ml). Lithium aluminum hydride (0.2173 g) (1.25 equivalents) in anhydrous THF (5.726 ml) is added dropwise over 0.5 h and the mixture is heated under reflux under nitrogen for 20 h. The mixture is cooled and diluted with dichloromethane (750 ml) and washed with 1.0N sodium hydroxide. The dichloromethane layer is dried over magnesium sulfate, filtered and evaporated to dryness. The product is chromatographed on a silica gel column (60×2.5 cm) using 2% (10% concentrated ammonium hydroxide in methanol)-dichloromethane as the eluant to give the title compound (0.5237 g; 56% yield), FABMS: m/z 205.4 (MH+).

Preparative Example 5
Step A
4-(N-Benzyloxycarbonylaminomethyl)piperidine

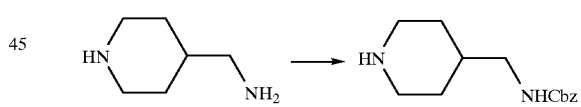

4-Aminomethylpiperidine (1 g; 1 equivalent) and DMAP (0.054 g; 0.05 equivalents) are dissolved in anhydrous dichloromethane (40 ml). N-Benzyloxycarbonylimidazole (1.7709 g; 1 equivalent) [prepared as described in: S. K. Sharma, M. J. Miller and S. M. Payne, J. Med. Chem., 32, 357–367 (1989)] is added and the mixture is stirred at 25° C. for 23 h. The solution is diluted with dichloromethane and washed with 1.0N sodium hydroxide. The dichloromethane layer is dried over magnesium sulfate, filtered and evaporated to dryness. The product is chromatographed on a silica gel column (60×2.5 cm) using 3% increasing to 7% (10% concentrated ammonium hydroxide in methanol)-dichloromethane as the eluant to give the title compound (1.0719 g; 49% yield ), FABMS: m/z 249.3 (MH+).

Step B
1-N-(Benzyloxycarbonyl)-4-[N-(tert-butoxycarbonyl) aminomethyl]piperidine

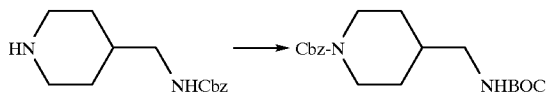

4-(N-Benzyloxycarbonylaminomethyl)piperidine (0.6814 g; 1 equivalent) (prepared as described in Step A above) is dissolved in anhydrous toluene (5 ml) and di-tert-butyldicarbonate (0.599 g; 1 equivalent) in anhydrous toluene (5 ml) is added dropwise. The mixture is stirred at 0° C. for 2 h and at 25° C. for 20 h. The solution is evaporated to dryness and the residue is taken up in dichloromethane and washed with 1.0N sodium hydroxide. The dichloromethane layer is dried over magnesium sulfate, filtered and evaporated to dryness. The product is chromatographed on a silica gel column (60×2.5 cm) using 0.5% (10% concentrated ammonium hydroxide in methanol)-dichloromethane as the eluant to give the title compound (0.9314 g; 97% yield), FABMS: m/z 349.3 (MH$^+$).

Step C
4-[(tert-Butoxycarbonylamino)methyl]piperidine

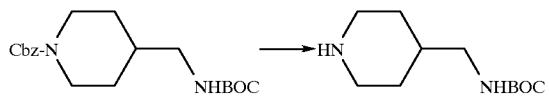

1-N-(Benzyloxycarbonyl)-4-[(tert-butoxycarbonylamino) methyl]-piperidine (0.4 g) (1 equivalent) (prepared as described in Step B above) is dissolved in methanol (16 ml) and 5% Pd-C (0.0638 g) is added. The mixture is hydrogenated at 30 psi at 25° C. for 17 h. The catalyst is removed by filtration through Celite which is washed with methanol. The combined filtrates are evaporated to dryness. The residue is taken up in dichloromethane and washed with 1.0N sodium hydroxide. The dichloromethane layer is dried over magnesium sulfate, filtered and evaporated to dryness. The product is chromatographed on a silica gel column (45×2.5 cm) using 2% increasing to 7% (10% concentrated ammonium hydroxide in methanol)-dichloromethane as the eluant to give the title compound (0.2001 g; 81% yield), FABMS: m/z 215.4 (MH$^+$).

Preparative Example 6
Step A

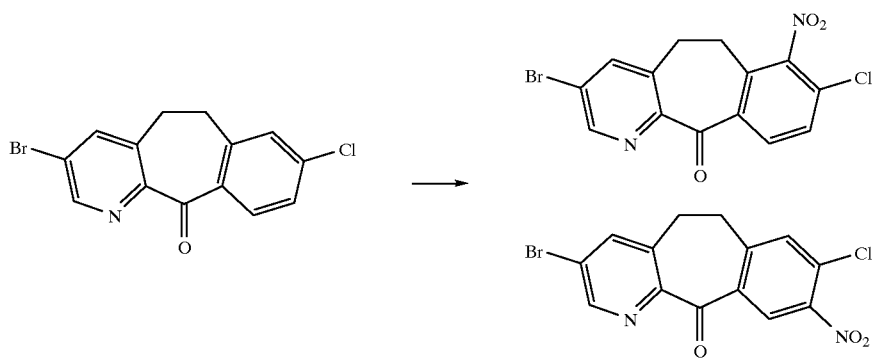

Combine 40.0 g (0.124 mole) of the starting ketone and 200 mL of H$_2$SO$_4$ and cool to 0° C. Slowly add 13.78 g (0.136 mole) of KNO$_3$ over a period of 1.5 hrs., then warm to room temperature and stir overnight. Work up the reaction using substantially the same procedure as described for Preparative Example 4, Step A. Chromatograph (silica gel, 20%, 30%, 40%, 50% EtOAc/hexane, then 100% EtOAc) to give 28 g of the 9-nitro product, along with a smaller quantity of the 7-nitro product and 19 g of a mixture of the 7-nitro and 9-nitro compounds.

Step B

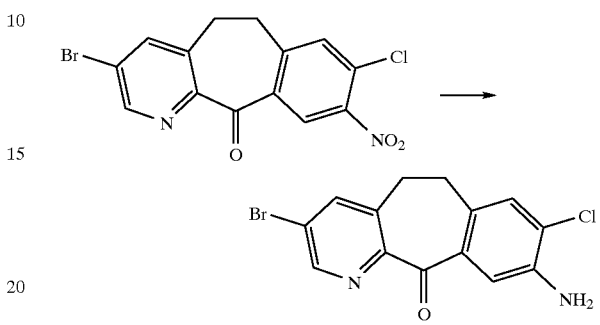

React 28 g (76.2 mmol) of the 9-nitro product of Step A, 400 mL of 85% EtOH/water, 3.8 g (34.3 mmol) of CaCl$_2$ and 38.28 g (0.685 mole) of Fe using substantially the same procedure as described for Preparative Example 4, Step C, to give 24 g of the product Step C

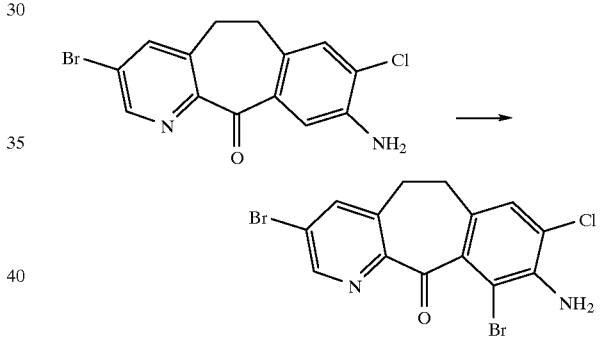

Combine 13 g (38.5 mmol) of the product of Step B, 140 mL of HOAc and slowly add a solution of 2.95 mL (57.8 mmol) of Br$_2$ in 10 mL of HOAc over a period of 20 min. Stir the reaction mixture at room temperature, then concentrate in vacuo to a residue. Add CH$_2$Cl$_2$ and water, then adjust to pH=8–9 with 50% NaOH (aqueous). Wash the organic phase with water, then brine and dry over Na₂SO₄. Concentrate in vacuo to give 11.3 g of the product.
Step D

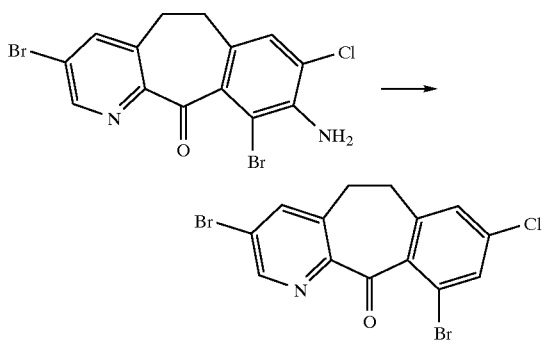

Cool 100 mL of concentrated HCl (aqueous) to 0° C., then add 5.61 g (81.4 mmol) of NaNO₂ and stir for 10 min. Slowly add (in portions) 11.3 g (27.1 mmol) of the product of Step C and stir the mixture at 0°–3° C. for 2.25 hrs. Slowly add (dropwise) 180 mL of 50% H₃PO₂ (aqueous) and allow the mixture to stand at 0° C. overnight. Slowly add (dropwise) 150 mL of 50% NaOH over 30 min., to adjust to pH=9, then extract with CH₂Cl₂. Wash the extract with water, then brine and dry over Na₂SO₄. Concentrate in vacuo to a residue and chromatograph (silica gel, 2% EtOAc/CH₂Cl₂) to give 8.6 g of the product.
Step E

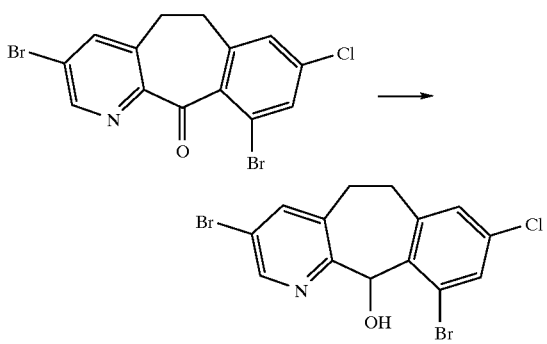

Combine 8.6 g (21.4 mmol) of the product of Step D and 300 mL of MeOH and cool to 0°–2° C. Add 1.21 g (32.1 mmol) of NaBH₄ and stir the mixture at ~0° C. for 1 hr. Add another 0.121 g (3.21 mmol) of NaBH₄, stir for 2 hr. at 0° C., then let stand overnight at 0° C. Concentrate in vacuo to a residue then partition the residue between CH₂Cl₂ and water. Separate the organic phase and concentrate in vacuo (50° C.) to give 8.2 g of the product.
Step F
3,10-dibromo-8,11-dichloro-6,11-dihydro-5H-benzo[5,6]cyclohepta[1,2-b]pyridine

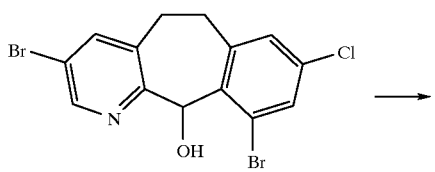

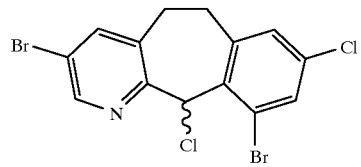

Combine 8.2 g (20.3 mmol) of the product of Step E and 160 mL of CH₂Cl₂, cool to 0° C., then slowly add (dropwise) 14.8 mL (203 mmol) of SOCl₂ over a 30 min. period. Warm the mixture to room temperature and stir for 4.5 hrs., then concentrate in vacuo to to give the title compound.

Preparative Example 7

N-(3-Pyridylmethyl)-4-piperidineacetamide

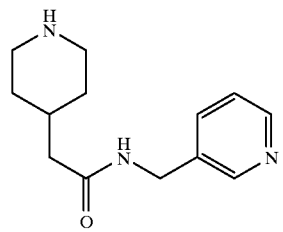

Step A 1-tert-butoxycarbonyl-N-(3-pyridylmethyl)-4-piperidineacetamide

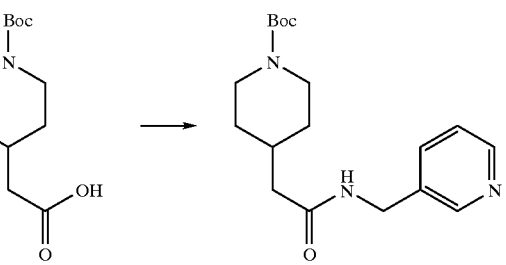

1-tert-Butoxycarbonyl-4-piperidineacetic acid (5 g, 20.55 mmoles) (prepared as described in Preparative Example 17, Step A in INO291K), 3-aminomethylpyridine (2.72 g, 26.7 mmoles), DEC.HCl (5.12 g, 26.7 mmoles), HOBT (3.61 g, 26.7 mmoles) and NMM (2.94 ml, 26.7 mmoles) are dissolved in anhydrous DMF (100 ml) and the mixture is stirred under argon at 25° C. for 22 h. The solution is evaporated to dryness and the residue is dissolved in dichloromethane, washed with 1N NaOH, dried over magnesium sulfate, filtered and evaporated to dryness. The residue is chromatographed on silica gel using 2% (10% conc. ammonium hydroxide in methanol)-dichloromethane as the eluant to give the title compound (6.05 g, 77%), ESIMS: m/z 334.1 (MH⁺).

Step B
N-(3-Pyridylmethyl)-4-piperidineacetamide

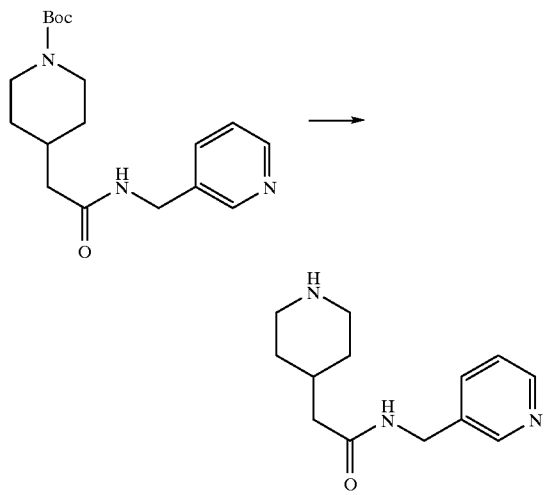

1-tert-Butoxycarbonyl-N-(3-pyridylmethyl)-4-piperidineacetamide (5.59 g, 16.76 mmoles) is dissolved in methanol (100 ml) and 10% conc. sulfuric acid in dioxane (v/v) (250 ml) is added. The mixture is stirred at 25° C. for 2 h and the neutralized with Bio Rad AG-1X8 (OH⁻) resin. The resin is washed with methanol and the eluate is evaporated to dryness. The residue is chromatographed on silica gel using 5%–20%–30% (10% conc. ammonium hydroxide in methanol)-dichloromethane as the eluant to give 3.64 g (93% yield) of the title compound: ESIMS: m/z 234.1 (MH⁺).

Preparative Example 8
N-(3-Pyridylmethyl)-4-piperidinepropanamide

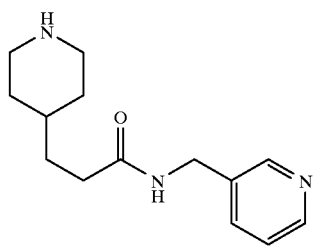

Step A
4-Piperidinepropionic acid

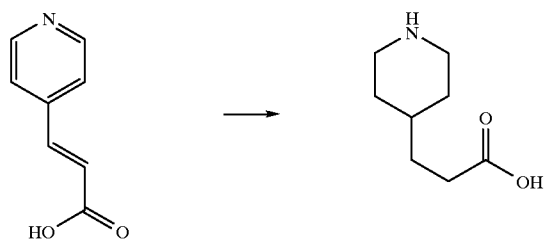

3-(4-Pyridyl)acrylic acid (2 g, 13.4 mmoles) is dissolved in water (70 ml) and concentrated hydrochloric acid (1 ml). 10% Pd-C (1.5 spatulas) is added and the mixture is hydrogenated at 25° C. at 55 psi for 72 h. The mixture is filtered through Celite® and then passed over a bed of Bio Rad AG 1-X8 (OH⁻) resin. The resin is washed with water and the combined eluates are evaporated to dryness to give the title compound that is used in Step B without further purification.

Step B
1-tert-Butoxycarbonyl-4-piperidinepropionic acid

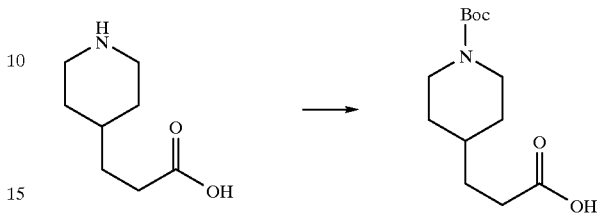

4-Piperidinepropionic acid (13.4 mmoles) (prepared as described in Step A above), di-tert-butyldicarbonate (3.22 g, 14.75 mmoles) and sodium hydroxide (0.5364 g, 13.4 mmoles) are dissolved in THF-water (1:1) (40 ml) and the mixture is stirred at 25° C. for 18 h. The mixture is passed over Bio Rad 50WX4 (H⁺) resin (15 ml bed) and the resin is washed with THF-water. The combined eluates are evaporated to dryness and then azeotroped with THF to give the title compound (2.72 g, 79%), FABMS: m/z 258.1 (MH⁺).

Step C
N-(3-Pyridylmethyl)-1-tert-butoxycarbonyl-4-piperidinepropanamide

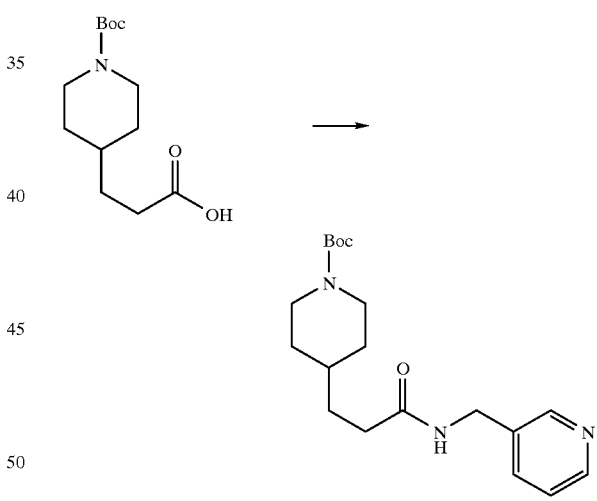

1-tert-Butoxycarbonyl-4-piperidinepropionic acid (2 g, 7.77 mmoles), 3-(aminomethyl)pyridine (1.029 ml, 10.1 mmoles), DEC.HCl (1.937 g, 10.1 mmoles), HOBT (1.365 g, 10.1 mmoles) and NMM (1.111 ml, 10.1 mmoles) are dissolved in anhydrous DMF (25 ml) and the mixture is stirred under argon at 25° C. for 20 h. The solution is evaporated to dryness and the residue is taken up in dichloromethane, washed with 0.3N NaOH, dried over magnesium sulfate, filtered and evaporated to dryness. The residue is chromatographed on silica gel using 1.5%–2.5% (10% conc. ammonium hydroxide in methanol)-dichloromethane as the eluant to give the title compound (2.555 g, 95%), ESIMS: m/z 348.1 (MH⁺).

Step D
N-(3-Pyridylmethyl)-4-piperidinepropanamide

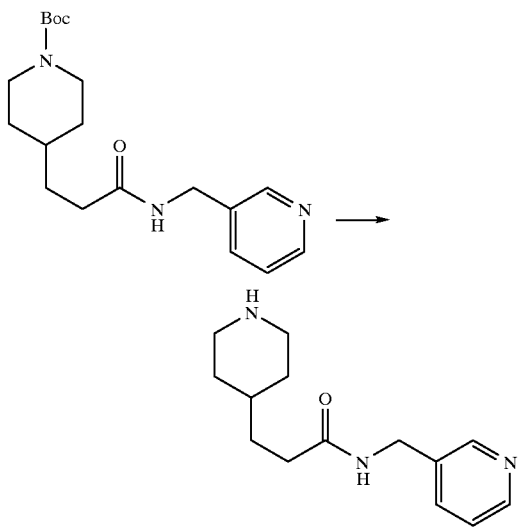

N-(3-Pyridylmethyl)-1-tert-butoxycarbonyl-4-piperidinepropanamide (2.222 g, 6.4 mmoles) is dissolved in methanol (38.15 ml) and 10% conc. $H_2SO_4$ in dioxane (v/v) (95.38 ml) is added and the mixture is stirred under argon at 25° C. for 1.5 h. The volume is reduced to half and the mixture is basified to pH 12 with 50% NaOH aq and extracted with dichloromethane. The latter is dried over magnesium sulfate, filtered and evaporated to dryness. The residue is chromatographed on silica gel using 10% (10% conc. ammonium hydroxide in methanol)-dichloromethane as the eluant to give the title compound (0.9586 g, 61%), CIMS: m/z 248.25 (MH$^+$).

Preparative Example 9
Ethyl 4-piperidineacetate

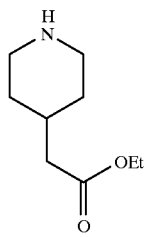

Step A
Ethyl 1-tert-butoxycarbonyl-4-piperidineacetate

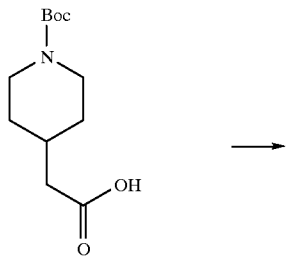

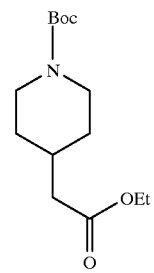

1-tert-Butoxycarbonyl-4-piperidineacetic acid (1 g, 4.1 mmoles) (prepared as described in Preparative Example 17, Step C in INO291 K), ethanol (200 proof) (0.284 g, 0.362 ml, 6.2 mmoles), DEC.HCl (1.18 g, 6.2 mmoles), HOBT (0.8331 g, 6.2 mmoles) and NMM (0.624 g, 0.678 ml, 6.2 mmoles) are dissolved in anhydrous DMF (30 ml) and the mixture is stirred at 25° C. under argon for 24 h. The solution is evaporated to dryness and the residue is dissolved in dichloromethane, washed with satd, NaHCO$_3$ aq, water, dried over magnesium sulfate, filtered and evaporated to dryness. The residue is chromatographed on silica gel using 0.5% (10% conc. ammonium hydroxide in methanol)-dichloromethane as the eluant to give the title compound (0.682 g, 61%), ESIMS: m/z 272.0 (MH$^+$).

Step B
Ethyl 4-piperidineacetate

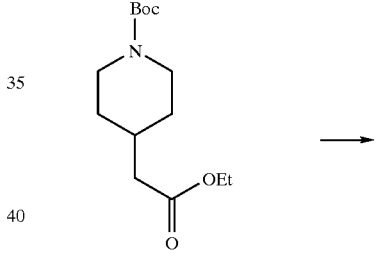

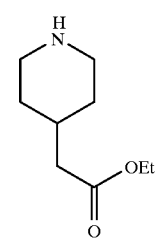

Ethyl 1-tert-butoxycarbonyl-4-piperidineacetate (0.6 g, 2.2 mmoles) is dissolved in ethanol (30 ml) and 10% conc. $H_2SO_4$ in dioxane (v/v) (30 ml) is added and the mixture is stirred at 25° C. for 2 h. The mixture is passed over a bed of Bio Rad AG1-X8 (OH$^-$) resin and the resin is then eluted with ethanol. The combined eluates are evaporated to dryness and the residue is chromatographed on silica gel using 1% (10% conc. ammonium hydroxide in methanol)-dichloromethane as the eluant to give the title compound.

Preparative Example 10
1-(8-Chloro-3,10-dibromo-6,11-dihydro-5H-benzo[5,6]cyclohepta[1,2-b]pyridin-11-yl)-4-piperidineacetic acid

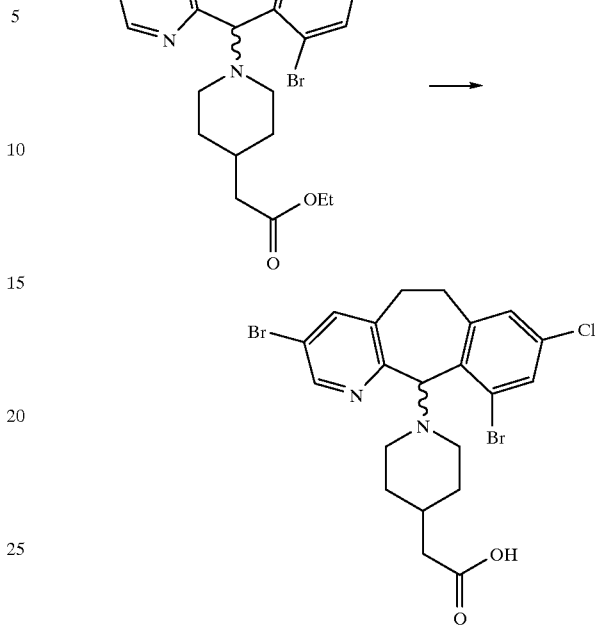

Step A

Ethyl 1-(8-Chloro-3,10-dibromo-6,11-dihydro-5H-benzo[5,6]cyclohepta[1,2-b]pyridin-11-yl)-4-piperidineacetate

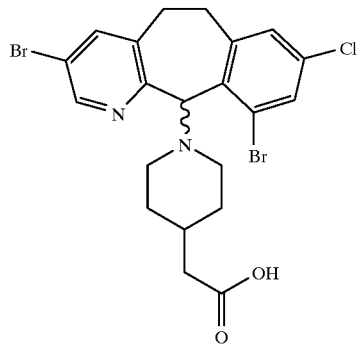

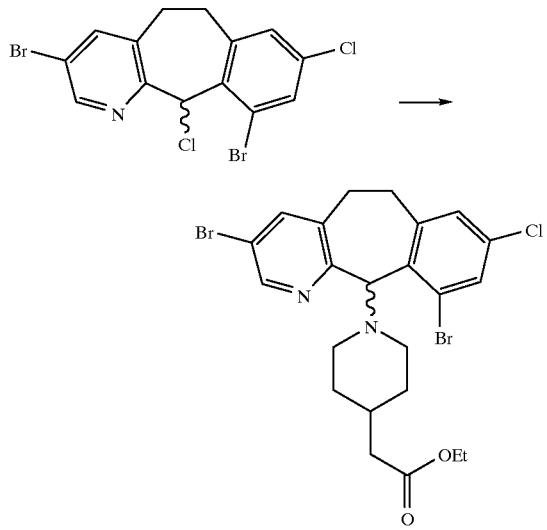

3,10-Dibromo-8,11-dichloro-6,11-dihydro-5H-benzo[5,6]cyclohepta[1,2-b]pyridine (prepared as described in Preparative Example 6, Step F) (0.486 g, 1.15 mmoles) is dissolved in anhydrous THF (5 ml). Ethyl 4-piperidineacetate (prepared as described in Preprative Example 9, Step B) (0.6241 g, 2.3 mmoles) and triethylamine (0.321 ml, 2.3 mmoles) in anhydrous THF (5 ml) are added and the mixture is stirred at 25° C. for 24 h. The solution is evaporated to dryness and the residue is dissolved in dichloromethane and washed with 1N NaOH , dried (MgSO₄), filtered and evaporated to dryness. The product is chromatographed on silica gel using 5% (10% conc. ammonium hydroxide in methanol)-dichloromethane as the eluant to give the title compound.

Step B 1-(8-Chloro-3,10-dibromo-6,11-dihydro-5H-benzo[5,6]cyclohepta[1,2-b]pyridin-11-yl)-4-piperidineacetic acid Ethyl 1-(8-Chloro-3,10-dibromo-6,11-dihydro-5H-benzo[5,6]cyclohepta[1,2-b]pyridin-11-yl)-4-piperidineacetate (0.3 g, 0.5 mmoles) (prepared as described in Step A above) is dissolved in ethanol (4 ml) and dichloromethane (4 ml) and 1M lithium hydroxide in water (1.21 mmoles) is added. The mixture is stirred at 50° C. for 5 h. 1N Hydrochloric acid (1.21 mmoles) is added and the solution is evaporated to dryness to give the title compound which is used without further purification.

Assays

1. In vitro enzyme assays

FPT $IC_{50}$ (inhibition of farnesyl protein transferase, in vitro enzyme assay) are determined by the methods disclosed in WO/10515 or WO 95/10516. The data demonstrate that the compounds of the invention are inhibitors of Ras-CVLS farnesylation by partially purified rat brain farnesyl protein transferase (FPT). The data also show that there are compounds of the invention which can be considered as potent ($IC_{50}<10$ μM) inhibitors of Ras-CVLS farnesylation by partially purified rat brain FPT.

Under the test protocols employed, there were certain compounds within the scope of the present invention which did not exhibit activity. It is believed that such compounds would exhibit activity under a different test protocol.

2. Cell-based assay

COS $IC_{50}$ values refer to the COS cells activity inhibition of Ras processing, are determined by the methods disclosed in WO/10515 or WO 95/10516.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

Example A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|   | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

Example B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|   | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

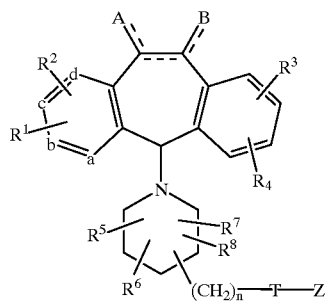

(1.0)

or a pharmaceutically acceptable salt or solvate thereof, wherein:

one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each of a, b, c, and d are independently selected from $CR^1$ or $CR^2$; each $R^1$ and each $R^2$ is independently selected from H, halo, $-CF_3$, $-OR^{10}$, $-COR^{10}$, $-SR^{10}$, $-S(O)_tR^{11}$ (wherein t is 0, 1 or 2), $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$, $-SR^{11}C(O)OR^{11}$, $-SR^{11}N(R^{75})_2$ wherein each $R^{75}$ is independently selected from H and $-C(O)OR^{11}$, benzotriazol-1-yloxy, tetrazol-5-ylthio, or substituted tetrazol-5-ylthio, alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, $R^7$ and $R^8$ each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{10}$, $OPO_3R^{10}$, or $R^5$ is combined with $R^6$ to represent =O or =S and/or $R^7$ is combined with $R^8$ to represent =O or =S;

$R^{10}$ represents H, alkyl, cycloalkyl, cycloalkylalkyl, heteroaryl, aryl, aralkyl or $-NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alkynyl;

$R^{11}$ represents alkyl or aryl;

the dotted line between carbon atoms 5 and 6 represents an optional double bond, such that when a double bond is present, A and B independently represent $-NO_2$, $-R^{10}$, halo, $-OR^{11}$, $-OCO_2R^{11}$ or $-OC(O)R^{10}$, and when no double bond is present between carbon atoms 5 and 6, A and B each independently represent $H_2$, $-(OR^{11})_2$, H and halo, dihalo, alkyl and H, (alkyl)$_2$, $-H$ and $-OC(O)R^{10}$, H and $-OR^{10}$, oxy, aryl and H, $=NOR^{10}$ or $-O-(CH_2)_p-O-$ wherein p is 2, 3 or 4;

n is 0, 1, 2, 3, 4, 5 or 6;

T is $-CO-$; $-SO-$; $-SO_2-$; or $-CR^{30}R^{31}-$ wherein $R^{30}$ and $R^{31}$ independently represent H, alkyl, aryl, aralkyl, heteroalkyl, heteroaryl, heteroarylalkyl, heterocycloalkyl or heterocycloalkylalkyl; and Z represents alkyl, aryl, aralkyl, heteroalkyl, heteroaryl, heteroarylalkyl, heterocycloalkyl, heterocycloalkylalkyl, $-OR^{40}$, $-SR^{40}$, $-CR^{40}R^{42}$, $-NR^{40}R^{42}$,

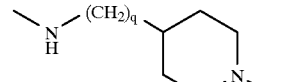

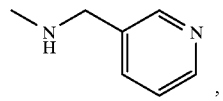

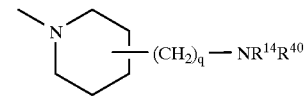

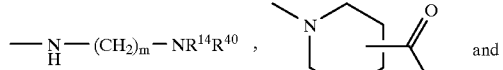

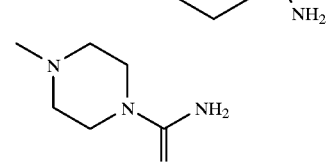

wherein n, $R^{40}$ and $R^{42}$ are defined hereinbefore, m is 2, 3 4, 5, 6, 7 or 8;

q is 0, 1 or 2;

and $R^{14}$ represents H, $C_{1-6}$ alkyl, aralkyl, heteroaryl, acyl, carboxamido, carboxamidoalkyl, cyano, alkoxycarbonyl, aralkyloxycarbonyl, D- and L-amino acids covalently bonded through the carboxyl group, imido, imidamido, sulfamoyl, sulfonyl, dialkylphosphinyl, N-glycosyl,

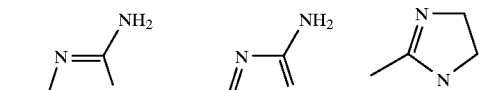

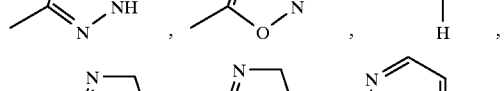

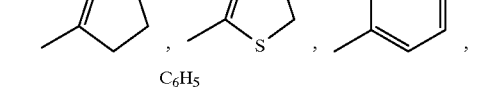

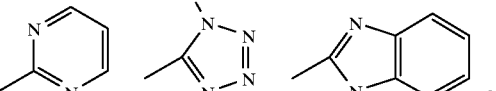

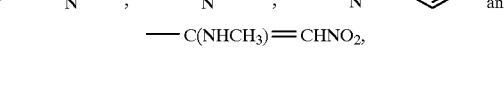

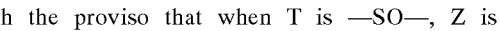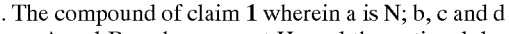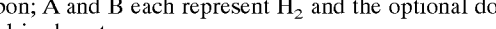

with the proviso that when T is $-SO-$, Z is not $-NR^{40}R^{42}$.

2. The compound of claim 1 wherein a is N; b, c and d are carbon; A and B each represent $H_2$ and the optional double bond is absent.

3. The compound of claim 2 wherein $R^1$ and $R^4$ are H and $R^2$ and $R^3$ are halo selected from chloro and bromo; or $R^1$ is H and $R^2$, $R^3$ and $R^4$ are halo selected from chloro and bromo.

4. The compound of claim 3 wherein $R^2$ and $R^3$ are halo in the 3- and the 8-position on the ring structure; or $R^2$, $R^3$ and $R^4$ are in the 3-, 8- and 10-position on the ring structure.

5. The compound of claim 4 wherein $R^2$ is Br and $R^3$ is Cl in the 3- and the 8-position on the ring structure; or $R^2$ is Br, $R^3$ is Cl and $R^4$ is Br in the 3-, 8- and 10-position on the ring structure.

6. The compound of claim 5 wherein each of $R^5$, $R^6$, $R^7$ and $R^8$ is H.

7. The compound of claim 6 wherein the moiety —$(CH_2)_n$—T—Z is bonded at the 2-, 3- or 4-position on the piperdinyl ring.

8. The compound of claim 7 wherein the moiety —$(CH_2)_n$—T—Z is bonded at the 2- or 3-position on the piperdinyl ring.

9. The compound of claim 8 wherein n is zero, 1 or 2; T is —CO— and Z is —$NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl or cycloalkylalkyl; or Z is

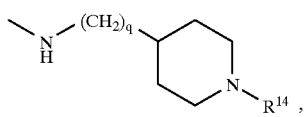

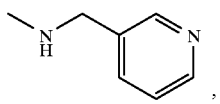

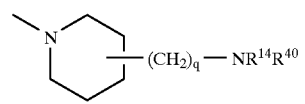

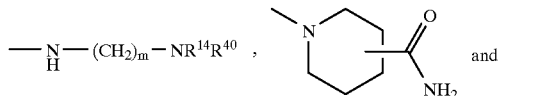

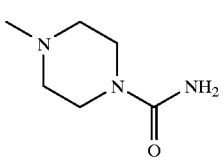

wherein $R^{40}$ is defined hereinbefore,
m is 2, 3 or 4;
q is 0 (zero), 1 or 2;
and $R^{14}$ represents H, $C_{1-6}$ alkyl, aralkyl, heteroaryl, acyl, carboxamido, carboxamidoalkyl, cyano, alkoxycarbonyl, aralkyloxycarbonyl imido, imidamido, sulfamoyl, sulfonyl, dialkylphosphinyl, N-glycosyl or —$C(NHCH_3)$=$CHNO_2$.

10. The compound of claim 9 wherein n is zero; Z is —$NR^{40}R^{42}$ wherein $R^{40}$ represents H and $R^{42}$ represents heteroarylalkyl.

11. The compound of claim 10 wherein $R^{40}$ is H and $R^{42}$ is 3-pyridylmethyl.

12. The compound of claim 9 which is any of the following compounds:

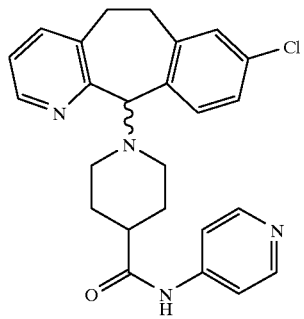

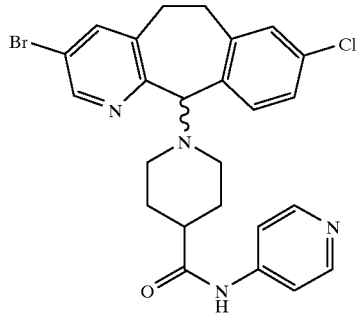

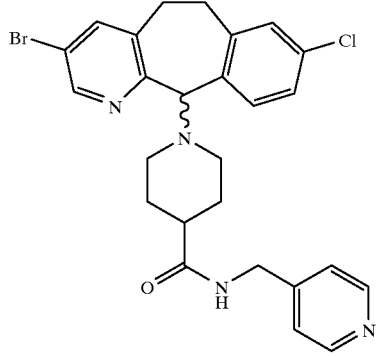

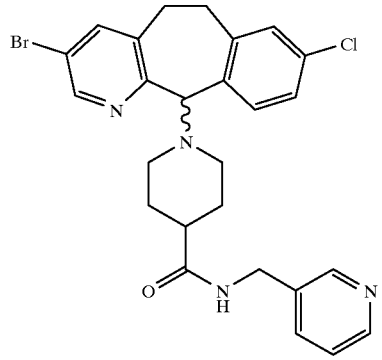

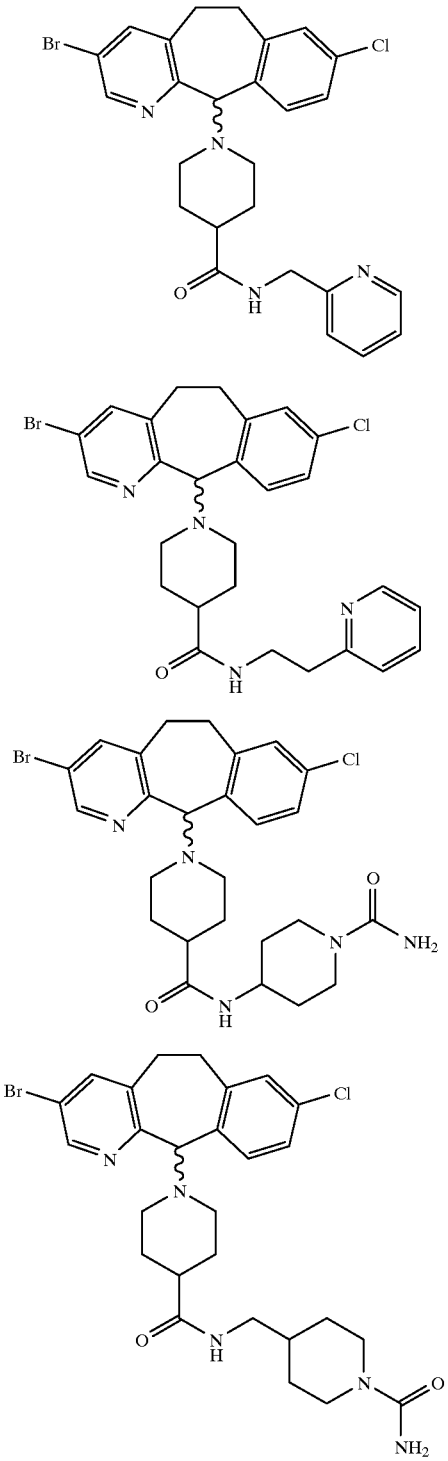
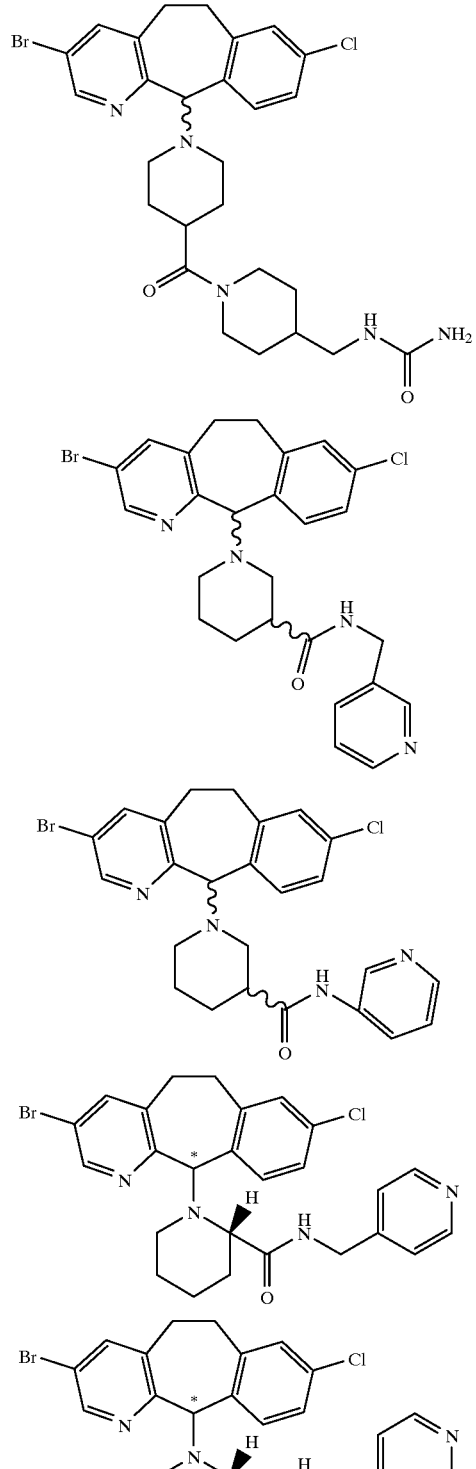

101
-continued
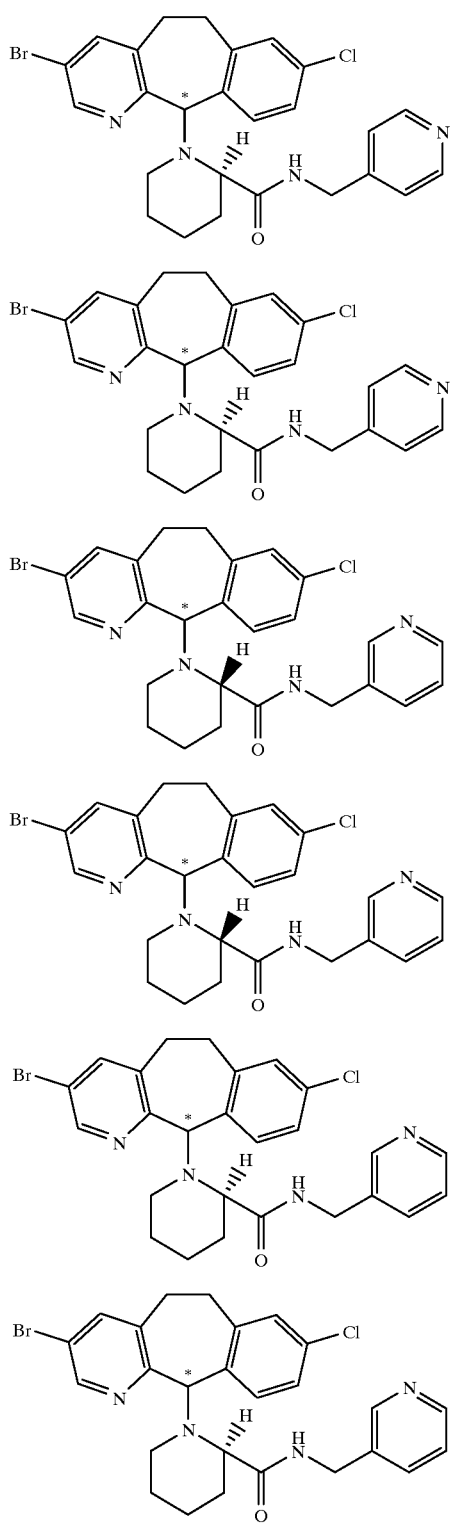
102
-continued
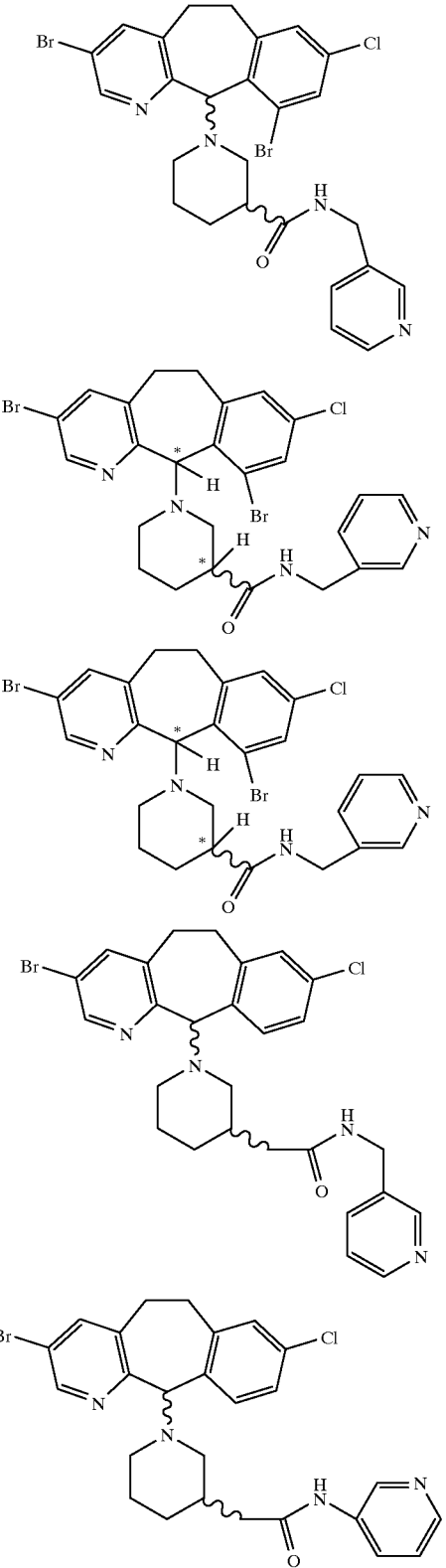

103
-continued
104
-continued
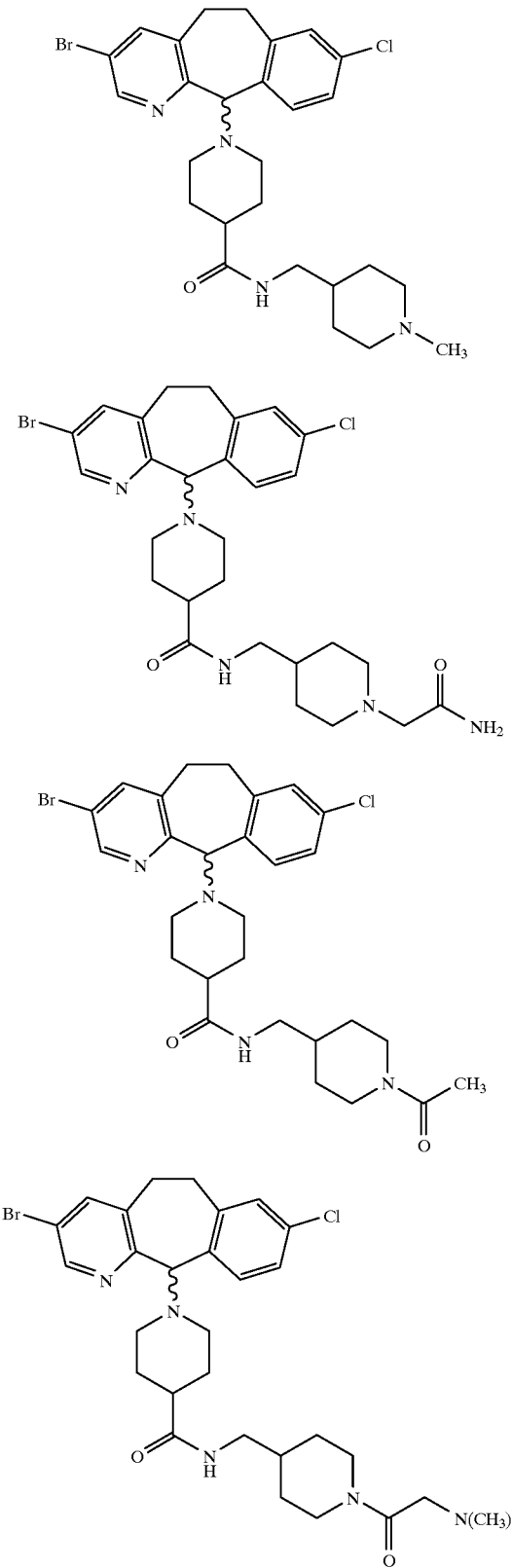
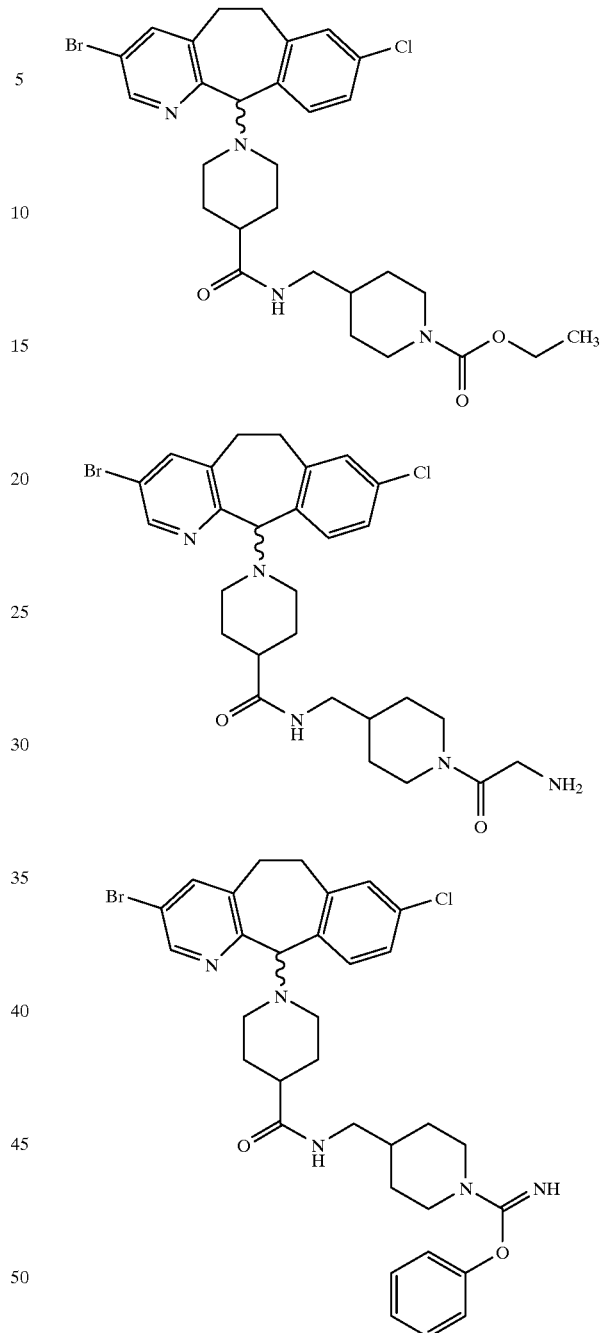

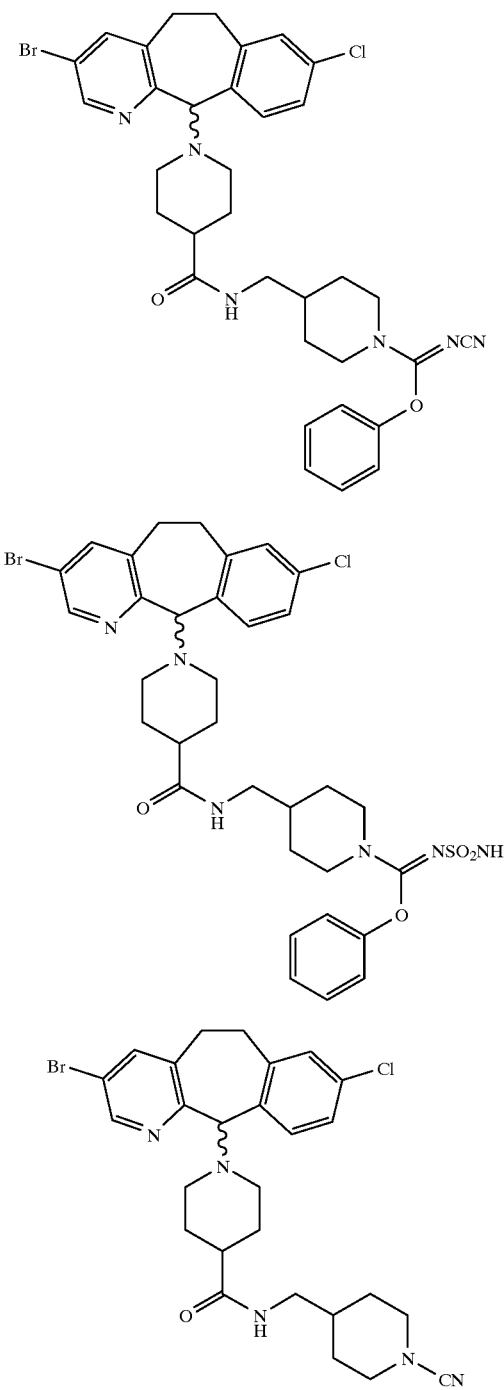
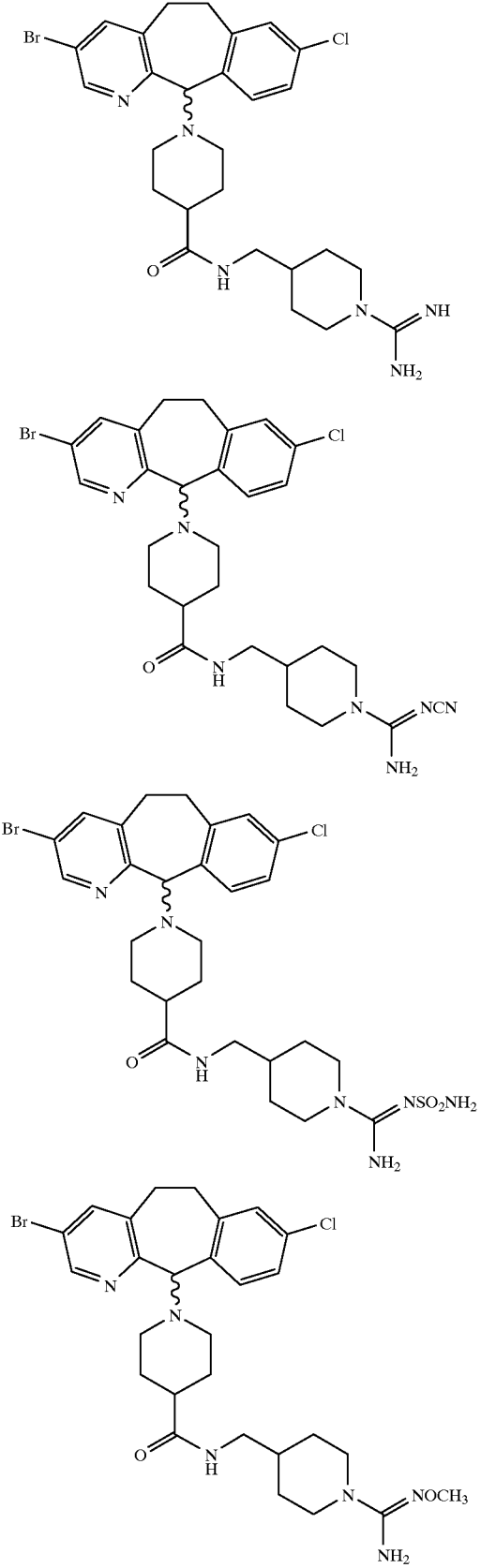

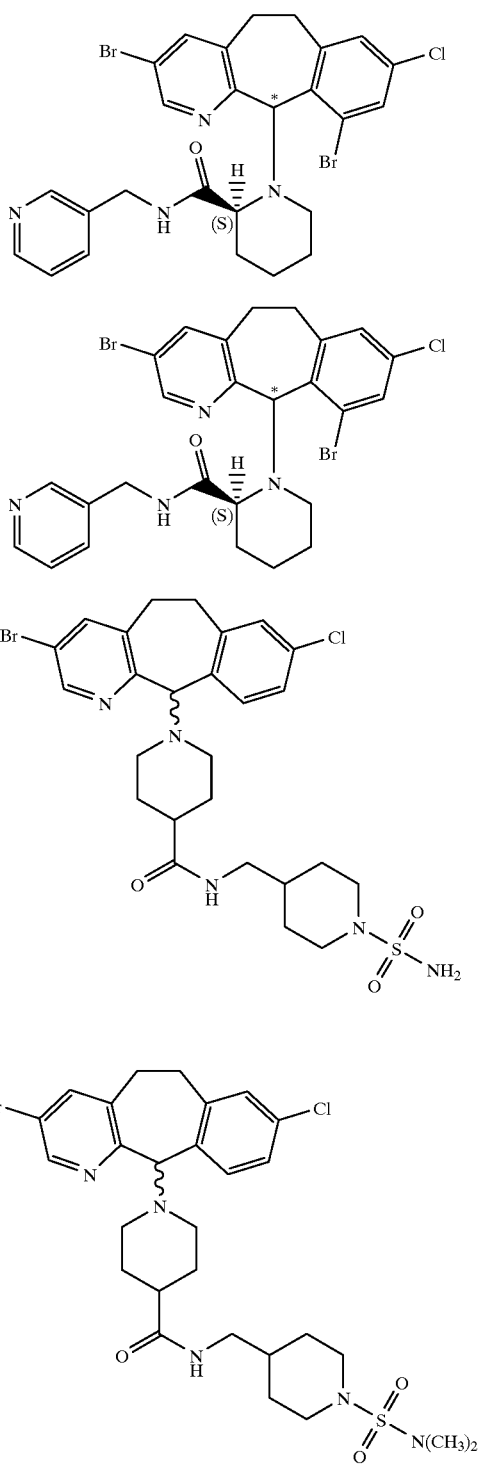
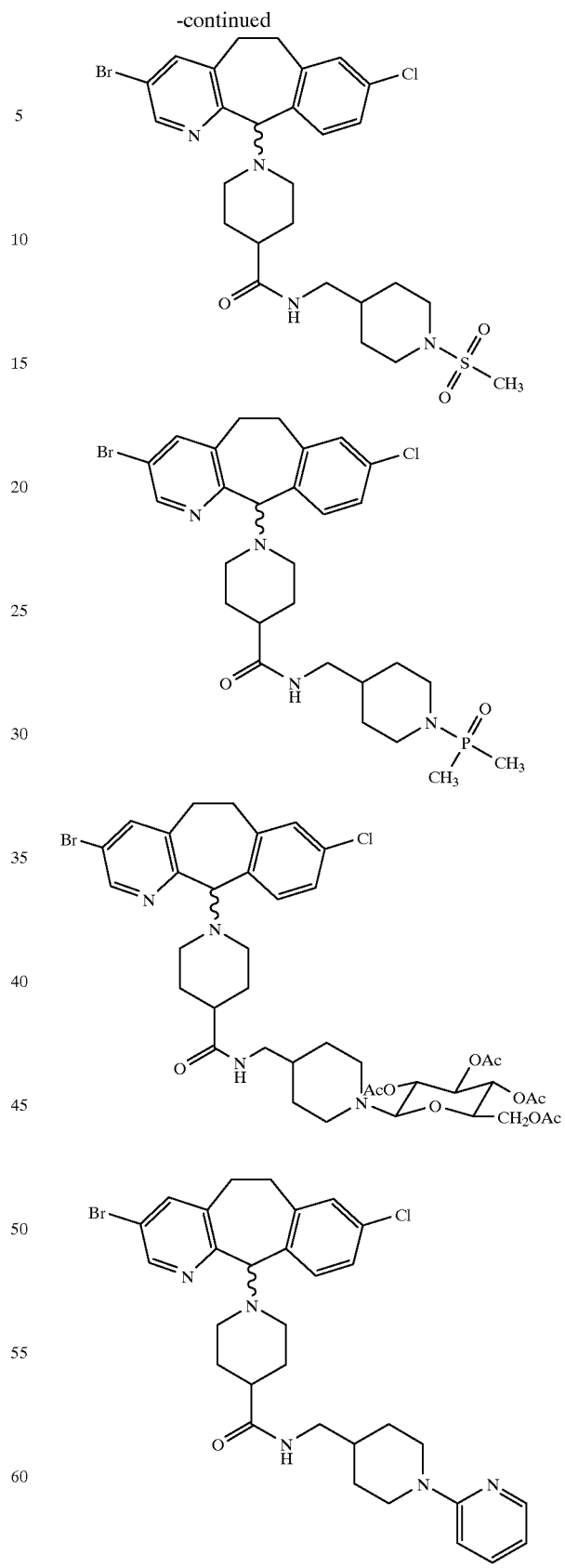

109
-continued
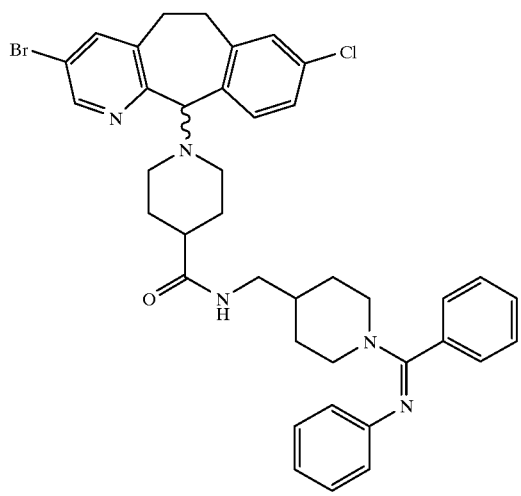
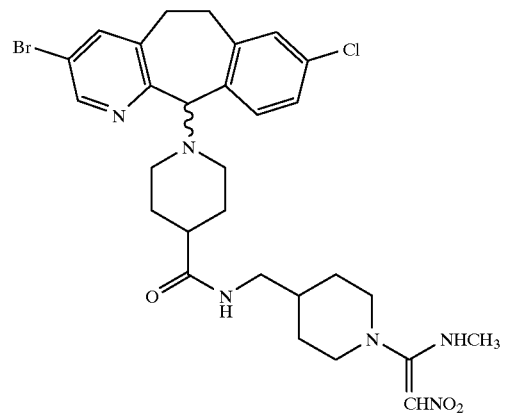
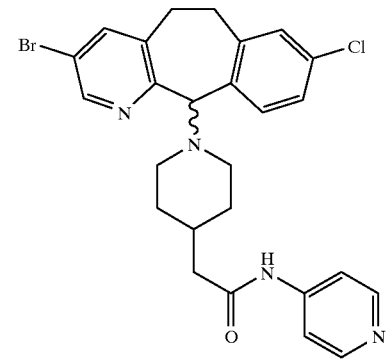
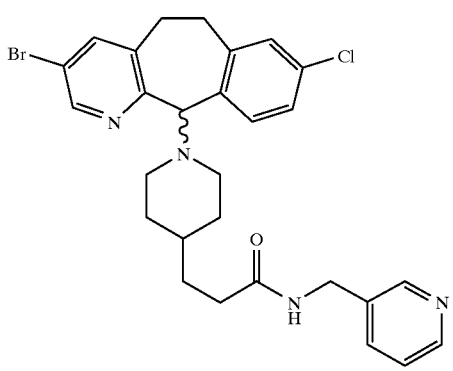
110
-continued
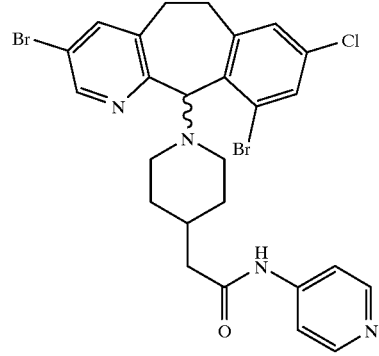
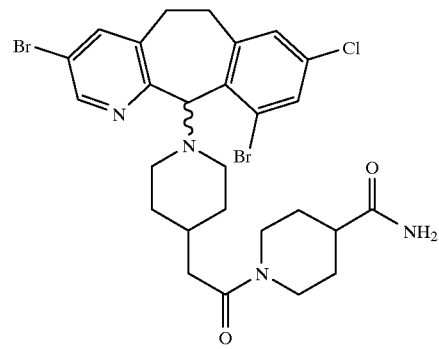
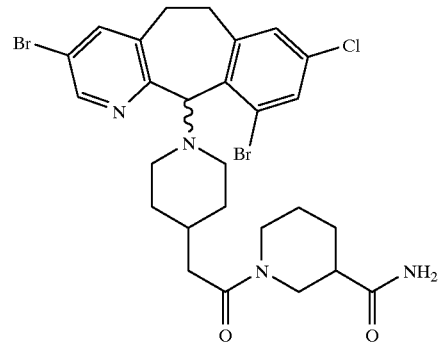
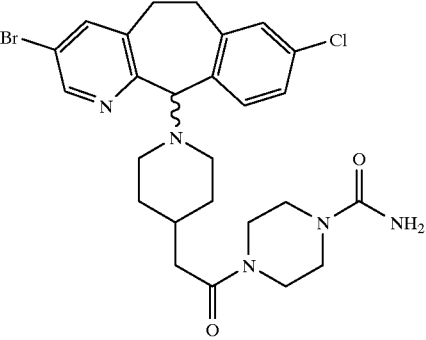
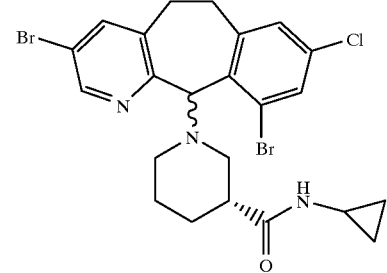

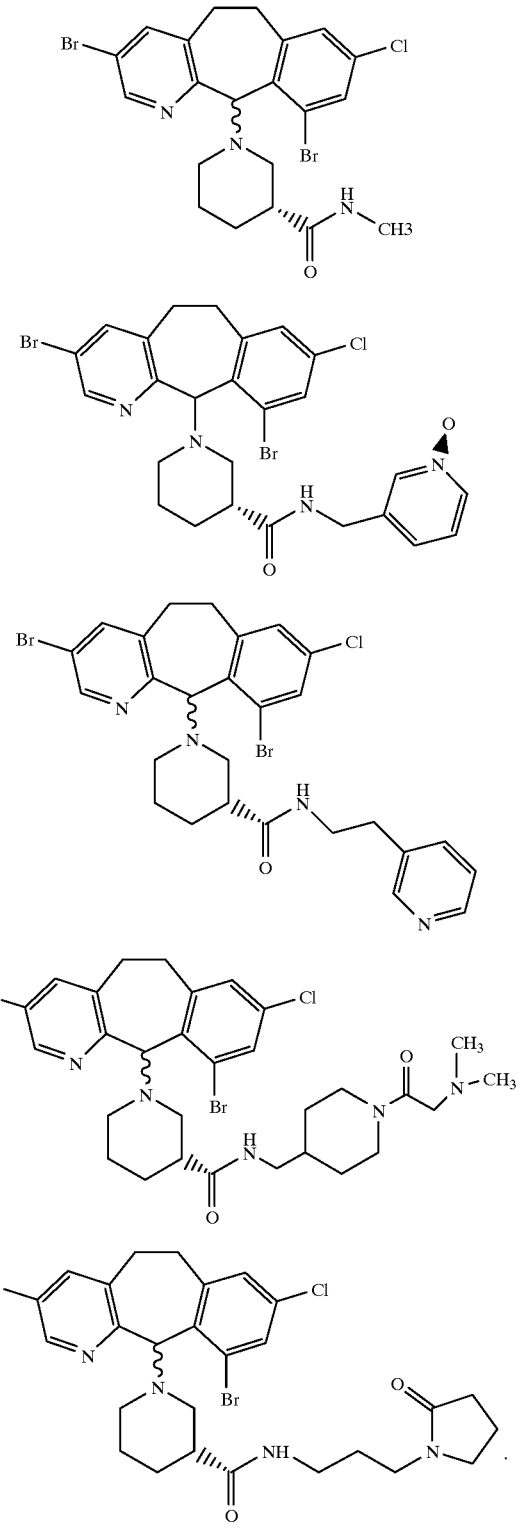
13. The compound of claim 12 which is selected from
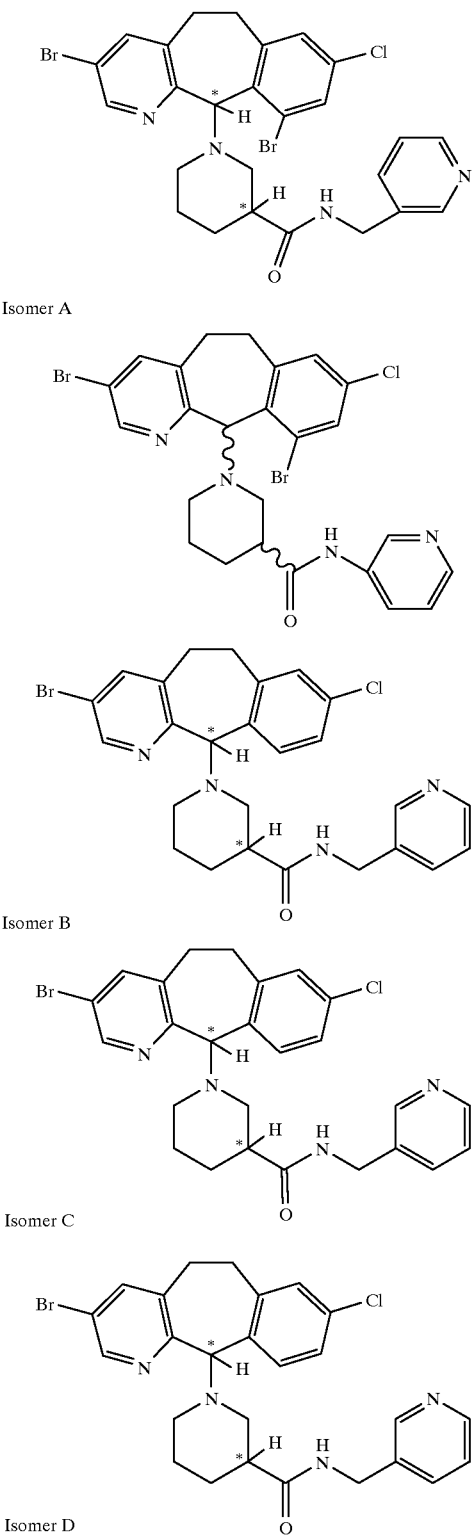

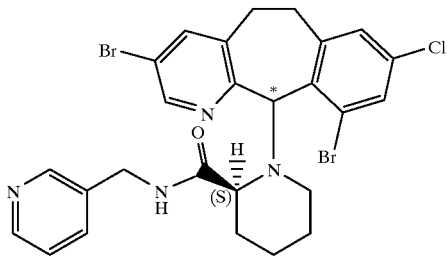

and Isomer D3 amide or a pharmaceutically acceptable salt thereof.

14. The compound of claim 13 which is

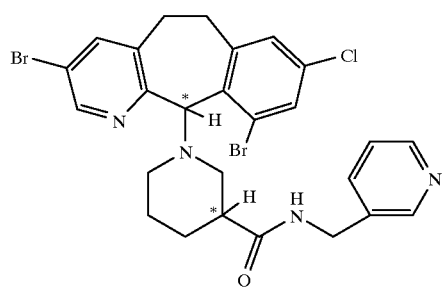

Isomer A
or

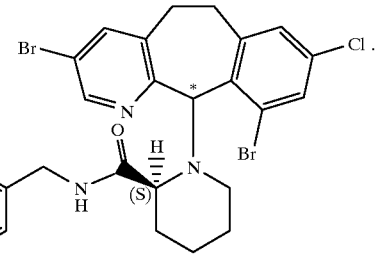

Isomer D3 amide

15. A pharmaceutical composition for inhibiting the abnormal growth of cells comprising an effective amount of compound of claim 1 in combination with a pharmaceutically acceptable carrier.

16. A method for inhibiting the abnormal growth of cells comprising administering an effective amount of a compound of claim 1.

17. The method of claim 16 wherein the the cells inhibited are tumor cells expressing an activated ras oncogene.

18. The method of claim 16 wherein the cells inhibited are pancreatic tumor cells, lung tumor cells, myeloid leukemia tumor cells, thyroid follicular tumor cells, myelodysplastic tumor cells, epidermal carcinoma tumor cells, bladder tumor cells or colon tumor cells.

19. The method of claim 16 wherein the inhibition of the abnormal growth of cells occurs by the inhibition of ras farnesyl protein transferase.

20. The method of claim 16 wherein the inhibition is of tumor cells wherein the Ras protein is activated as a result of oncogenic mutation in genes other than the Ras gene.

* * * * *